(12) United States Patent
Tillekeratne et al.

(10) Patent No.: US 7,893,268 B2
(45) Date of Patent: Feb. 22, 2011

(54) EPITHIOLONE ANALOGUES

(75) Inventors: Viranga Tillekeratne, Toledo, OH (US); Richard D. Hudson, Toledo, OH (US); Mamoun Alhamadsheh, Toledo, OH (US)

(73) Assignee: University of Toledo, Toledo, OH (US)

( * ) Notice: Subject to any disclaimer, the term of this patent is extended or adjusted under 35 U.S.C. 154(b) by 411 days.

(21) Appl. No.: 11/989,414

(22) PCT Filed: Jul. 20, 2006

(86) PCT No.: PCT/US2006/028169

§ 371 (c)(1),
(2), (4) Date: Jan. 25, 2008

(87) PCT Pub. No.: WO2007/015929

PCT Pub. Date: Feb. 8, 2007

(65) Prior Publication Data

US 2009/0258904 A1    Oct. 15, 2009

Related U.S. Application Data

(60) Provisional application No. 60/702,936, filed on Jul. 27, 2005.

(51) Int. Cl.
*C07D 213/72* (2006.01)
*C07D 405/00* (2006.01)

(52) U.S. Cl. .................................. 546/281.7; 546/342

(58) Field of Classification Search .............. 546/281.7, 546/342
See application file for complete search history.

(56) References Cited

U.S. PATENT DOCUMENTS

| 6,380,394 | B1 | 4/2002 | Nicolaou et al. |
| 6,660,758 | B1 | 12/2003 | Nicolaou et al. |
| 7,173,137 | B2 | 2/2007 | Nicolaou et al. |
| 2003/0004338 | A1 | 1/2003 | Li et al. |
| 2003/0176368 | A1 | 9/2003 | Danishefsky et al. |
| 2004/0018598 | A1 | 1/2004 | Santi et al. |
| 2004/0127432 | A1 | 7/2004 | Nicolaou et al. |
| 2005/0033059 | A1 | 2/2005 | Danishefsky et al. |
| 2005/0043376 | A1 | 2/2005 | Danishefsky et al. |

FOREIGN PATENT DOCUMENTS

| WO | WO 2006/017761 A2 | 2/2006 |
| WO | WO 2007/015929 A2 | 2/2007 |
| WO | WO 2007/015929 | 2/2008 |

OTHER PUBLICATIONS

Cachoux et al, Angew. Chem. Int. Ed. 2005, 44, 7469-7473.*
Alhamadsheh et al. Organic Letters (2006), 8(4), 685-688.*
SciFinder Scholar, search results; Sep. 12, 2004; pp. 1-54.

* cited by examiner

*Primary Examiner*—Nizal S Chandrakumar
(74) *Attorney, Agent, or Firm*—MacMillan, Sobanski & Todd, LLC

(57) ABSTRACT

Epothilone analogues include a molecular scaffold which holds at least one segment of epothilone in a predetermined orientation and which rigidities a region between the macrolactone ring and the aromatic side-chain.

2 Claims, 22 Drawing Sheets

1. Colchicine

2. R = Me Vinblastine
   R = CHO Vincristine

3. Paclitaxel (Taxol®)

4a. R = H : Epothilone A 20 nM
4b. R = Me : Epothilone B 2 nM

4c. R = H : Epothilone C 12 nM
4d. R = Me : Epothilone D 17 nM

4e. R = H : Epothilone E
4f. R = Me : Epothilone F calcd. Log P of R
Pyridine analogues

| Compound | Epothilone B 4h | Epothilone D 4d | 6a | 6b | 6c | 6d | 6e |
|---|---|---|---|---|---|---|---|
| calcd. Log P of R Pyridine analogues | 4.68 | 4.46 | 4.17 | 5.3 | 3.81 | 3.77 | 4.88 |

US 7,893,268 B2

EPITHIOLONE ANALOGUES

This application claims the benefit of U.S. Provisional Application No. 60/702,936, filed Jul. 27, 2005, and International Application No. PCT/US2006/028169, filed Jul. 20, 2006. The disclosures of both applications are fully and expressly incorporated herein by reference.

BACKGROUND OF THE INVENTION

Microtubules are an essential component of the cytoskeleton. Agents that disrupt microtubule dynamics within the cell have the potential of arresting cell division and cell proliferation (anti-mitotic agents) and consequentially, acting as anticancer agents. Two types of such agents have been identified. One class inhibits the polymerization of α- and β-tubulin, to microtubules, and is exemplified by compounds such as colchicines 1 and vinca alkaloids 2 (FIG. 26), some of which are clinically used anticancer drugs. In contrast, the second class of anti-mitotic agents accelerates the polymerization of tubulin to microtubules and stabilizes them, thus inhibiting their depolymerization, an essential process during cell division. This second class is commonly referred to as microtubule-stabilizing agents. Paclitaxel (Taxol®) 3 (FIG. 26), initially isolated from the Pacific Yew tree, *Taxus bravifolia*, was the first of its kind reported and is already in clinical use.

A number of limitations are encountered in the clinical use of paclitaxel. One major limitation is its susceptibility to multiple drug-resistance. Several other compounds possessing the same mechanism of action as paclitaxel have been reported since then. Epothilones 4 (FIG. 27), originally isolated from the myxobacterium *Sorangium cellulosum*, constitute one such class. They are competitive inhibitors of paclitaxel binding and have been shown to compete for the same or overlapping binding sites on microtubules. From the point of view of anticancer properties, they possess a number of advantages over paclitaxel. Prominent among them is their activity against multiple drug resistant cell lines, which are resistant to paclitaxel.

Extensive studies on structure-activity relationship (SAR) of epothilones have been reported. Many analogues have been synthesized with the aim of improving the pharmacological profile of epothilones. A few epothilone analogues are in various stages of clinical development. Based on SAR studies, the structure of epothilone molecule has been divided into three main sectors (FIG. 28), namely: i) the acyl sector (sector 1); ii) the alkyl sector (sector 2); and, iii) the aryl sector (sector 3). The acyl sector has been shown to be critical for biological activity and is not amenable to major chemical modification, whereas the alkyl and the aryl sectors can accommodate some degree of chemical modification without losing biological activity. Further, the macrolactone ring has been reported to be important for biological activity, as open-chain analogues synthesized were inactive.

Despite the promising therapeutic utility of the epothilones, it would be desirable to investigate additional analogues as well as additional synthetic methodologies for the synthesis of existing epothilones, and analogues thereof, as well as novel analogues thereof.

In particular, given the interest in the therapeutic utility of this class of compounds, it would also be desirable to develop methodologies capable of providing significant quantities of any epothilones, or those described herein, for clinical trials and for large-scale preparation.

Due to the increasing interest in epothilones as anti-cancer agents, novel analogues of these compounds are needed and desired to more fully develop their therapeutic potential.

SUMMARY OF THE INVENTION

Described herein is a method of incorporating a molecular scaffold to hold the key segments of epothilone in a predetermined orientation.

The method includes incorporating a molecular scaffold to hold at least one segment of epothilone in cyclic epothilone analogues Also described herein is a method of rigidifying the region between the macrolactone ring and the aromatic side-chain in macrocyclic analogues for effective interaction with the tubulin receptor.

Also described herein is a method for assembling the two defined molecular segments into an epothilone analogue. In certain embodiments, the method includes synthesizing three fragments and coupling using a convergent strategy to generate the analogues. In certain embodiments, the method includes esterifying, then closing a macrolactone ring using an olefin metathesis approach.

In one aspect, the method includes synthesizing epothilone analogues:

by incorporating a molecular scaffold that holds at least one key component of epothilone in a favorable orientation for interaction with a tubulin receptor; and structurally rigidifying a region between the macrolactone ring and the aromatic side-chain in epothilone by incorporating a single-carbon bridge between C14 and C17 carbon atoms in the form of a substituted cyclopentene ring in order to generate an epothilone analogue molecule having proper orientation of structural residues for enhanced interaction with the tubulin receptor.

Various objects and advantages of this invention will become apparent to those skilled in the art from the following detailed description of the preferred embodiment, when read in light of the accompanying drawings.

BRIEF DESCRIPTION OF THE DRAWINGS

FIG. 8 shows diastereoselective formation of aldol 40a.
FIG. 12 shows the zinc borohydride reduction of (+/−) 48a.
FIG. 13 shows lipase resolution of (+/−) 52a.

DETAILED DESCRIPTION OF THE INVENTION

Figure 1:
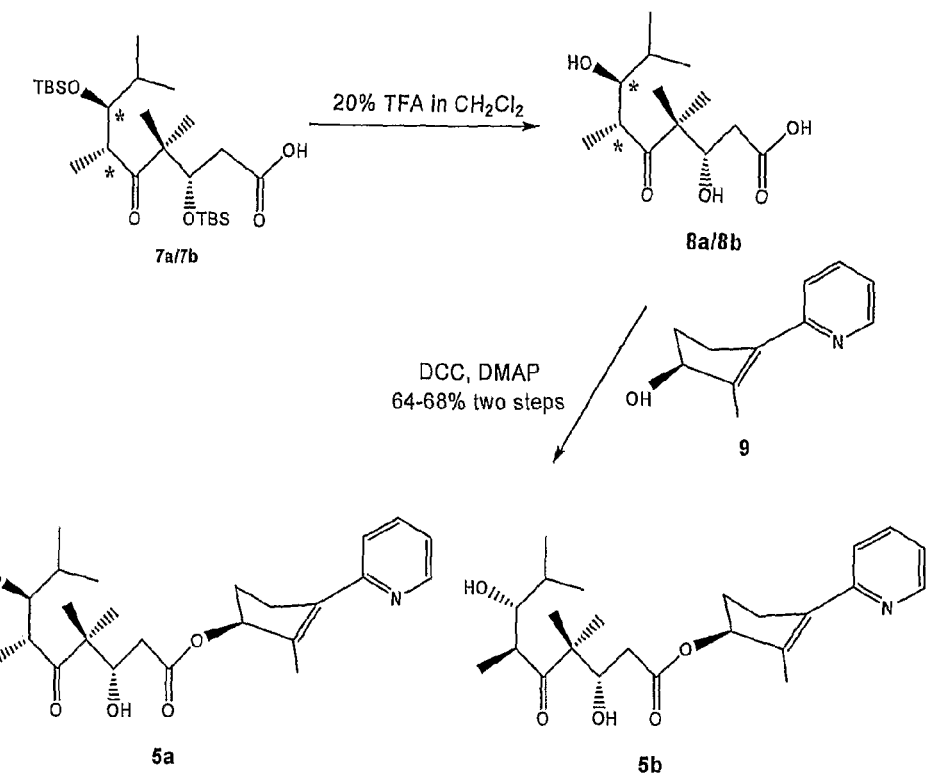
FIG. 1 shows the synthesis of 5a and 5b.

A method for synthesizing epothilone analogues includes incorporating a molecular scaffold to hold at least one segment of the epothilone analogue in a predetermined orientation. In certain embodiments, the epothilone analogue is adapted to interact with at least one tubulin receptor in a cell.

A method for synthesizing an epothilone analogue having a macrolactone ring and an aromatic side-chain, the method includes: i) incorporating a molecular scaffold to hold at least one segment of the epothilone analogue in a predetermined orientation; and, ii) rigidifying a region between the macrolactone ring and the aromatic side-chain.

A method for synthesizing an epothilone analogue having a macrolactone ring and an aromatic side-chain includes: i) incorporating a molecular scaffold that holds at least one sector of epothilone in a predetermined orientation for interaction with at least one tubulin receptor; and, ii) structurally rigidifying a region between the macrolactone ring and the aromatic side-chain in epothilone by incorporating a single-carbon bridge between C14 and C17 carbon atoms in epothilone in the form of a substituted cyclopentene ring.

In certain embodiments, the epothilone analogue has a predetermined orientation of structural residues that allows for enhanced interaction with a tubulin receptor. Also, in certain embodiments, the epothilone analogue comprises an open chain epothilone.

The method for synthesizing epothilone analogue can include coupling a suitable aldehyde fragment, a suitable ketone fragment and a suitable alcohol fragment using a convergent strategy.

The method is also useful to establish whether the conformational relationship of the aromatic side chain to the macrolactone ring contributes to the bioactivity of the epothilone molecule and offers an opportunity to synthesize active epothilone analogues. Also, the method is applicable to the synthesis of other important related analogues of the epothilone series.

In another aspect, an epothilone analogue composition includes a non-naturally occurring molecular scaffold. The molecular scaffold extends between a macrolactone ring and an aromatic side-chain in an analogue of an epothilone. In certain embodiments, the molecular scaffold comprises a single-carbon bridge between C14 and C17 carbon atoms in an epothilone analogue in the form of a substituted cyclopentene ring.

The epothilone analogue, or a salt thereof, can comprise:

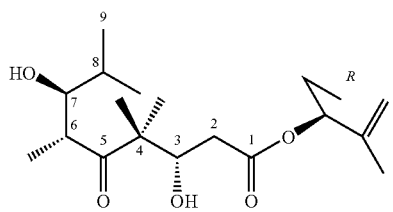

wherein R comprises phenyl, 2-pyridyl or other heteroaromatic, including

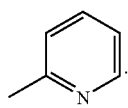

The epothilone analogue, or a salt thereof, can comprise:

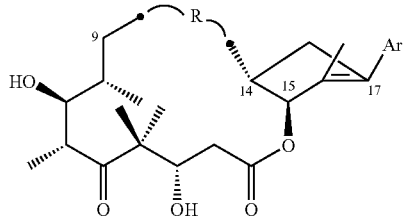

where Ar comprises phenyl, 2-pyridyl or other heteroaromatic, and wherein R a connecting link of variable hydrophobicity, length containing double bonds, or other heteroatom (such as N, O, S) functionality, and other combinations thereof.

In another aspect, pharmaceutical preparations can contain at least one epothilone analogue as well as a pharmaceutically compatible vehicle. In certain embodiments, the pharmaceutical compositions are useful for the treatment of a disease or condition characterized by cellular hyperproliferation. A method for treating a disease or condition characterized by cellular hyperproliferation in a subject suffering therefrom, includes administering a therapeutically effective amount an epothilone analogue.

In another aspect, epothilone analogues are useful for their anticancer activity are described, including, for example, the epothilone analogues, Described herein are epothilone compounds that are useful for the treatment of cancer and other conditions characterized by undesirable cellular proliferation. Also described herein are open-chain analogues of epothilones and cyclic analogues of epothilones.

In another aspect, methods for preparing the compounds are provided. In one embodiment, certain of the compounds are prepared by total synthesis.

In another aspect, formulations comprising one or more of these compounds are provided. In one embodiment, the compounds constitute the active principle of the formulation. In another embodiment, the compounds are combined with other active compounds, such as cytotoxic agents and synergists.

In another aspect, methods for treating a disease or condition with the compounds are provided. In one embodiment, the compounds are used for treating a disease or condition characterized by cellular hyperproliferation in a subject. In one embodiment, the disease is cancer, including but not limited to cancers of the head and neck, liver or biliary tract, intestine, ovary, lung, central nervous system, lymphatic system, or sarcomas. In another embodiment, the condition includes cellular hyperproliferative disorders Statements regarding the definitions of terms used herein are listed below. The definitions apply to the terms as they are used throughout this specification, unless otherwise limited in specific instances, either individually or as part of a larger group.

Unless stereochemistry is specifically indicated, all stereoisomers of the compounds are included, as pure compounds as well as mixtures thereof.

Some of the crystalline forms for the compounds may exist as polymorphs and as such are included. In addition, some of the compounds may form solvates with water (i.e., hydrates) or common organic solvents.

Protected forms of the compounds are included. A variety of protecting groups are disclosed; for example, a hydroxy protected form of the compounds are those where at least one of the hydroxyl groups is protected by a hydroxy protecting group.

In another aspect, prodrugs of the compounds are included. In general, such prodrugs are functional derivatives of the compounds that are readily convertible in vivo into the required compound. Thus, in the methods of treatment, the term "administering" includes the treatment of the various disorders described with the compound specifically disclosed or with a compound which may not be specifically disclosed, but which converts to the specified compound in vivo after administration to a subject in need thereof. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" is a medium that is used to prepare a desired dosage form of the compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like.

The term "purified," as used in reference to a compound means that the compound is in a preparation in which the compound forms a major component of the composition, such as constituting about 50%, about 60%, about 70%, about 80%, about 90%, about 95% or more by weight of the components in the composition.

Pharmaceutical preparations can include at least one of the compounds as described above and herein, or a pharmaceutically acceptable derivative thereof, which compounds are capable of inhibiting the growth of or killing cancer cells, and, in certain embodiments, are capable of inhibiting the growth of or killing multidrug resistant cancer cells. In certain embodiments, the pharmaceutical preparation also comprises as solubilizing or emulsifying agent.

In yet another aspect, methods for inhibiting tumor growth and/or tumor metastasis are provided. In certain embodiments, the method includes treating cancers by inhibiting tumor growth and/or tumor metastasis for tumors of multidrug resistant cancer cells. The method involves the administration of a therapeutically effective amount of the compound or a pharmaceutically acceptable derivative thereof to a subject (including, but not limited to a human or animal) in need of it. In certain embodiments, specifically for treating cancers comprising multidrug resistant cancer cells, the therapeutically effective amount is an amount sufficient to kill or inhibit the growth of multidrug resistant cancer cell lines. In certain embodiments, the compounds are useful for the treatment of solid tumors.

It will be appreciated by one of ordinary skill in the art that asymmetric centers may exist in the compounds. Thus, the compounds and pharmaceutical compositions thereof may be in the form of an individual enantiomer, diastereomer or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures described herein encompass those structures in which double bonds are (Z) or (E).

It will be appreciated that the compounds, as described herein, may be substituted with any number of substituents or functional moieties. In general, the term "substituted" whether preceded by the term "optionally" or not, and substituents contained in formulas refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of explanation herein, heteroatoms such as nitrogen may have hydrogen substituents and/or any permissible substituents of organic compounds described herein which satisfy the valencies of the heteroatoms.

Furthermore, there not any intention to be limited in any manner by the permissible substituents of organic compounds. Combinations of substituents and variables envisioned are preferably those that result in the formation of stable compounds useful in the treatment, for example, of proliferative disorders, including, but not limited to cancer.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Also provided are pharmaceutical agents that are based on pharmaceutically compatible compounds, i.e., compounds that are nontoxic in the doses used, optionally together with commonly used adjuvants and vehicles.

A composition generally comprises a compound and a pharmaceutically acceptable carrier. The compound may be in free form or where appropriate as pharmaceutically acceptable derivatives such as prodrugs, and salts and esters of the compound.

The composition may be in any suitable form such as solid, semisolid, or liquid form. In general, the pharmaceutical preparation will contain one or more of the compounds as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, cornstarch, keratin, colloidal silica, potato starch, urea, and other carriers suitable for use in manufacturing preparations, in solid, semi-solid, or liquefied form. In addition, auxiliary stabilizing, thickening, and coloring agents and perfumes may be used.

The amount of active ingredient that may be combined with the carrier materials to produce a single dosage form will vary depending upon the subject treated and the particular mode of administration. For example, a formulation for intravenous use comprises an amount of the compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

Methods of Treatment

In one aspect, the compounds are used to treat cancer. In one embodiment, the compounds are used to treat cancers of the head and neck which include tumors of the head, neck, nasal cavity, paranasal sinuses, nasopharynx, oral cavity, oropharynx, larynx, hypopharynx, salivary glands, and paragangliomas.

In another embodiment, the compounds are used to treat cancers of the liver and biliary tract, particularly hepatocellular carcinoma. In another embodiment, the compounds are used to treat intestinal cancers, particularly colorectal cancer. In another embodiment, the compounds are used to treat ovarian cancer. In another embodiment, the compounds are used to treat small cell and non-small cell lung cancer.

In another embodiment, the compounds are used to treat breast cancer. In another embodiment, the compounds are used to treat sarcomas which include fibrosarcoma, malignant fibrous histiocytoma, embryonal rhabdomyosocarcoma, leiomysosarcoma, neurofibrosarcoma, osteosarcoma, synovial sarcoma, liposarcoma, and alveolar soft part sarcoma. In another embodiment, the compounds are used to treat neoplasms of the central nervous systems, particularly brain cancer.

In another embodiment, the compounds are used to treat lymphomas that include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

The method comprises administering a therapeutically effective amount of a compound to a subject suffering from cancer. The method may be repeated as necessary either to mitigate (i.e. prevent further growth) or to eliminate the cancer. Clinically, practice of the method will result in a reduction in the size or number of the cancerous growths and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions can be used in combination therapies. In other words, the compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved. In another aspect the compounds are used to treat non-cancer disorders that are characterized by cellular hyperproliferation (e.g., an abnormally increased rate or amount of cellular proliferation).

Figure 29:
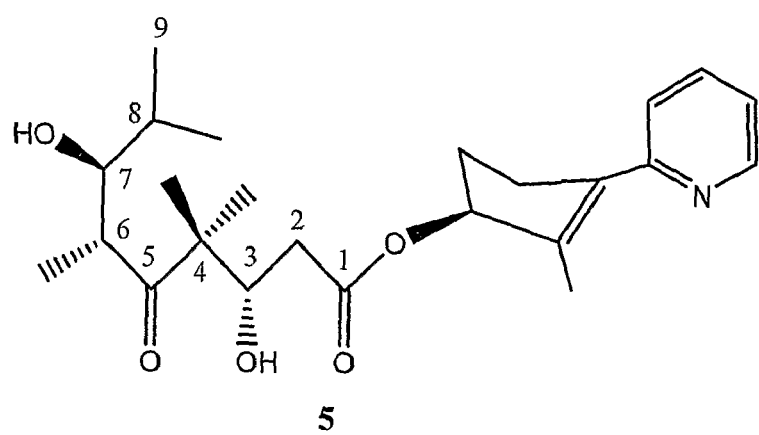
FIG. 29 shows open chain epothilone analogues.

The synthesis of epothilone analogues as anticancer agents is based on two methodologies:

Analogues incorporating a molecular scaffold that holds the key components of epothilone, critical for biological activity, in favourable orientation for interaction with the tubulin receptor to form compounds with significant biological activity (FIG. 29). This is contrary to the present knowledge that ring-open epothilone analogues are not biologically active.

Structural simplification accompanying such chemical modification increases the therapeutic index of such molecules and thereby leads to molecules of higher pharmacologic profile.

Figure 30:
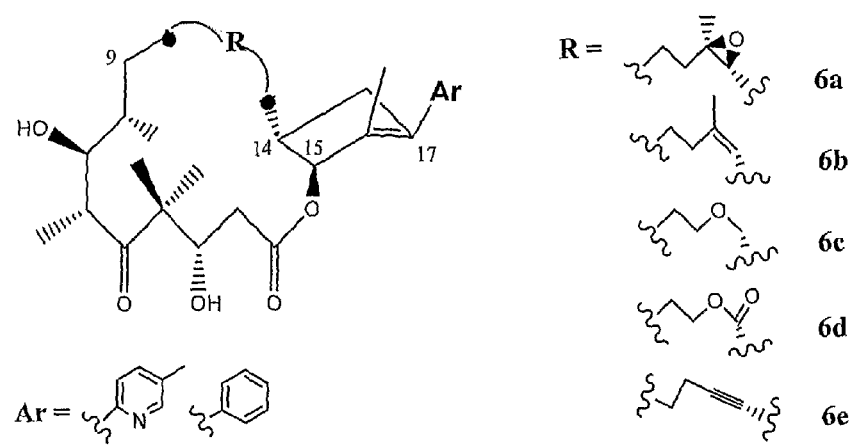
FIG. 30 shows designed epothilone analogues (6a-6e).

Structural rigidification of the region between the macrolactone ring and the aromatic side-chain by incorporating a single-carbon bridge between the C14 and C17 carbon atoms in the form of a substituted cyclopentene ring in order to generate molecules with proper orientation of structural residues for enhanced interaction with the tubulin receptor (FIG. 30). Such molecules have improved pharmacologic profiles for development as potent anticancer agents. It is to be understood, that in other embodiments, the Ar can comprise phenyl, 2-prridyl or other heteroaromatic, and R can comprise a connecting link of variable hydrophobicity, length (usually 2 or 3 carbons) containing double bonds, or other heteroatom (such as N, O, S) functionality, and other combinations thereof.

Using the above two methods two classes of compounds of the types as shown in FIGS. 29 and 30 were made. In designing sector 2 of structurally rigidified analogues (FIG. 30), the lipophilicity factor was taken into consideration since it is proposed to play a role in some epothilone analogues with high tubulin-binding activity and low cytotoxicity. The log P values of several analogues were calculated and compared with the corresponding values for epothilones B 4b & D 4d (see table in FIG. 30). The substituents in sector 2 were modulated to obtain analogues with a variable lipophilicity in order to study the effect of lipophilicity on ligand partitioning through cell membrane and ligand-receptor interaction. Compounds 6a, 6b, and 6e have lipophilicities comparable to those of the active epothilones. A variety of functionalities with different lipophilicities were introduced to circumvent any potential difficulty associated with the compound's ability to penetrate the cell membrane of the tumor cell.

The overall molecular geometry of the designed analogues was similar to that of the natural epothilones as shown by preliminary molecular modeling studies. Further, the C9-C15 distance was maintained close to that of the natural epothilones so that the conformation of the macrolactone remained as close as possible to that of the natural epothilones. The C9-C15 distance across the macrolactone ring of 6a and 6e was found to be 4.40 Å and 4.46 Å, respectively, compared to 4.20 Å for epothilone B 4b.

Docking of the analogue 6a on to the taxane-binding site on tubulin[24] showed the following interactions within 3 Å; i. C12-13 epoxide oxygen and HIS-229, ii. C2-OH and ARG-278, iii. C4-Me and ARG-278 (carbonyl backbone) and GLN-281 (backbone), iv. C7-OH and LEU-371 side chain, v. pyridine ring with ASP-226 side chain and LEU-219 side chain. In a similar study with 30e, the following interactions were observed: i. pyridine ring with ASP-226, ii. HIS-229 with LEU-219, iii. C7-OH with GLN-281, iv. C14 triple bond-C11 segment was maintaining contacts with SER-277 and THR-276. The designed compounds were synthesized as described below.

Figure 2:
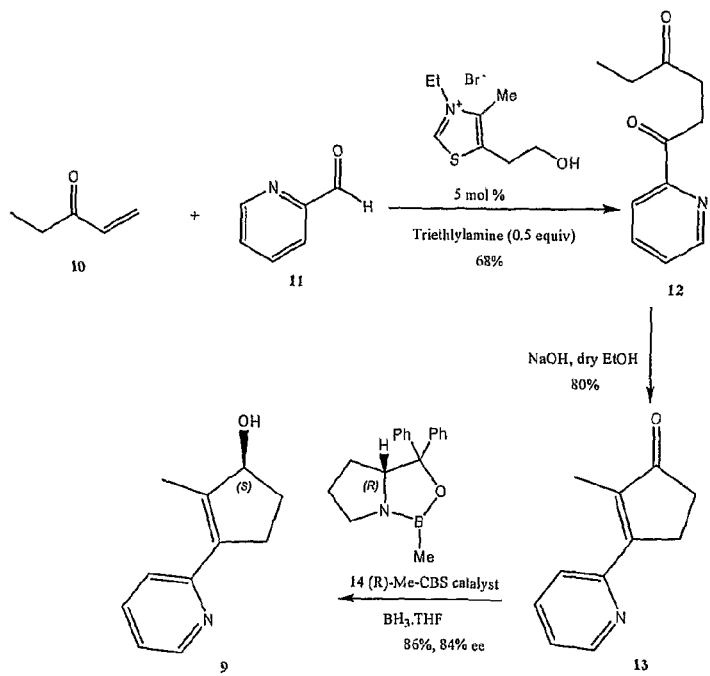
FIG. 2 shows the synthesis of alcohol fragment 9.
Figure 3A:
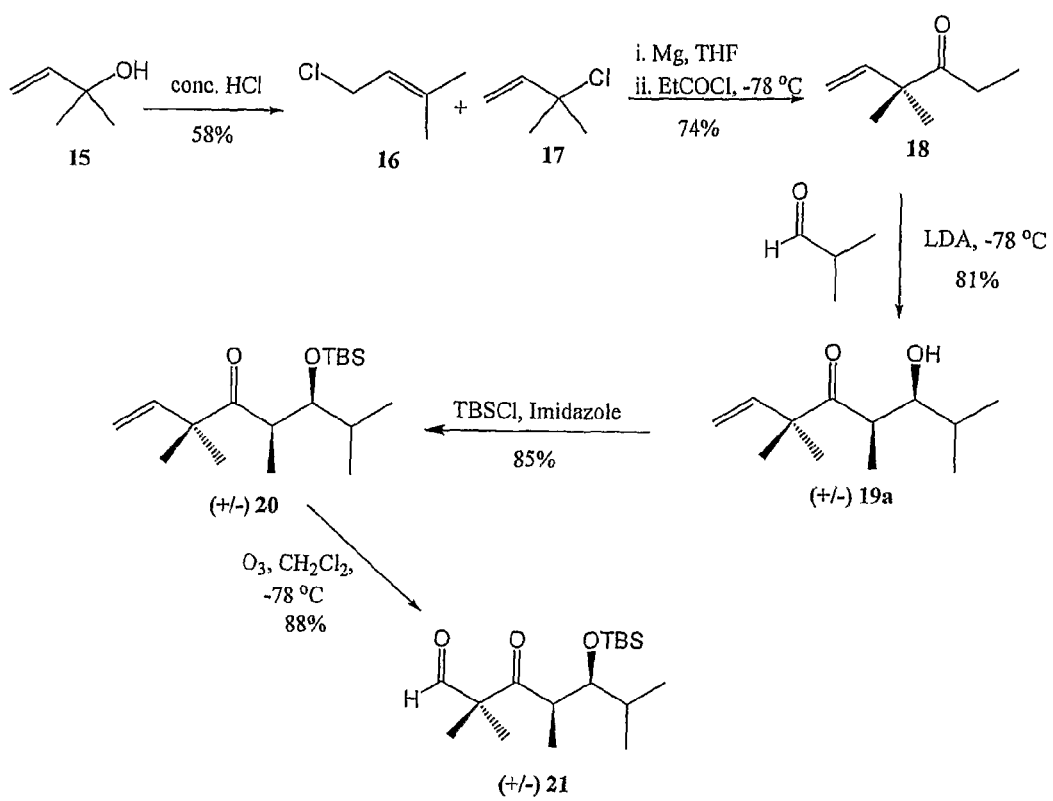
FIG. 3a shows the synthesis of carboxylic acid fragment 7a and 7b.

I. Synthesis of Open-Chain Epothilone Analogues:

The open-chain analogues (FIG. 29) were synthesized by esterifying an alcohol fragment 9 (FIG. 1) incorporating the molecular scaffold and the aromatic side chain of epothilone with a carboxylic acid fragment resembling the acyl sector 8a/8b (racemic at the *). The alcohol and the carboxylic acid fragments were separately synthesized (FIGS. 2 and 3, respectively). FIG. 1 shows the synthesis of 5a and 5b.

Synthesis of Alcohol Fragment 9

The synthesis of alcohol 9 was accomplished as shown in FIG. 2. The thiazolium salt-catalyzed addition of 2-pyridinecarboxaldehyde 11 to the activated double bond of ethyl vinyl ketone furnished the diketone 12,[76] which was cyclized by intramolecular aldol condensation to the cyclopentenone 13. Enantioselective reduction of ketone 13 using (R)-2-methyl-CBS-oxazaborolodine catalyst (CBS; Corey, Bakshi, and Shibata)[74] gave the desired (S)-alcohol 9 in a very good yield (86%) and enantioselectivity (84% ee). The absolute stereochemistry and enantiomeric excess of alcohol 9 was confirmed by Mosher ester analysis.[77,78]

Synthesis of Carboxylic Acid Fragment 7

The synthesis of carboxylic acid 7 was undertaken in a nine-step sequence as shown in FIG. 3. Prenyl chloride 16 and its isomer 17 were prepared as mixture from the commercially available alcohol 15 by reaction with concentrated hydrochloric acid.[79] Compounds 16 and 17 were obtained in a 6:1 ratio. The reaction was thermodynamically controlled (25° C.) and favored the more stable product 16 over 17. The prenyl chloride mixture was then converted to the corresponding Grignard reagent. Subsequent reaction with propionyl chloride gave a crude product which was purified by fractional distillation to give the unsaturated ketone 18 as a colorless oil.[75] The formation of 18 and not the tertiary alcohol was favored by slow addition of the Grignard reagent to an excess (2 equivalents) of propionyl chloride at −78° C. The carbonyl group of compound 18 was also blocked from a rapid second addition because of steric hindrance.

By kinetically controlling the mixed aldol reaction between ketone 18 and isobutyraldehyde through formation of the Z enolate of 18 using a bulky base (LDA) at −78° C., a racemic mixture of the desired syn aldol (+/−) 19a was formed without formation of the anti product.[75,80] The steric hindrance in the transition state, due to 1,3-diaxial interaction between the isopropyl group of isobutyraldehyde and the bulky group of ketone 18, prevented the formation of the racemic anti product (+/−) 19b (FIG. 3). No attempt was made to separate the racemic syn aldols (+/−) 19a at this stage. The secondary alcohol functional group of compound (+/−) 19a was protected using tert-butyldimethylsilyl chloride to give (+/−) 20. Aldehyde (+/−) 21 was produced by ozonolysis of olefin (+/−) 20 under reducing conditions using $Ph_3P$. The crude oily product was purified by silica gel column chromatography to give compound (+/−) 21 in excellent yield.

Figure 3B:
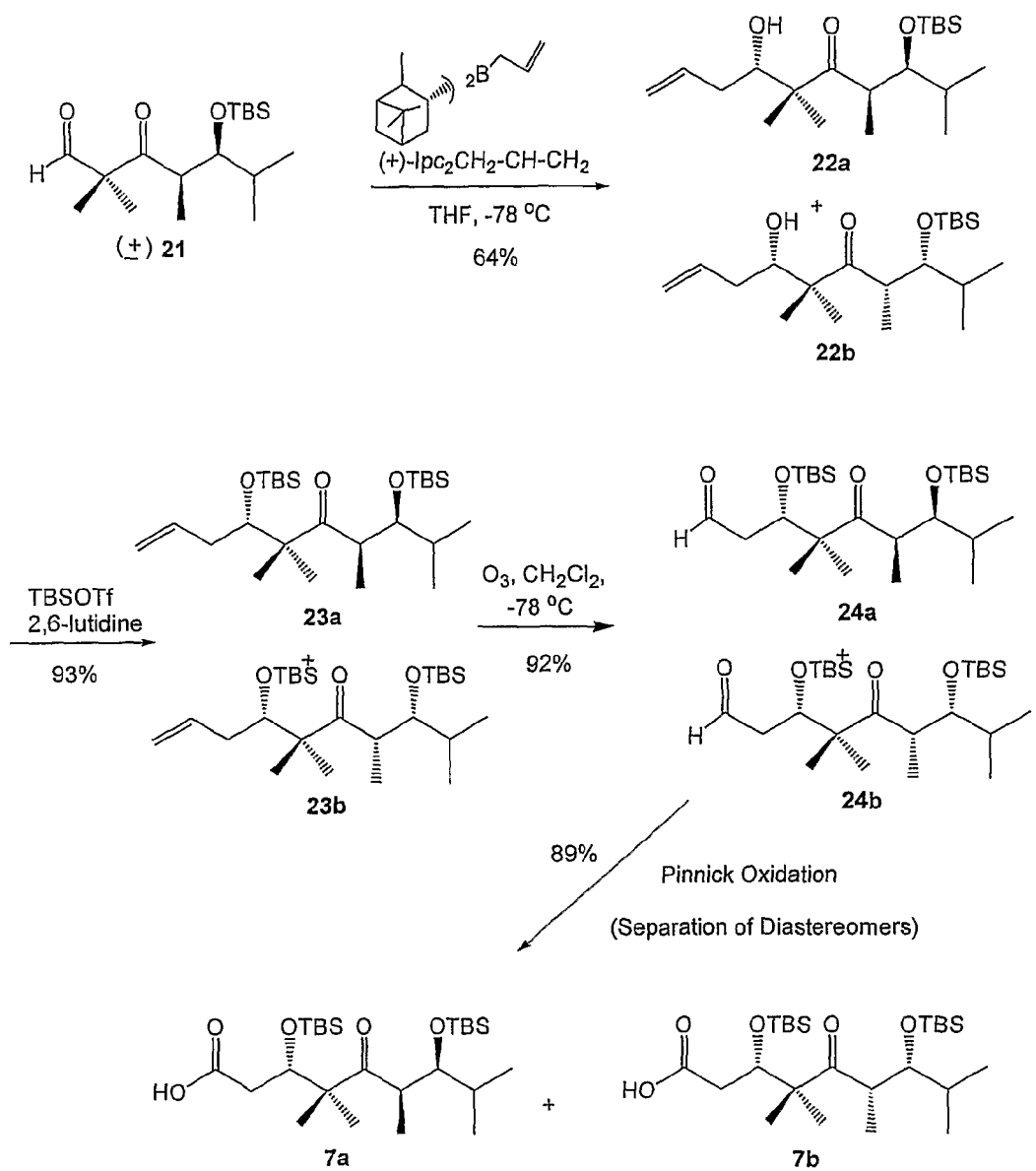
FIG. 3b shows the continued synthesis of carboxylic acid fragment 7a and 7b.

Compound (+/−) 21 was enantioselectively converted to the homoallylic alcohols 22a and 22b by reaction with (+)-allyldiisopinocampheylborane (FIG. 3b). The (S) stereochemistry at homoallylic alcohol attached carbon was confirmed by Mosher ester analysis.[77,78] Since compound (+/−) 21 was a racemic mixture, the products (22a and 22b) obtained by allylation represented a pair of diastereomers. However, the two diastereomers were not separated at this stage. The secondary hydroxyl groups of 22a/22b were protected using tert-butyldimethylsilyl trifluoromethanesulfonate (TBSOTf) and 2,6-lutidine to give 23a and 23b in excellent yield. Ozonolysis of the terminal olefin function of the 23a/23b mixture under reducing conditions ($Ph_3P$) gave the corresponding aldehydes 24a and 24b. The aldehydes 24a/24b were then converted to the corresponding diastereomeric acids 7a and 7b by Pinnick oxidation.[81] At this stage, the diastereomeric acids 7a and 7b were separated by column chromatography.

Coupling Between the Carboxylic Acids 7a/7b and Alcohol 9

Figure 4:
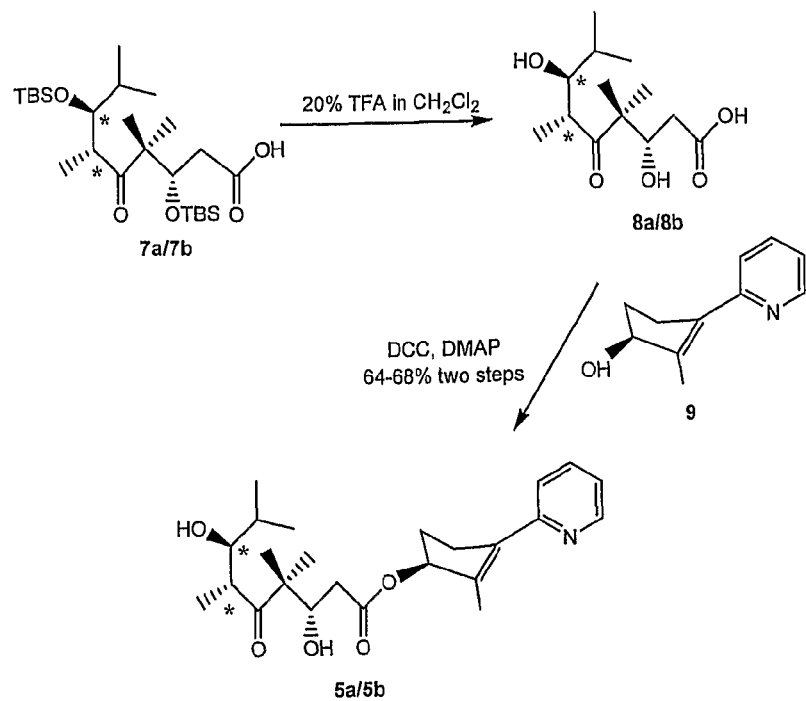
FIG. 4 shows the synthesis of 5a and 5b.

Treating fragments 7a/7b with 20% trifluoroacetic acid in methylene chloride resulted in the formation of the fully deprotected intermediates 8a/8b (FIG. 4). Esterification between 8a/8b and alcohol 9 resulted in the formation of the target molecules 5a/5b as the sole esterification products in good yield (64% over two steps).

II. Synthesis of Macrocyclic Epothilone Analogues

Figure 5:
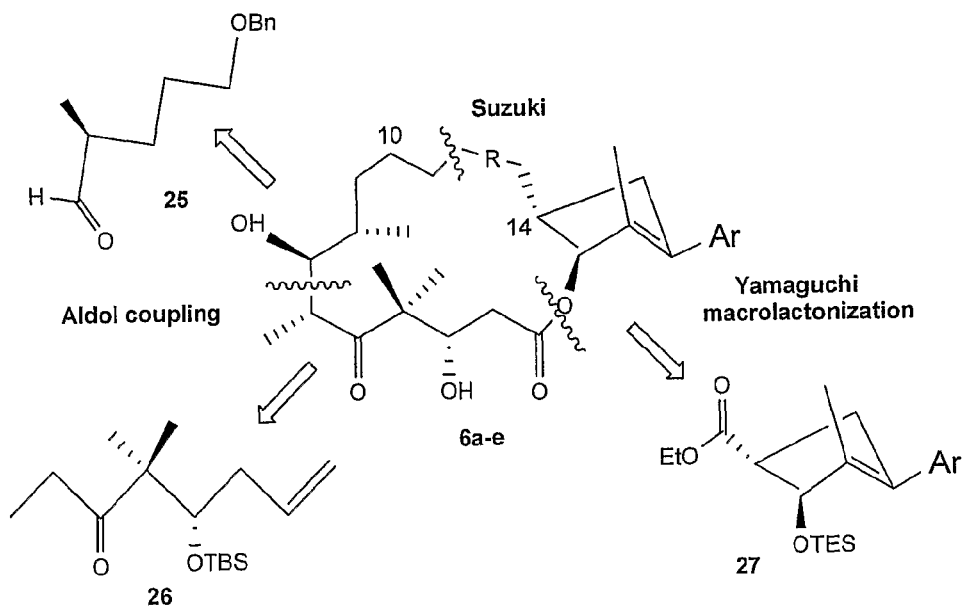
FIG. 5 shows the retrosynthetic strategy for the preparation of cyclic analogues.

The synthesis of analogues with a rigidified skeleton of the macrocyclic structure involved separate synthesis of three key fragments 25, 26 and 27, which were then coupled by a convergent strategy to generate the final product (FIG. 5). Aldehyde 25 and ketone 26 can be coupled by stereoselective aldol reaction. Depending on the target molecule, the northern segment (C10-C14) can then be inserted using one of several different synthetic strategies. Finally, Yamaguchi macrolactonization furnishes the final target.

Figure 6:
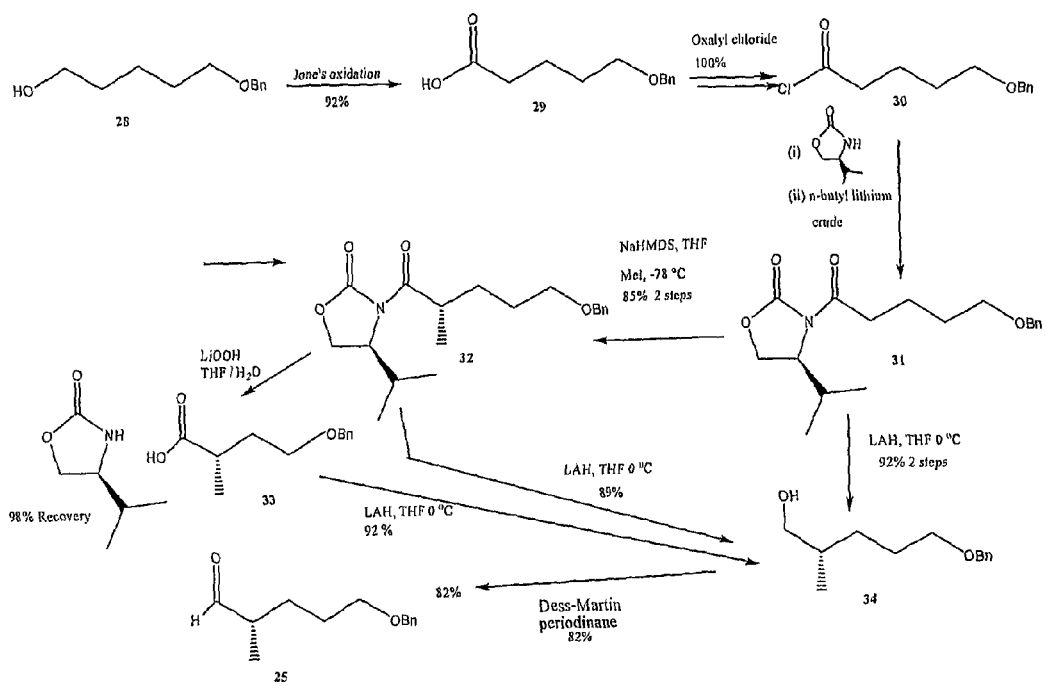
FIG. 6 shows the synthesis of key aldehyde fragment.
Figure 7:
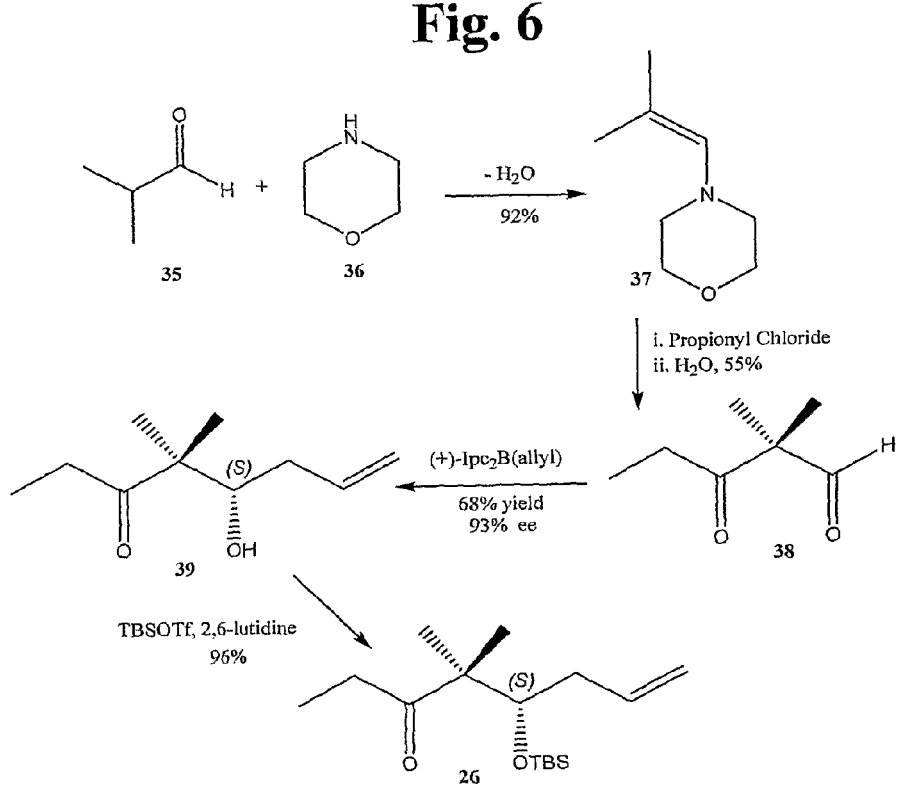
FIG. 7 shows the synthesis of key ketone fragment 26.
Figure 10:
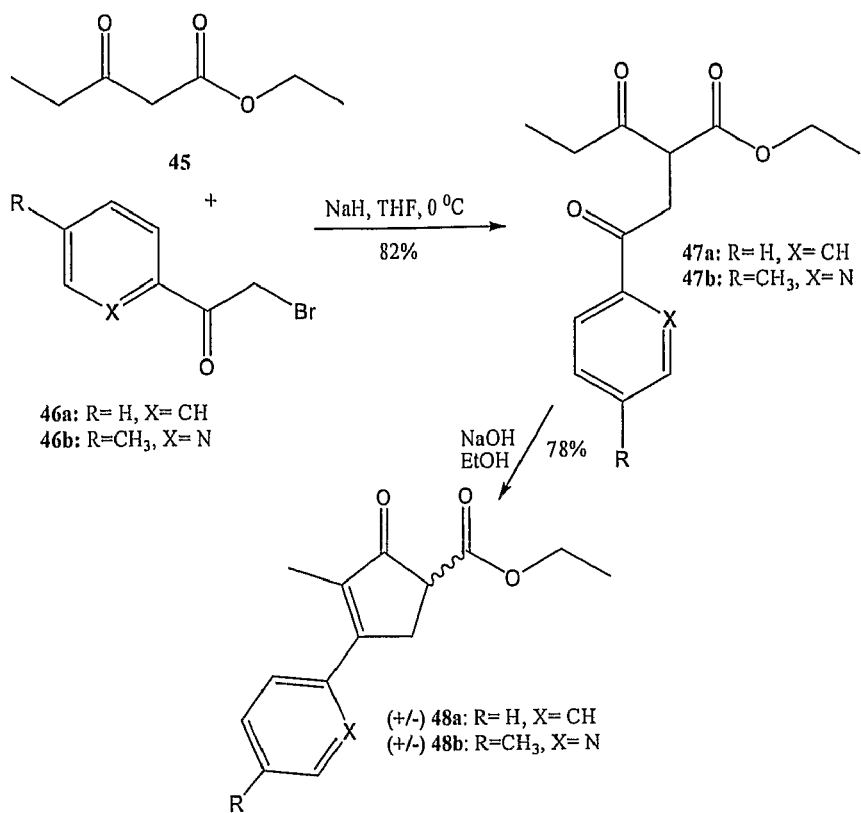
FIG. 10 shows the synthesis of (+/−) 48a and (+/−) 48b.

The syntheses of the three key fragments 25, 26 and 27 are shown in FIG. 6, FIG. 7, and FIG. 10, respectively.

Synthesis of the Aldehyde 25

Synthesis of the aldehyde 25 was approached as shown in FIG. 6 via Evans asymmetric alkylation protocol. The acyl chloride 30 was obtained from commercially available 5-benzyloxypentanol 28 by Jones oxidation followed by treatment with oxalyl chloride.[83] Coupling between acid chloride and the commercially available chiral auxiliary (S)-(−)-4-isopropyl-2-oxazolidinone gave the imide 31.[84] Enolization of imide 31 using sodium hexamethyldisilazane (NaHMDS) in THF at −78° C., followed by reaction with excess methyl iodide gave the stereoselectively alkylated product 32 (11:1 ratio of diastereomers by $^1$H NMR spectroscopy of the crude product). The diastereoselectivity was attributed to the formation of the Z-enolate of imide 31 followed by alkylation from the side opposite to the bulky isopropyl group (FIG. 6).

Reductive removal of the chiral auxiliary in 32 using $LiAlH_4$ gave alcohol 34 in 89% yield. While this approach gave the desired product, it was accompanied by loss of most of the chiral ligand. In an alternative procedure, hydrolysis of 32 using LiOOH gave the carboxylic acid 33 along with 98% recovery of the chiral ligand.[85] $LiAlH_4$ reduction of acid 33 gave the alcohol 34 in 92% yield over two steps. This approach furnished the alcohol 34 in 71% overall yield and proved to be superior to what was reported earlier for the same fragment.86 Dess-Martin periodinane oxidation of alcohol 34 gave the key aldehyde intermediate 25.

Synthesis of Ketone 26

The ketone 26 was synthesized as reported earlier (FIG. 7).[86,87] The ketoaldehyde 38 was synthesized by addition of propionyl chloride to the 1-N-morpholinoisobutene 37, which was prepared from condensation between isobutyraldehyde 35 and morpholine 36.[88] The enantiomerically enriched alcohol derivative 39 was prepared by Brown's allylation of aldehyde 38 using (+)-allyldiisopinocampheylborane (+)-Ipc$_2$B-(allyl) in ether at −100° C.[73] The stereochemistry of the chiral center in 39 was determined and confirmed to be (S) using Mosher ester analysis.[77] Protection of the hydroxyl group of 39 using tert-butyldimethylsilyl trifluoromethanesulfonate (TBSOTf) and 2,6-lutidine gave the ketone 26 in 96% yield.

Coupling Between Fragments 25 and 26

Figure 8:
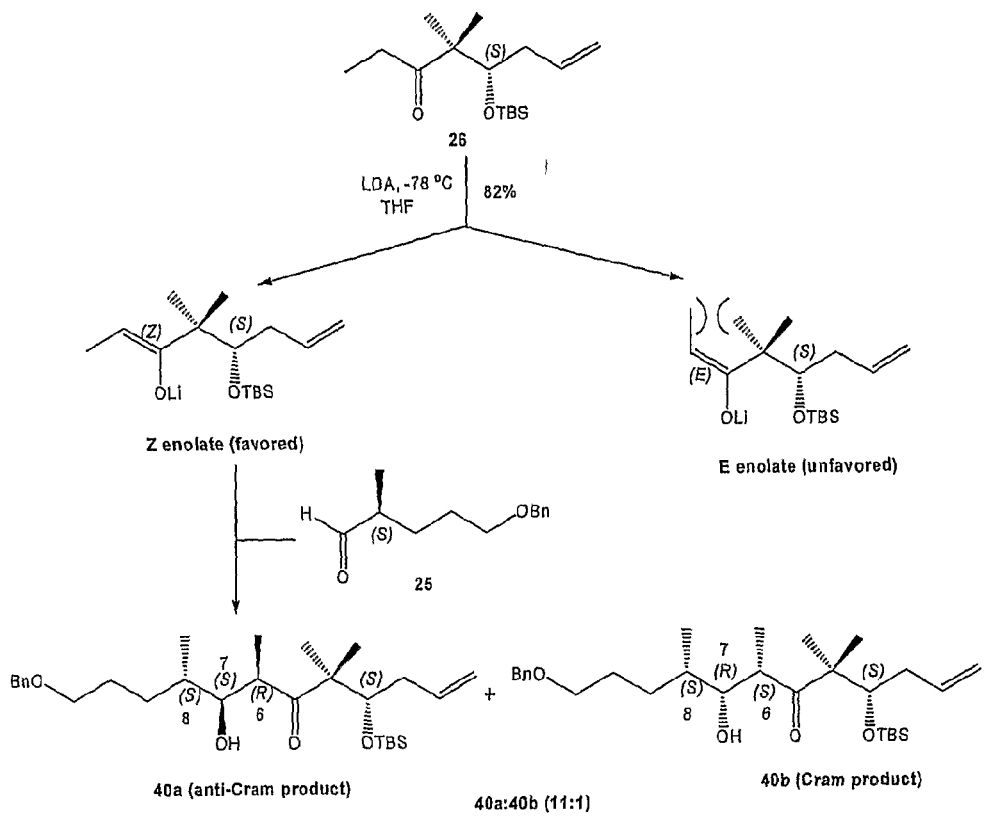

Having already made the aldehyde 25 and ketone 26, the important diastereoselective aldol reaction to construct the C6-C7 bond and establish the absolute stereochemistry at these two positions was performed (FIG. 8). Ketone-derived lithium enolate aldol reactions have a highly reversible nature.[89] The retro-aldol reaction can cause scrambling of enolate geometry which will affect the stereochemical outcome of the product. Nicolaou et al. overcame this problem by using a large excess of the ketone enolate (2.3 equivalents) which ensured that the initially formed Z-enolate remained predominant in the course of the reaction.[90] The Z-enolate of ketone 26 (2.3 equivalents) was further favored kinetically by using a bulky base (LDA) at −78° C. The reaction time was kept as short as possible to minimize aldol equilibration. Thus, the desired syn aldol 40a was formed together with the other syn product 40b (40a: 40b, 11:1) without detectable formation of the anti product (FIG. 8). Excess ketone 26 was easily recovered and separated by flash chromatography from the syn aldol 40a. It was also possible to separate the two syn aldols 40a/40b (74% yield for 40a and 6.7% yield for 40b). The stereochemistry at the C7 was confirmed to be (S) by Mosher ester analysis.[77]

Figure 9:
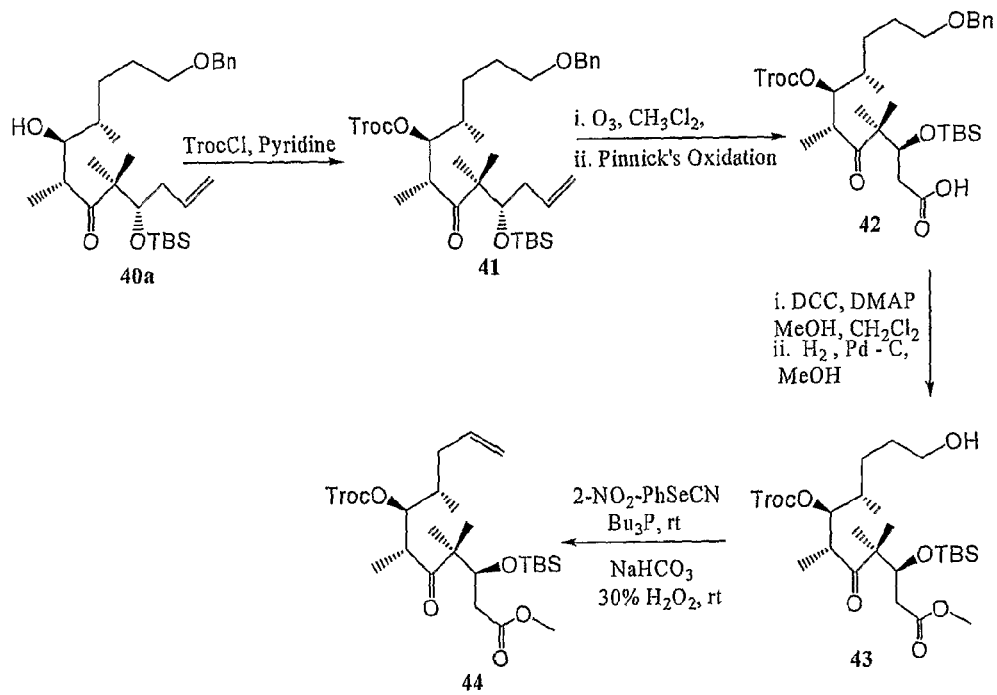
FIG. 9 shows the synthesis of 44.

Protection of the alcohol function of 40a with Troc-chloride and pyridine gave 41 (FIG. 9). Ozonolysis of 41 under reducing conditions (Ph$_3$P), followed by Pinnick oxidation gave the corresponding acid 42. 4-(Dimethylamino)pyridine (DMAP)-catalyzed esterification of 42 with dicyclohexylcarbodiimide (DCC) to give the methyl ester, followed by debenzylation furnished the key alcohol intermediate 43. Selenylation of 43 using 2-nitrophenyl selenocyanate gave the corresponding 2-nitrophenyl selenocyanate intermediate, which was subjected to in situ alkaline hydrogen peroxide oxidation and elimination to give the corresponding olefin 44.

Synthesis of Cyclic Fragment 27

The next challenge was to synthesize the aryl cyclopentenyl fragment that will be coupled to fragment 44 by Suzuki coupling reaction. The diketoesters 47a and 47b were synthesized by alkylation of the commercially available ethyl propionylacetate 45 with substituted α-bromoacetoaromatic derivatives 46a and 46b (FIG. 10). The diketoesters 47a and 47b were cyclized directly into the cyclopentenones (+/−) 48a and (+/−) 48b by an intramolecular aldol condensation reaction.

Figure 11:
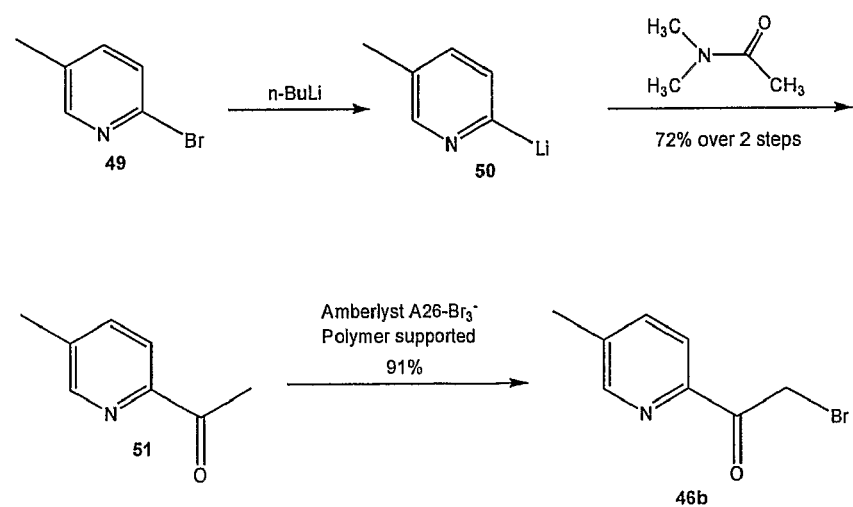
FIG. 11 shows the synthesis of 46b.

The synthesis of 2-bromo-1-(5-methylpyridin-2-yl)ethanone 46b was performed as shown in FIG. 11. The facile lithium-bromine exchange reaction was used between the commercially available 2-bromo-5-methylpyridine 49 and butyllithium at low temperature to produce the 2-lithio-methylpyridine intermediate 50, which was reacted in a one-pot reaction with N,N-dimethylacetamide to form 1-(5-methylpyridin-2-yl)ethanone (51) in 72% yield over two steps.[92a] We were able to make compound 46b by bromination of 51 using a commercially available polymer supported tribromide (Amberlyst A26-Br$_3^-$).[92b] This was a clean reaction and a simple filtration of the resin followed by flash chromatography gave the desired product 46b in 91% yield (FIG. 11).

The next step was to stereoselectively reduce the ketone group of (+/−) 48a and (+/−) 48b to the corresponding alcohols. Since 48a and 48b are racemic mixtures, non stereoselective reduction will give a mixture of four isomers (two cis and two trans). The target was to convert the racemic β-keto esters 48a and 48b to the corresponding racemic trans products, and preferably the enantiomerically pure trans-β-hydroxyesters.

Figure 12:
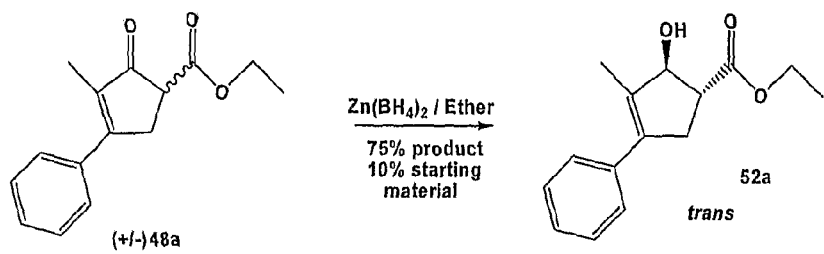
Figure 12:
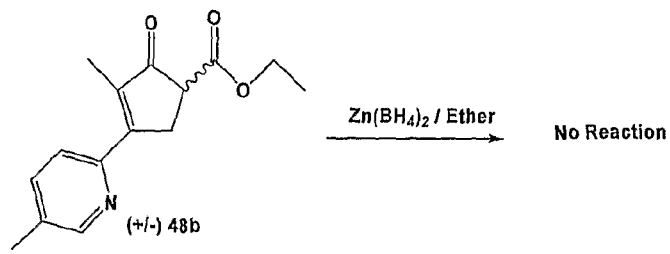
Figure 12:
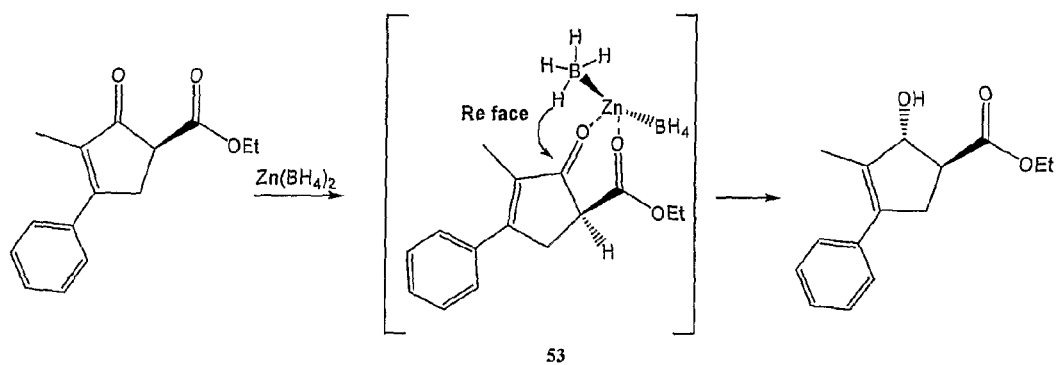

This was achieved by reduction of the racemic β-keto ester (+/−) 48a using zinc borohydride Zn(BH$_4$)$_2$ (FIG. 12)[96,97] to obtain 52a as a racemic mixture. The trans diastereoselectivity was consistent with the coordination (chelation) of the zinc with the carbonyl oxygens of both ketone and ester, forming the cyclic chelated species 53 (FIG. 12). Hydride from the borohydride is delivered to the carbonyl carbon (Re) face from the same side of the ester group.

Figure 13:
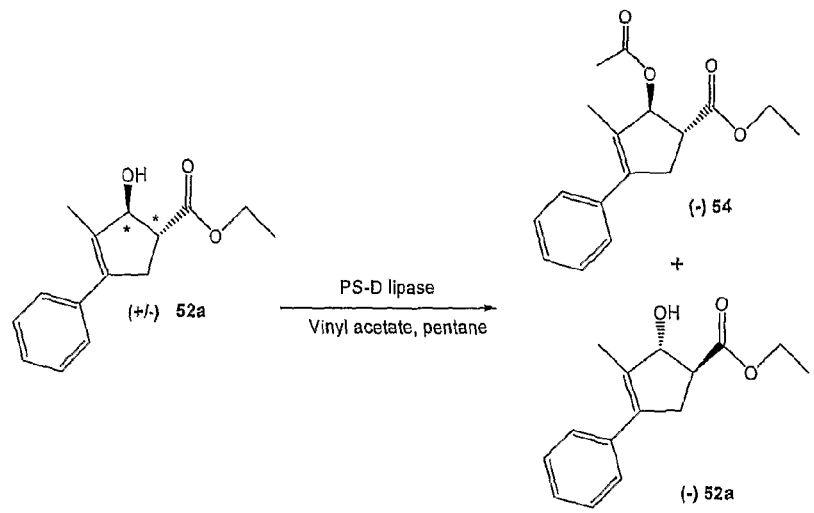
Figure 14:
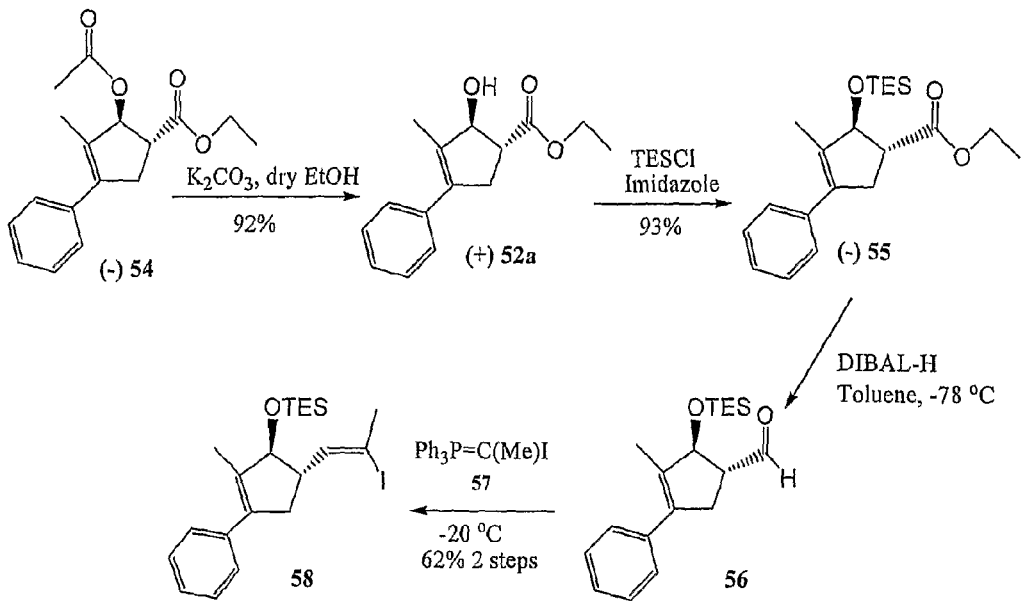
FIG. 14 shows the synthesis of 58.

The mixture of trans racemate (+/−)-52a was resolved by enzyme-mediated chiral resolution using Amano PSD Lipase enzyme to form the desired product in the acetylated form (compound (−) 54, FIG. 13). No hydrolysis of the ester group of (+/−) 52a was observed since the reaction was performed under anhydrous conditions. The stereochemistry at the secondary hydroxyl carbon of the other trans isomer (−) 52a and its enantiomeric purity were determined by Mosher ester analysis (R, 99% ee).[77]

Figure 15:
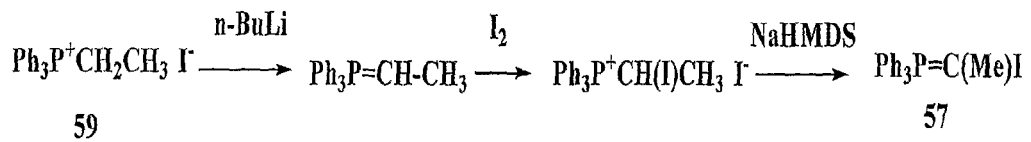
FIG. 15 shows the synthesis of α-iodoethyl ylide 57.
Figure 19:
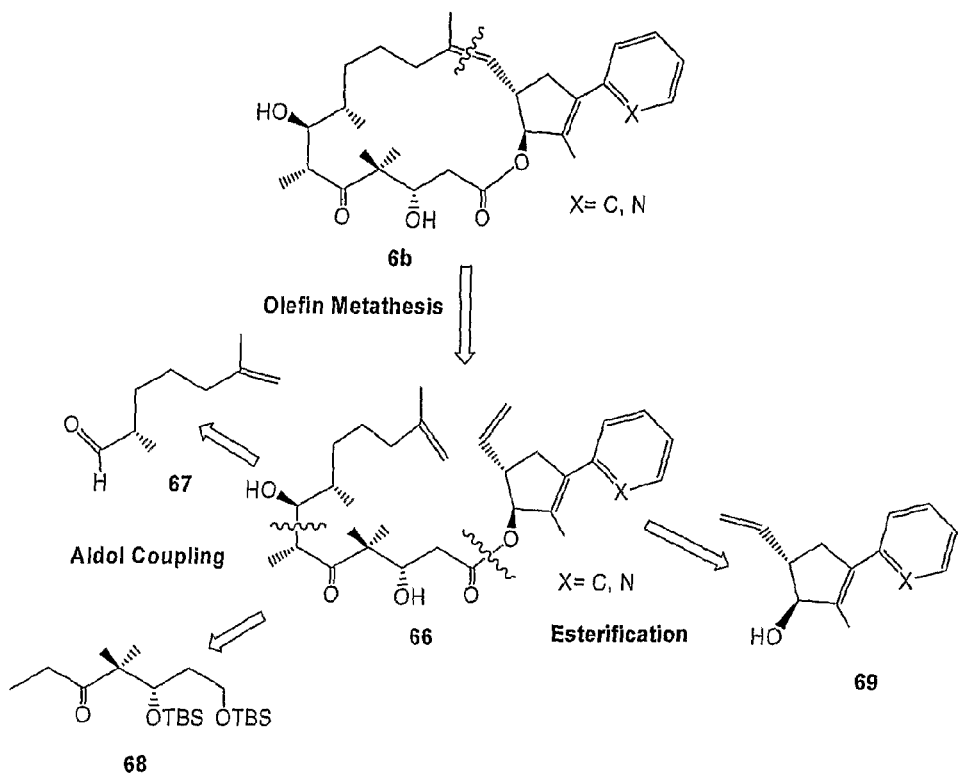
FIG. 19 shows the olefin metathesis approach.

Selective saponification of the secondary ester functionality of ester 54 gave the desired alcohol (+) 52a in 92% yield and 98% ee as determined by Mosher ester analysis.[77] Protection of the secondary hydroxyl group of (+) 52a with chlorotriethylsilane (TESCl) gave the protected cyclic ester (−) 55 in 93% yield (FIG. 19). The ester group of compound 55 was reduced using diisobutylaluminum hydride (DIBAL-H) to give the corresponding aldehyde 56, which was converted directly to the vinyl iodide 58 using the α-iodoethyl ylide 57 prepared in situ as shown in FIG. 15.[98]

Figure 16:
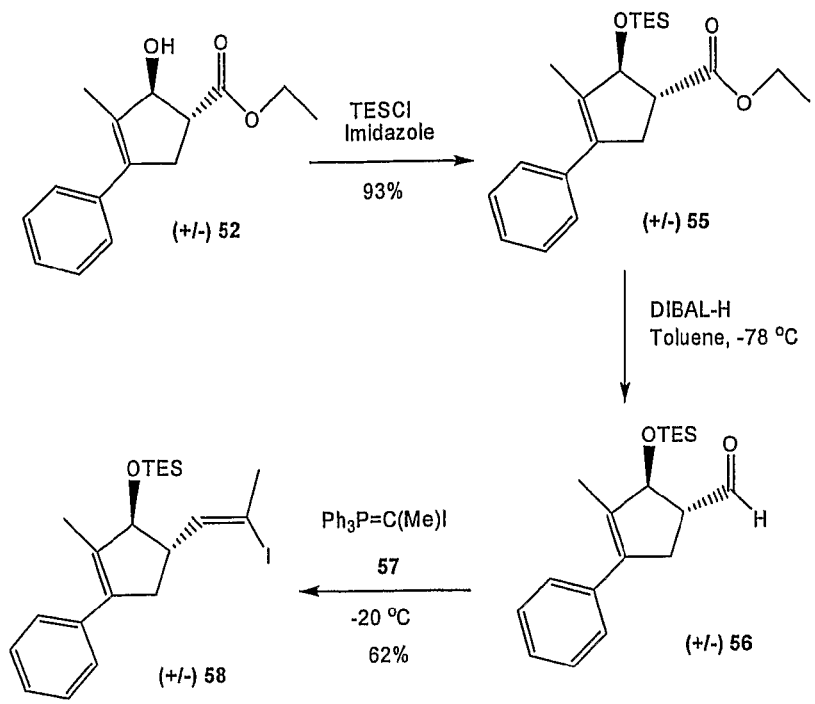
FIG. 16 shows the synthesis of (+/−) 58.

These 1-iodoalkyl ylides are reported to form mainly the (Z)-iodoalkenes upon reaction with aldehydes (>20:1, Z: E).[98] The (Z) stereochemistry at the double bond of 58 was confirmed by NOESY (2D NMR) experiment. The NMR study showed a strong NOESY interaction between the protons of the methyl group on the double bond with the vinylic proton of the (Z) configuration. This interaction would not appear in the (E) isomer. In a similar manner, the racemic mixture of vinyl iodide (+/−) 58 was made starting from the racemic trans β-hydroxy ester (+/−) 52a (FIG. 16).

Coupling Between Fragments 44 and (+/−) 58

Figure 17:
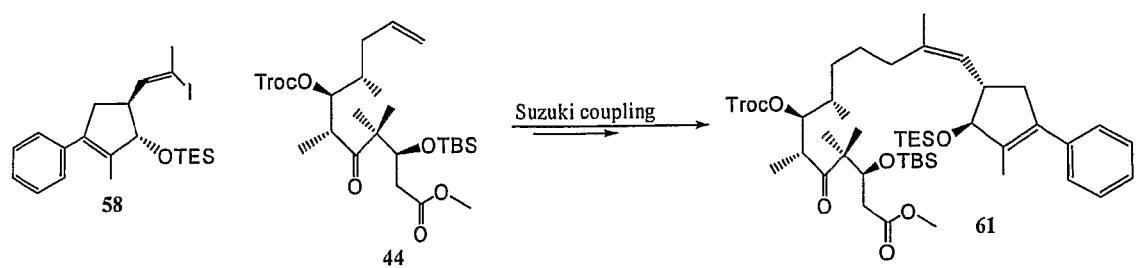
FIG. 17 shows the Zusuki coupling of 58 and 44.

Suzuki coupling reaction was the next step after making the two necessary fragments (olefin 44 and the (Z)-vinyl iodide 58). Borane-alkyl Suzuki coupling of the enantiomerically pure olefin 44 with the enantiomerically pure (Z)-vinyl iodide 58 gave the desired Z-olefin as a single isomer (FIG. 17).

Figure 18:
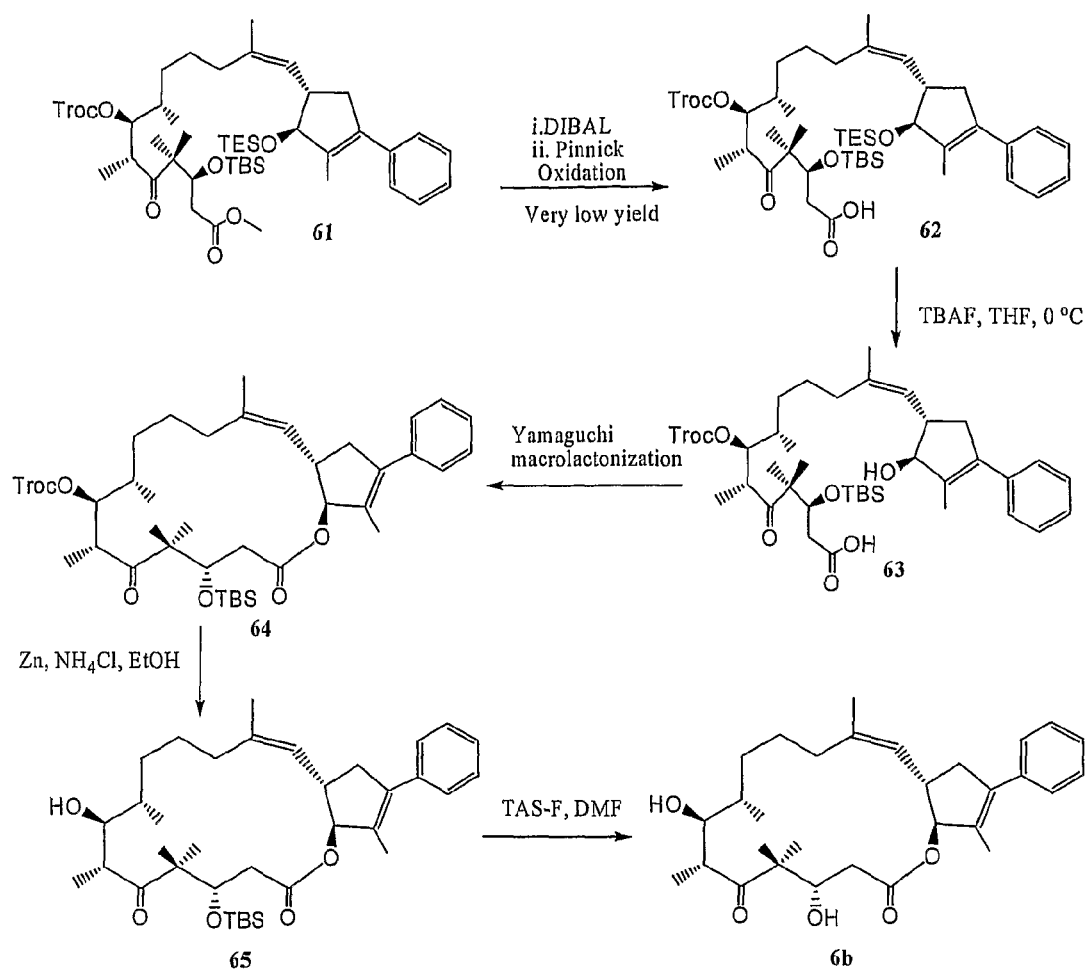
FIG. 18 shows the Troc-TBS approach (synthesis of target 6b).

The next step was the conversion of the methyl ester of 61 to the corresponding carboxylic acid 62 (FIG. 18). This was achieved by DIBAL-H reduction, followed by Pinnick's oxidation, though the yields were low. Successful Yamaguchi macrolactonization of hydroxyacid 63 furnished the macrolactone 64. Subjecting 64 to zinc dust in slightly acidic ethanol (using anhydrous ammonium chloride) removed the Troc protecting group to give compound 65. The crude product of 65 was treated with tris(dimethylamino)sulfur (trimethylsilyl)difluoride (TAS-F) in DMF to give the first target analogue 6b. TAS-F is a mild reagent that is usually used for the deprotection of silyl protecting groups in compounds that are sensitive to both acidic and basic conditions.[103] The first target molecule was synthesized, though in a low yield, due in part to the incompatibility of the Troc protecting group with the reduction step (conversion of 61 to 62 as shown in FIG. 18).

In view of the low yields obtained, at this stage, strategy was changed by proceeding with the esterification first, and then closing the macrolactone ring using olefin metathesis approach. A convergent synthetic approach was adapted as before using three key fragments 67, 68, and 69 (FIG. 19). The metathesis approach necessitated synthesis of compound 66. The aldol product, formed by coupling between aldehyde 67 and ketone 68, was converted to the corresponding carboxylic acid fragment and then coupled to alcohol 69 to give 66. This intermediate was then subjected to olefin metathesis to yield the desired product.

Synthesis of Aldehyde 67

Figure 20:
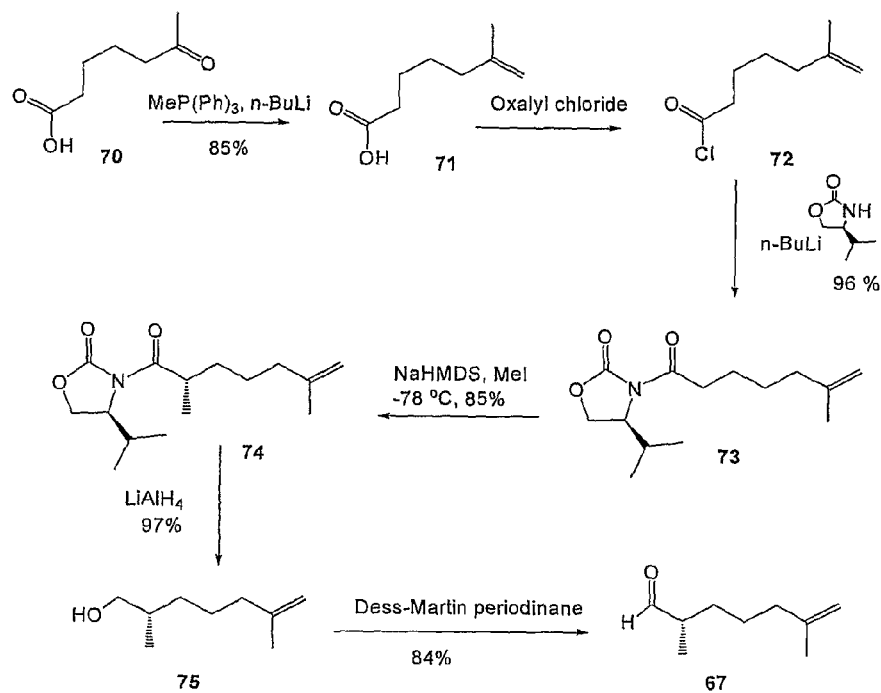
FIG. 20 shows the synthesis of 67.

Aldehyde 67 was made using the Evans asymmetric alkylation protocol 84 as described earlier for similar fragment (FIG. 20). Wittig olefination of the ketone in commercially available 6-oxoheptanoic acid 70 gave compound 71. The carboxylic acid group of 71 was then converted to the acid chloride 72 using oxalyl chloride. Coupling between 72 and the commercially available chiral auxiliary (S)-(−)-4-isopropyl-2-oxazolidinone gave the imide 73 in 81.6% yield over three steps starting form commercially available material. The method furnished imide 73 in a much simpler way and in higher yield compared to the approach reported by Schinzer et al. (39.6% yield over three steps).[104] Imide 73 was then converted to the aldehyde 67 following Schinzer's method (FIG. 20). Enolization of imide 73 using sodium hexamethyldisilazane (NaHMDS) in THF at −78° C., followed by reaction with excess methyl iodide gave the stereoselectively alkylated product 74 (10:1 ratio of diastereomers by $^1$H NMR spectroscopy of the crude product). Reductive removal of the chiral auxiliary using LiAlH$_4$ gave alcohol 75 that was subjected to Dess-Martin periodinane oxidation to give aldehyde 67 (same spectral data as reported by Schinzer).[104]

Synthesis of Ketone 68

Figure 21:
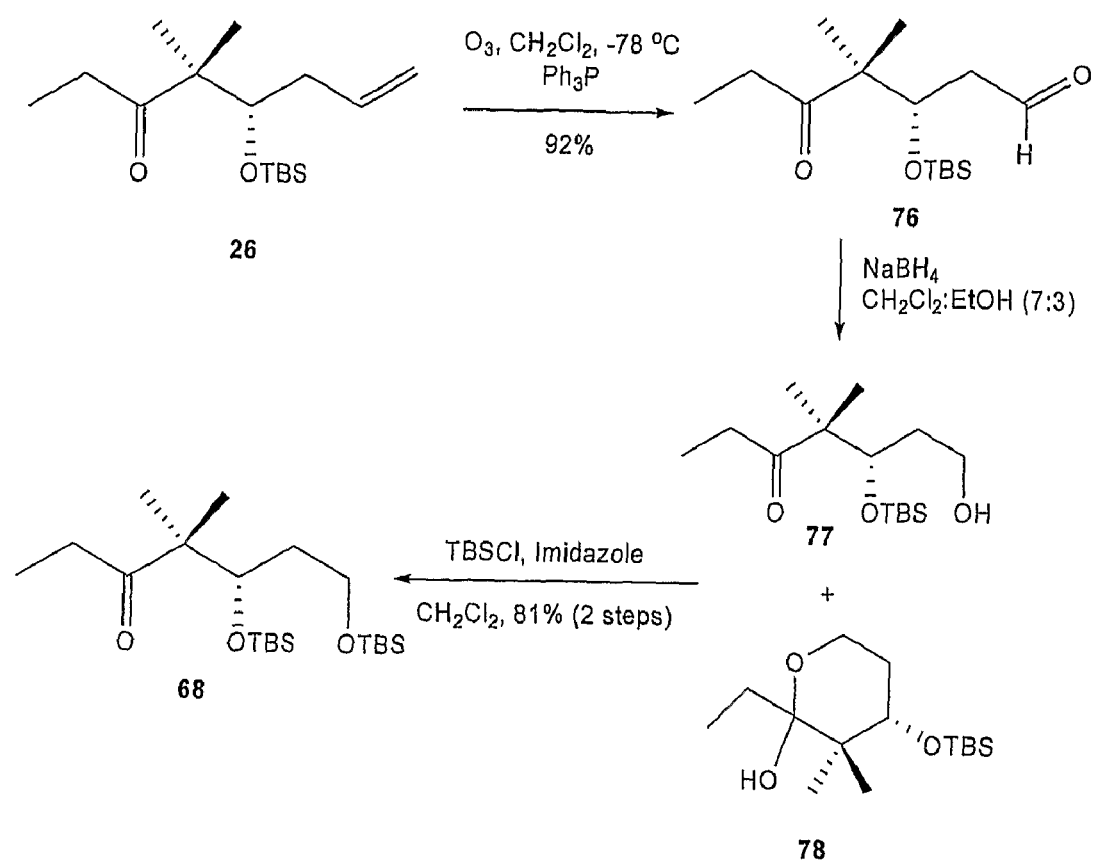
FIG. 21 shows the synthesis of 68.

The bis(silyl ether) ketone 68, with which 67 would be coupled, was made as shown in FIG. 21. Ozonolysis of the terminal double bond of compound 26 under reducing conditions (Ph$_3$P) gave aldehyde 76. Selective reduction of the aldehyde group of 76 in the presence of the ketone group was accomplished by using NaBH$_4$ in methylene chloride/methanol solution to give the primary alcohol 77 as an equilibrium mixture with its hemiacetal 78. The crude mixture was subjected to TBSCl and imidazole to give the bis-TBS ketone 68 in 81% yield over two steps.

2.3.3 Aldol Coupling Between Aldehyde 67 and Ketone 68

Figure 22:
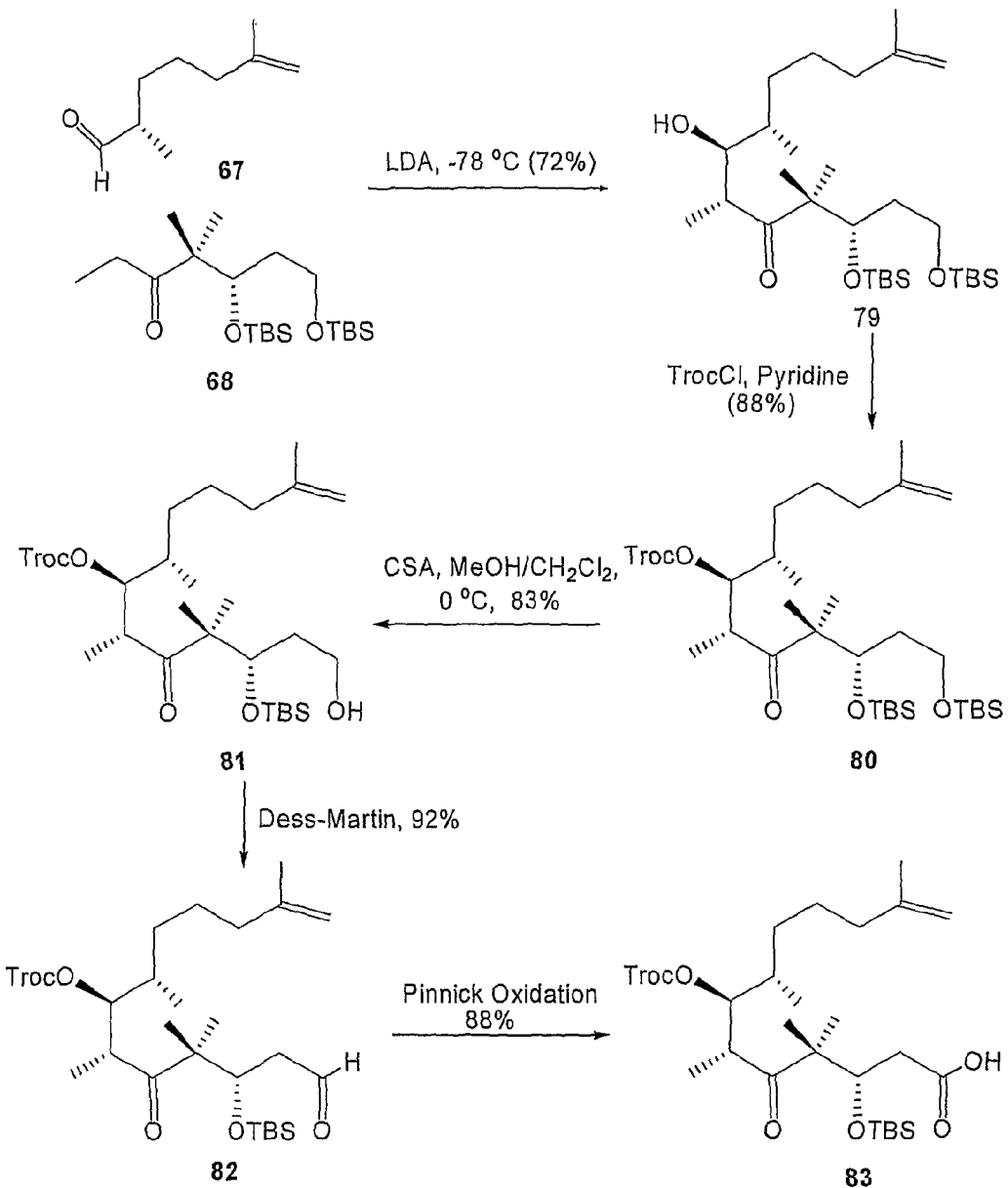
FIG. 22 shows the synthesis of 83.

Highly diastereoselective aldol reaction between the aldehyde 67 and ketone 68 under kinetic control using LDA at −78° C. generated the aldol 79 (FIG. 22). The desired syn aldol 79 was formed together with the other syn product (10:1) without any detectable formation of the anti product. The (S)-stereochemistry at the C7 position was confirmed by Mosher ester analysis.[77] The hydroxy group of aldol 79 was protected with Troc group to give compound 80. The TBS group attached to the primary hydroxyl was selectively removed using a catalytic amount of camphorsulfonic acid in methanol/methylene chloride at 0° C. to give compound 81. Oxidation of the primary hydroxyl group of 81 using Dess-Martin periodinane reagent gave the corresponding aldehyde 82. Pinnick's oxidation of aldehyde 82 gave carboxylic acid 83.

Figure 23A:
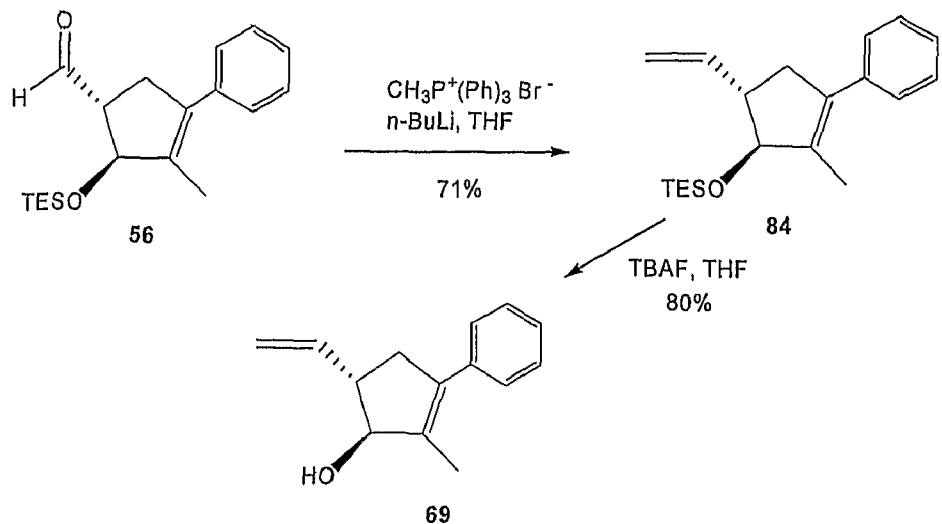
FIG. 23a shows the synthesis of 69.
Figure 23B:
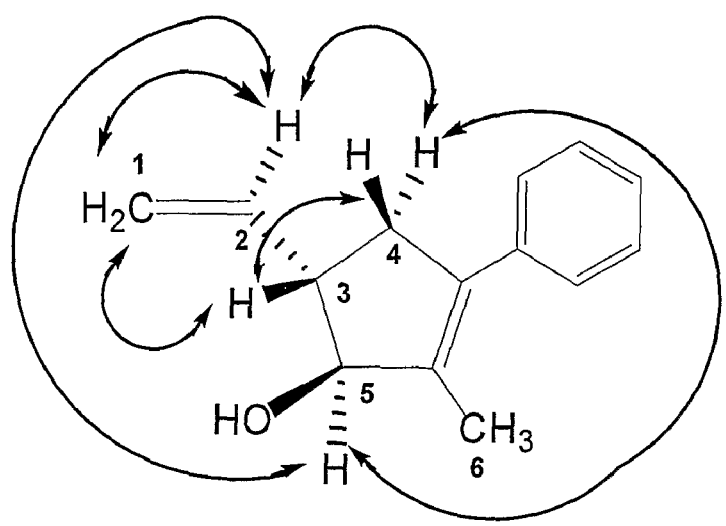
FIG. 23b shows the stereochemical assignment of (3S,5S)-2-Methyl-3-phenyl-5-vinyl-cyclopent-2-enol (69) based on NMR spectroscopy (NOESY).

The alcohol 69 was synthesized as shown in FIG. 23a. Wittig olefination of enantiomerically pure aldehyde 56 gave the corresponding olefin 84 which was treated with tetrabutylammonium fluoride (TBAF) to give the desired alcohol 69. At this stage, the relative trans stereochemistry of the protons H5 and H3 in the cyclopentene moiety were confirmed on the basis of relevant correlations observed in the NOSEY experiment. The assignment was on the basis of strong NOESY correlations observed for H2/H1, H2/H4α, H2/H5, and H3/H4α and for a little weaker correlations observed for H1/H3 and H5/4α (FIG. 29). Since the absolute stereochemistry was already assigned at the secondary hydroxyl carbon using Mosher ester analysis (see compound (+) 52a, FIG. 13), compound 69 depicted in FIG. 23b represents the absolute stereochemistry of this fragment.

Coupling Between Acid 83 and Alcohol 69

Figure 24:
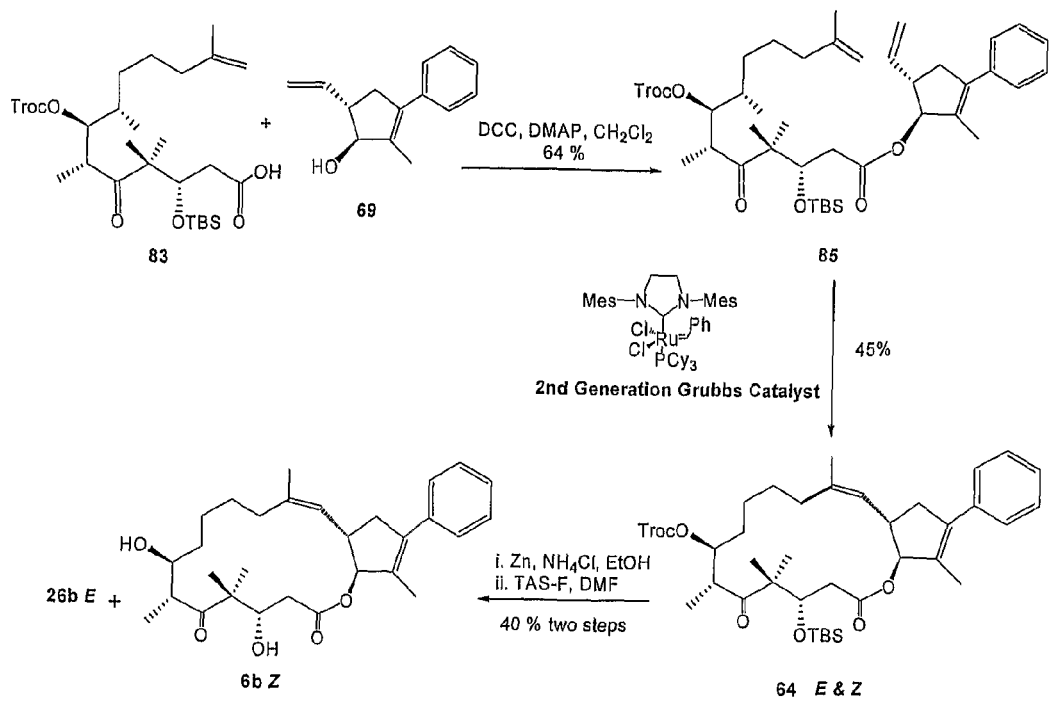
FIG. 24 shows the synthesis of 6b (first olefin metathesis approach).

The carboxylic acid 83 was coupled with alcohol 69 using DCC/DMAP in methylene chloride to give ester 85 (FIG. 24). Ring closure to form the sixteen-membered ring target molecule was then achieved by an intramolecular olefin metathesis approach using a second generation Grubb's catalyst (0.2 equivalents) under reflux for 7 hours to obtain the macrolactone 64 as a mixture of E:Z isomers. The crude mixture of 86 was purified by flash column chromatography. It was difficult to remove traces of the catalyst form the metathesis product 64; therefore, this material was used directly in the next step. Treating the macrolactone 64 mixture with zinc dust and ammonium chloride in dry ethanol removed the Troc protecting group. The crude product was treated with TAS-F in DMF to give the first target analogue 6b in 40% yield over two steps from 85. The E and Z isomers were separated by preparative TLC. The stereochemistry of the formed double bond in the two isomers was determined by a NOESY experiment.

Figure 25:
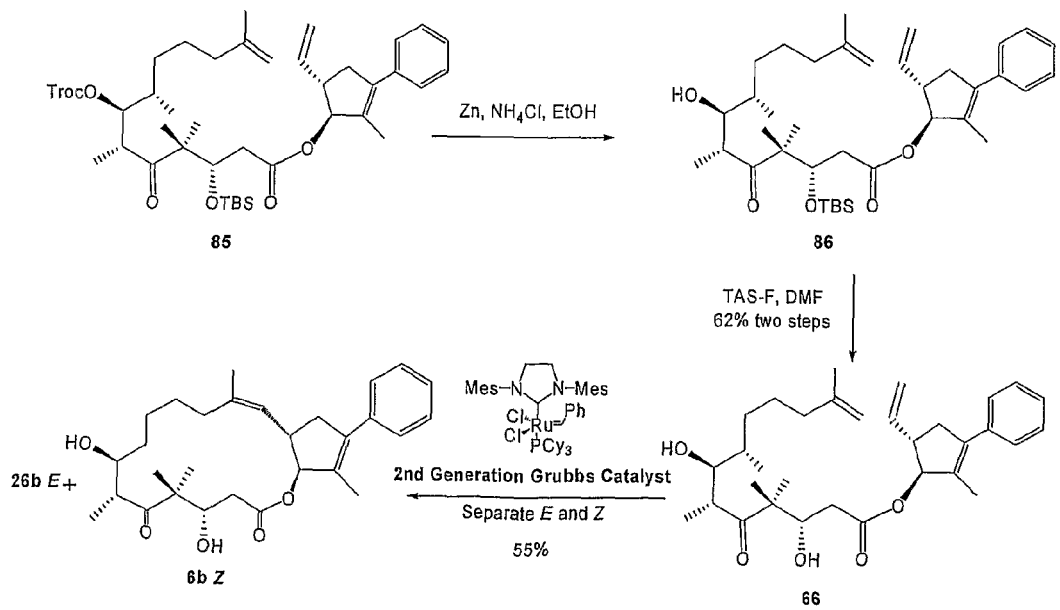
FIG. 25 shows the synthesis of 6b (final olefin metathesis approach).
Figure 26:
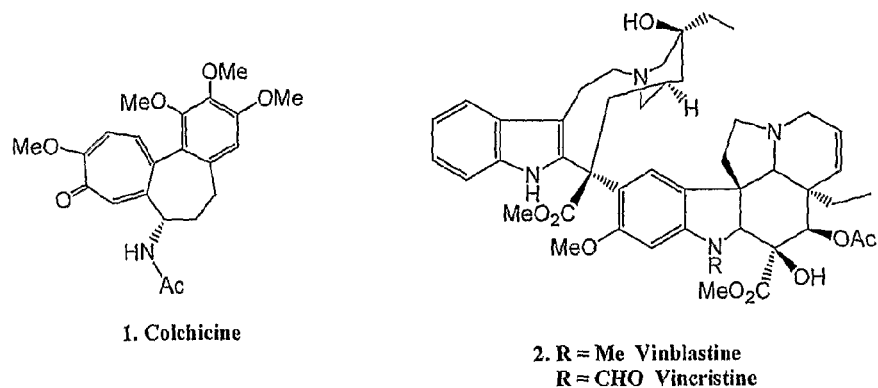
FIG. 26 shows antimitotic agents.
Figure 26:
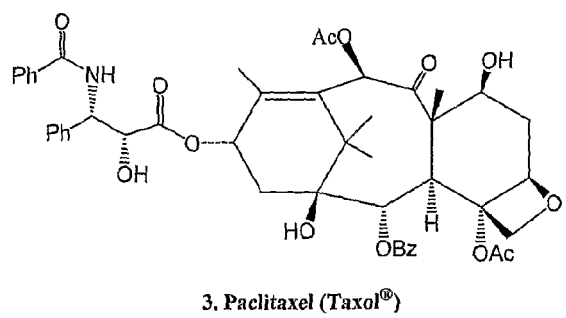
Figure 27:
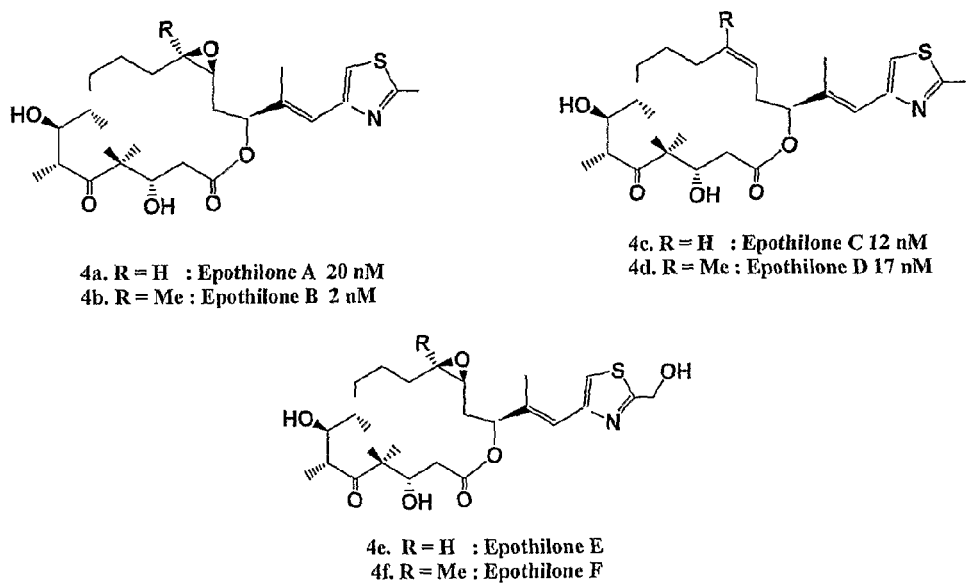
FIG. 27 shows naturally occurring epothilones.
Figure 28:
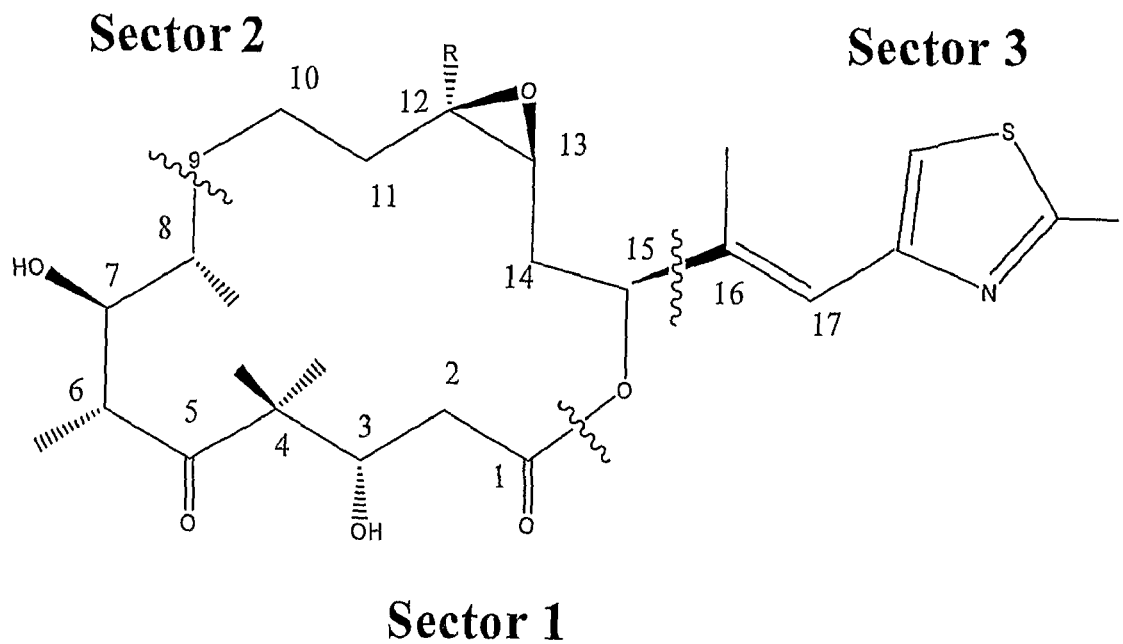
FIG. 28 shows arbitrarily defined sectors of epothilone for definition of SAR.

The low yield of the last two deprotection steps was attributed to the instability of the olefin metathesis product 64. These last few steps were therefore modified, where the full deprotection was performed before metathesis (FIG. 25). Treating compound 85 with zinc dust and ammonium chloride in dry ethanol resulted in the removal of the Troc protecting group to give 86 that was then treated directly with TAS-F to give intermediate 66 in 69% yield over two steps. Finally, ring closure of 66 using the second generation Grubb's catalyst gave the desired target molecule 6b as a Z/E mixture. The Z/E isomers were separated by preparative TLC. The formation of desired Z isomer was slightly more favored over the E isomer.

Three novel conformationally restrained epothilones 5a, 5b and 6b were synthesized. The results of these methodologies help establish whether the conformational relationship of the aromatic side chain to the macrolactone ring contributes to the bioactivity of the epothilone molecule and offers an opportunity to synthesize active epothilone analogues.

Stereoselective Reduction of the Ketone Group of (+/−) 87

Figure 31:
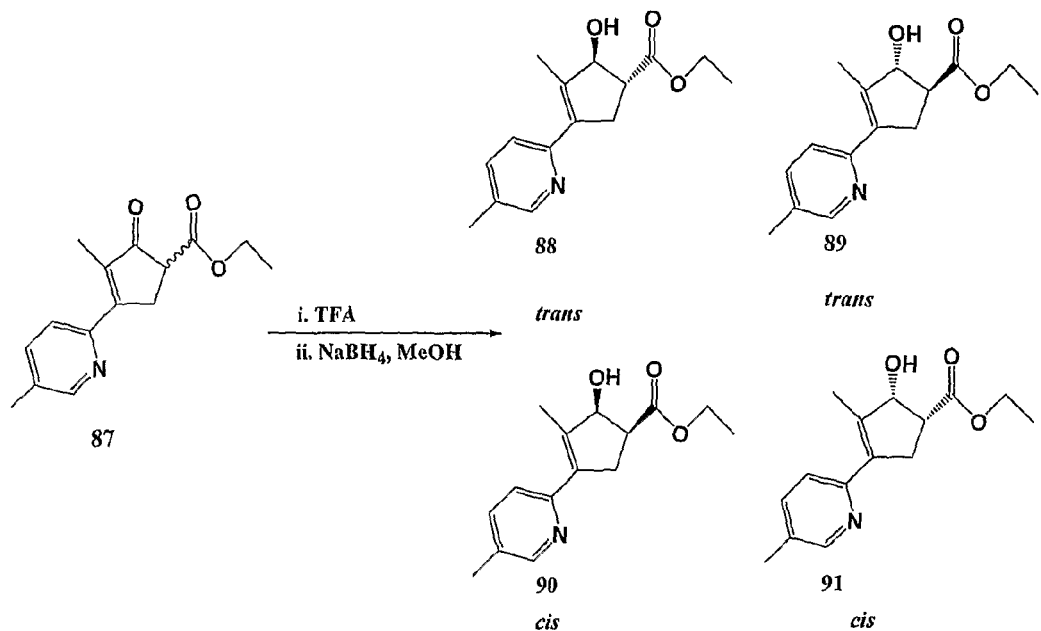
FIG. 31 shows the nonstereoselective reduction of 88/89 and 90/91.

The next step was to stereoselectively reduce the ketone group of (+/−) 87 to the corresponding alcohol. 87 is a racemic mixture. Therefore, a non stereoselective reduction gives a mixture of four isomers (two cis and two trans) (FIG. 31). The racemic beta-keto esters 87 are then converted to the corresponding enantiomerically pure trans-beta-hydroxyesters 88 or to the racemic trans products.

Different conditions for stereoselective reduction were attempted without success. Zinc borohydride Zn(BH$_4$)$_2$ which gave trans diastereoselectivity in the synthesis of phenyl analogue failed in the case of the pyridine analogue (+/−) 87, which may be due to the coordination of the zinc ion with the pyridine nitrogen. Surprisingly, treating (+/−) 87 with excess of sodium borohydride failed to reduce it. This may have been due to the increased stabilization of the enolate because of the high electron density of the pyridine ring and hence delocalization of the negative charge through olefinic bond. This extended conjugated system may lower the electrophilicity of the carbonyl carbon making it resistant to reduction. To remove this extended conjugation, the beta-keto ester (+/−) 87 was treated with trifluoroacetic acid to convert it to the corresponding salt. Treatment of this trifluoroacetate salt with sodium borohydride rapidly reduced the β-keto ester (+/−) 87 to a mixture of all the four diastereomers (FIG. 31). The cis and the trans diastereomers were separated using column chromatography.

The Trans Stereochemistry of 88/89

Figure 32:
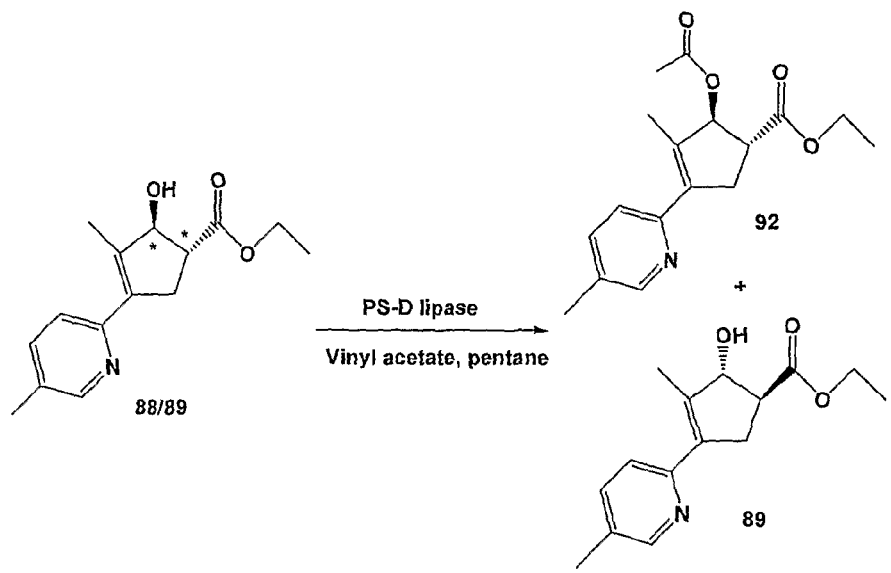
FIG. 32 shows the synthesis of 89 and 92.

The trans stereochemistry of 88/89 was confirmed by NOESY experiment. The trans mixture 88/89 was subjected to enzyme mediated chiral resolution using Amano PSD Lipase enzyme and vinyl acetate in pentane as for phenyl analogue (FIG. 32). The desired enantiomer 88 was acetylated to give compound 92 while the other trans enantiomer 89 remains unchanged.

Synthesis of Alcohol 96

Figure 33:
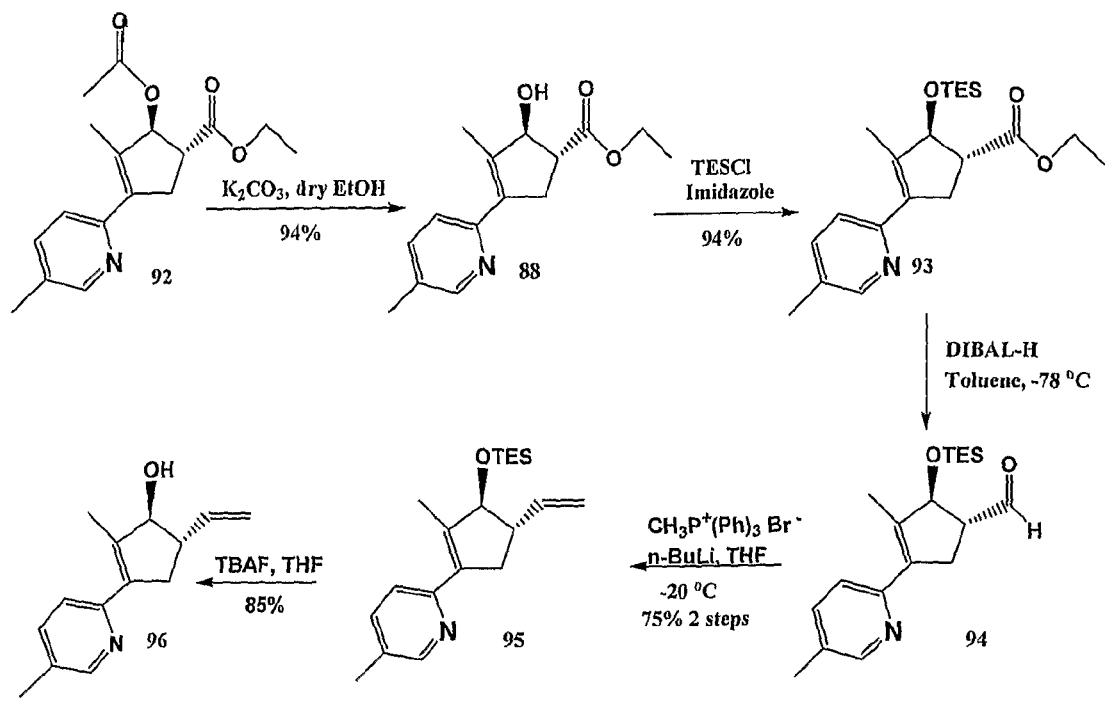
FIG. 33 shows the synthesis of 96.
Figure 34:
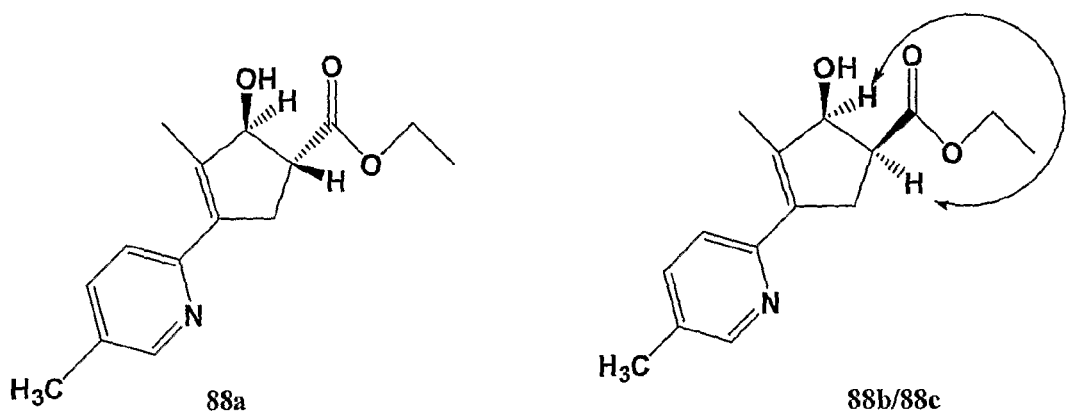
FIG. 34 shows compounds 23 and 25/26.

Saponification of the secondary ester functionality of ester 92 gave the desired alcohol 88 in 94% yield and 95% ee as determined by Mosher ester analysis (FIG. 33).[56-57] The NOESY experiment was performed to confirm the trans configuration of 88. The cis isomer 90/91 showed a strong NOE between the two protons at the two stereogenic centers and no such NOE was observed between the two corresponding protons in 88a and 88b/88c (FIG. 34). Protection of the secondary hydroxyl group of 88 with chlorotriethylsilane (TESCl) gave 93 in 94% yield (FIG. 33). Reduction of the ester group of compound 93 using diisobutylaluminum hydride (DIBAL-H) gave the corresponding aldehyde 94. Wittig olefination of enantiomerically pure aldehyde 94 using methyl triphenylphosphonium bromide and n-butyl lithium gave the corresponding olefin 95. Deprotection of 95 using tetrabutylammonium fluoride (TBAF) gave the desired alcohol 96.

Coupling Between Acid 83 and Alcohol 96

Figure 35:
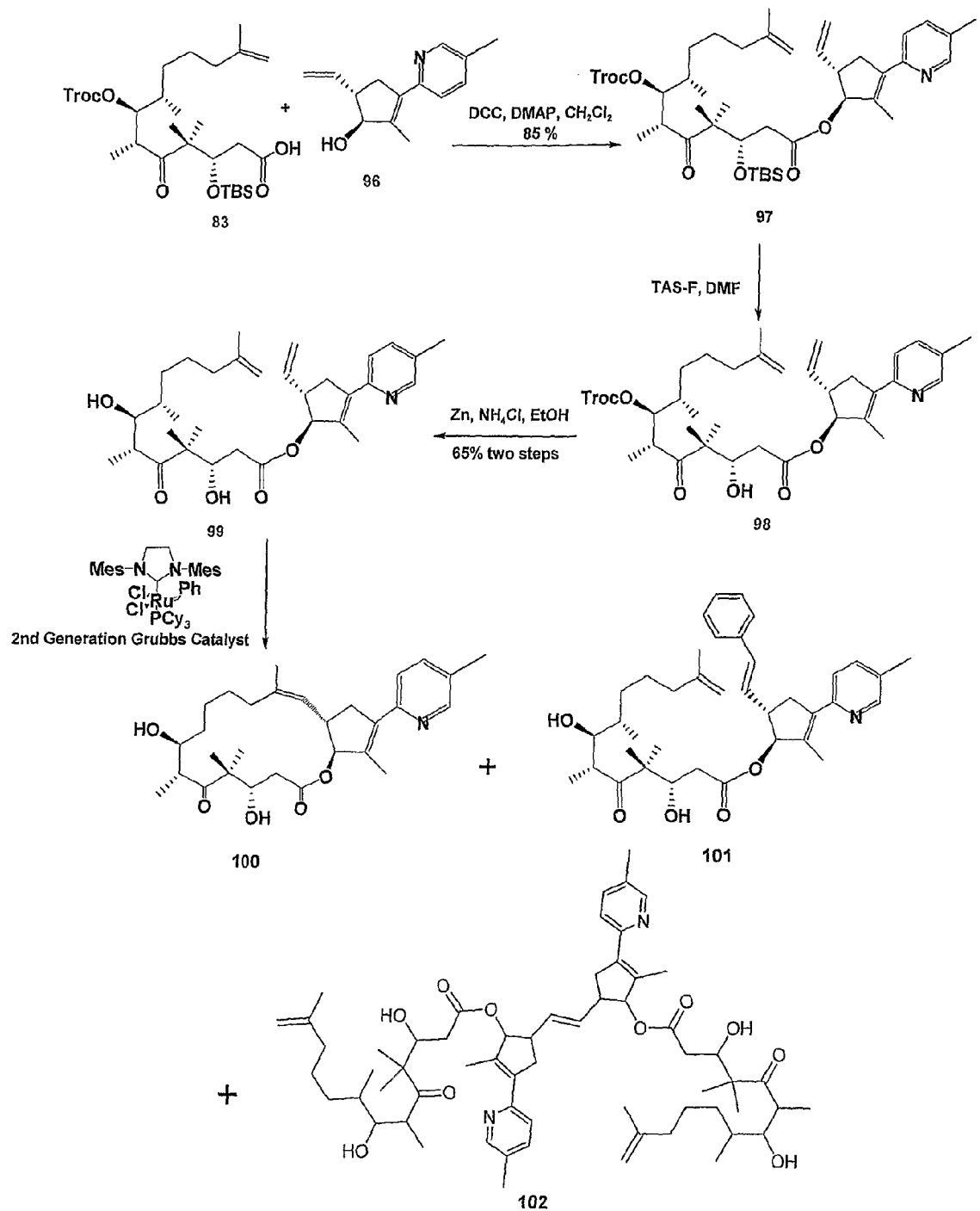
FIG. 35 shows the synthesis of 100, 101 and 102.

The carboxylic acid 83 was coupled with alcohol 96 using DCC/DMAP in methylene chloride to give ester 97 (FIG. 35). The TBS protecting group was removed by treating 97 with TAS-F to give 98 which was then treated directly with zinc dust and ammonium chloride in dry ethanol to give intermediate 99 in 67% yield over two steps. Finally, ring closure of 99 using the second generation Grubb's catalyst gave the desired target molecule 100 (The Z configuration of the double bond was confirmed by NOESY) along with the phenyl analogue 101 and the dimer 102.

EXAMPLES

The examples below are used for a more detailed explanation, without intending that it be limited to these examples.

Materials and Methods

General Techniques. All reactions were carried out under an argon or nitrogen atmosphere using dry solvents under anhydrous conditions, unless otherwise noted. Tetrahydrofuran (THF) and diethyl ether were distilled under nitrogen from sodium-benzophenone. The solvents used were ACS grade from Fisher. Yields refer to chromatographically and spectroscopically ($^1$H NMR) homogeneous materials, unless otherwise noted. Reagents were purchased from Aldrich and Across, and used without further purification. Reactions were monitored by thin-layer chromatography (TLC) carried out on 0.20 mm POLYGRAM® SIL silica gel plates (Art.-Nr. 805 023) with fluorescent indicator $UV_{254}$ using UV light and 15% sulfuric acid in ethanol solution and heat as visualizing agents. Normal phase flash column chromatography was carried out using Davisil® silica gel (100-200 mesh, Fisher). Preparative thin-layer chromatography (PTLC) separations were carried out on 1 mm, or 2 mm E. Merck silica gel plates (60F-254). NMR spectra were recorded on INOVA 600, Varian VXRS-400, or Bruker AC-F 300 MHz instruments and calibrated using residual undeuterated solvent as an internal reference. Coupling constants (J) were expressed in Hertz. Attached proton tests (APT) were performed to distinguish between different carbons in the $^{13}$C NMR spectra. The following abbreviations were used to explain the multiplicities: s=singlet, t=triplet, q=quartet, m=multiplet, and b=broad. Optical rotations were recorded on an AUTOPOL® III 589/546 polarimeter. High-resolution mass spectra (HRMS) were recorded on a Micromass LCT Electrospray mass spectrometer performed at the Mass Spectrometry & Proteomics Facility (The Ohio State University). Ozone was generated by passing 100% oxygen through commercial ozone generator (Model T-408; Welsbach Corp.). (+)Allyldiisopinocampheylborane solution in pentane was prepared by an adaptation of a procedure reported by Brown et al.[73] Allylmagnesium bromide (5.82 ml of 1 M solution in ether, 5.82 mmol) was added dropwise to a well-stirred solution of (−)-B-methoxydiisopinocampheylborane (1.92 g, 6.062 mmol) in ether (35 ml) at 0° C. After addition was complete, the reaction mixture was stirred at room temperature for 1 h, and the solvents were pumped off under reduced pressure. The residue was extracted with dry pentane (3×13 ml) under nitrogen, and the stirring was discontinued to allow the precipitation of the MgBr(OMe) salt. The clear pentane supernatant was cannulated into another flask through a filtering funnel, and used without further purification.

Jones reagent was prepared by dissolving chromium trioxide (26.72 g) in concentrated sulfuric acid (23 ml) diluted with water to a volume of 100 ml.

Zinc borohydride (0.3M solution in dry ether) was prepared by addition of saturated solution of anhydrous zinc chloride (12 g, 88.05 mmol, oven dried at 130° C. for 8 h under vacuum) in ether (50 ml) to $NaBH_4$ (8.1 g) in ether (150 ml).[96,97]

1-Pyridin-2-yl-hexane-1,4-dione (12) 76

To a solution of 2-pyridinecarboxaldehyde (11) (1 g, 9.35 mmol), ethyl vinyl ketone (0.78 g, 9.35 mmol, 1 equiv), and triethylamine (0.65 ml, 4.68 mmol, 0.5 equiv) was added 3-ethyl-5-(2-hydroxyethyl)-4-methylthiazolium bromide (0.118 g, 0.468 mmol, 0.05 equiv). After stirring the reaction mixture for 12 hours at room temperature, methylene chloride (50 ml) was added. The organic phase was washed with 1N aqueous HCl (20 ml), brine (20 ml) and then dried over anhydrous sodium sulfate. The solvents were evaporated in vacuo and the residue was subjected to flash column chromatography (EtOAc/hexanes, 1:10) to give the pure product 12 (1.214 g, 68%) as a yellow oil: TLC $R_f$=0.47 (silica gel, 33% EtOAc/hexanes); $^1$H NMR (600 MHz, $CDCl_3$) δ 8.67-8.66 (m, 1H), 8.0-7.98 (m, 1H), 7.82-7.79 (m, 1H), 7.46-7.43 (m, 1H), 3.52-3.49 (t, $^3$J=6 Hz, 2H), 2.86-2.83 (t, $^3$J=6 Hz, 2H), 2.56-2.52 (q, $^3$J=7.2 Hz, 2H), 1.09-1.06 (t, $^3$J=7.2 Hz, 3H); $^{13}$C NMR (100 MHz, $CDCl_3$) δ 210.163, 200.727, 153.441, 149.187, 137.003, 127.320, 121.952, 36.170, 32.098, 8.069; HRMS calcd for $C_{11}H_{13}NO_2+Na^+$ 214.0844; found 214.0839 [M+Na$^+$].

2-Methyl-3-pyridin-2-yl-cyclopent-2-enone (13)

A solution of the diketone 12 (1.2 g, 6.28 mmol) in dry ethanol (20 ml) was added dropwise to a solution of sodium hydroxide (0.251 g, 6.28 mmol, 1 equiv) in dry ethanol (10 ml). The solution was stirred overnight at room temperature. Saturated aqueous ammonium chloride (30 ml) was added and the mixture was concentrated in vacuo to remove most of the ethanol. The resultant crude was extracted with ethyl acetate (3×30 ml) and the combined organic extracts were dried over anhydrous sodium sulfate. The solvent was removed in vacuo to give an oil that was purified by flash column chromatography (EtOAc-hexane, 1:10) to give the cyclic ketone 13 (0.87 g, 80%) as a light brown solid: TLC $R_f$=0.55 (silica gel, 25% hexanes/EtOAc); $^1$H NMR (600 MHz, CDCl$_3$) δ 8.74-8.72 (m, 1H), 7.79-7.76 (m, 1H), 7.56-7.55 (d, $^3J$=7.8 Hz, 1H), 7.30-7.27 (m, 1H), 3.04-3.0 (m, 2H), 2.08-2.06 (m, 2H), 2.08-2.07 (m, 3H); $^{13}$C NMR (100 MHz, CDCl$_3$) δ 210.667, 164.865, 155.046, 150.082, 139.103, 136.529, 123.854, 123.577, 34.161, 28.344, 10.334; HRMS calcd for C$_{11}$H$_{11}$NO+H$^+$ 174.0919; found 174.0936 [M+H$^+$].

(1S)-2-Methyl-3-pyridin-2-yl-cyclopent-2-enol (9)

To a solution of ketone 13 (0.2 g, 1.16 mmol) in THF (2 ml) was added (R)-2-methyl-CBS-oxazaborolidine (0.35 ml of 1.0 M solution in toluene, 0.35 nmol, 0.3 equiv) at room temperature. To this solution was added borane-THF (0.755 ml of 1.0 M solution in THF, 0.755 mmol 0.65 equiv) dropwise. The reaction mixture was stirred at room temperature for 30 min after which time another portion of borane-THF (0.8 ml) was added and the mixture was stirred for an additional 3 hours. It was then cooled to 0° C. and quenched carefully by slow addition of water (2 ml). The mixture was extracted with ethyl acetate (3×4 ml). The organic extracts were dried over anhydrous sodium sulfate, filtered, and concentrated in vacuo to give a yellow color oil that was purified by flash column chromatography (EtOAc-hexanes, 1:7) to give the alcohol 9 (0.174 g, 86%) as a light yellow solid: $[α]^{22}_D$=−16.2 (c=0.9, CHCl$_3$); TLC R$_f$=0.47 (silica gel, 25% hexanes/EtOAc); $^1$H NMR (600 MHz, CDCl$_3$) δ 8.6-8.59 (d, $^3J$=4.8 Hz, 1H), 7.66-7.62 (m, 1H), 7.28-7.26 (d, $^3J$=7.8 Hz, 1H), 7.13-7.10 (m, 1H), 4.75-4.74 (m, 1H), 2.89-2.83 (m, 1H), 2.73-2.67 (m, 1H), 2.42-2.36 (m, 1H), 2.05 (s, 3H), 2.01-1.99 (d, $^3J$=7.8 Hz, 1H), 1.77-1.71 (m, 1H); $^{13}$C NMR (100 MHz, CDCl$_3$) δ 156.750, 149.405, 140.980, 137.494, 136.153, 122.930, 121.717, 82.459, 32.923, 32.771, 13.301; HRMS calcd for C$_{11}$H$_{13}$NO+H$^+$ 176.1075; found 176.1080 [M+H$^+$].

1-Chloro-3-methyl-but-2-ene (16) and 3-chloro-3-methyl-but-1-ene (17)[79]

Concentrated HCl (12.0 M) (300 ml) was added to 2-methyl-but-3-en-2-ol (15) (100 ml, 82.4 g, 0.957 mmol). The solution was stirred at room temperature for 50 min. The upper organic layer was separated after addition of water and dried over anhydrous potassium carbonate. Removal of solvent under reduced pressure gave an oily material. It was purified by fractional distillation at atmospheric pressure using a fractionating column with a nichrome wire to give a mixture of 16 and 17 (50 g, 55%) as a colorless oil: bp 111-113° C. $^1$H NMR (300 MHz, CDCl$_3$) δ 6.05-6.15 (dd, $^3J$=10.6 Hz, $^2J$=17.2 Hz, 1H, 17), 5.4-5.5 (m, 1H, 16), 5.2 (d, $^3J$=17.2 Hz, 1H, 17), 5.0 (d, $^3J$=10.6 Hz, 1H, 17), 4.0-4.1 (d, $^3J$=8.0 Hz, 2H, 16), 1.8 (s, 6H, 17), (s, 6H, 17).

4,4-Dimethyl-hex-5-en-3-one (18)[75]

Magnesium turnings (11 g, 0.452 mol) were placed in a three-necked round-bottomed flask equipped with a dropping funnel, reflux condenser, and a magnetic stirrer and charged with dry THF (50 ml) under nitrogen. A small crystal of iodine and a few drops of prenyl chloride mixture (16 and 17) were added. After stirring at room temperature for 5-10 min, during which time the iodine color disappeared, the reaction mixture was cooled to −10 to −15° C. and diluted with dry THF (30 ml). A solution of prenyl chloride mixture (16 and 17) (15.53 g, 0.15 mol) in dry THF (100 ml) was added dropwise through the dropping funnel over 1.5 h. The reaction mixture was allowed to warm to room temperature and stirred for 45 min. The resulting solution was transferred dropwise over a period of 30 min via a cannula, into a three-necked round-bottomed flask containing propionyl chloride (26.25 g, 0.3 mol) in dry THF (100 ml) maintained at −78° C. under N$_2$. The resulting mixture was allowed to warm to room temperature, stirred for two hours, and poured into water (300 ml). The upper organic layer was removed and the aqueous layer was extracted with two 50 ml portions of ether. The combined organic layers were washed with 2.0 M sodium hydroxide (500 ml) and brine (250 ml). It was dried over anhydrous sodium sulfate, and concentrated in vacuo to give an oil which was distilled at reduced pressure to give ketone 18 (11.5 g, 61%) as colorless oil: bp 72-74° C./40 Torr. $^1$H NMR (300 MHz, CDCl$_3$) δ 5.9-6.0 (dd, $^3J$=10.6 Hz, $^2J$=17.2 Hz, 1H), 5.14 (dd, $^3J$=0.7 Hz, $^2J$=17.2 Hz, 1H), 5.14 (dd, $^3J$=0.7 Hz, $^2J$=10.5 Hz, 1H), 2.45-2.55 (q, $^3J$=7.2 Hz, 2H), 1.3 (s, 6H), 0.95-1.05 (t, $^3J$=7.2 Hz, 3H). $^{13}$C NMR (75 MHz, CDCl$_3$) δ 213.784, 142.783, 113.967, 51.657, 30.542, 23.593, 8.210.

(5R*,6S)-6-Hydroxy-3,3,5,7-tetramethyl-oct-1-en-4-one [(+/−) 19a]

A solution of LDA (44 ml, 88 mmol, 1.1 equiv) in dry THF (100 ml) was cooled to −78° C. under N$_2$. To this solution was added dropwise ketone 18 (10 g, 80 mmol, 1 equiv). After stirring at −78° C. for 45 min, isobutyraldehyde (8.72 ml, 96 mmol, 1.2 equiv) was added dropwise. The reaction mixture was stirred at −78° C. for 45 min. Water was added and the lower aqueous layer was extracted with ether. The ether extract was dried over anhydrous sodium sulfate, filtered, and concentrated in vacuo. The oily crude material was distilled at reduced pressure to give compound (+/−) 19a (12.72 g, 81%) as a colorless oil: TLC R$_f$=0.78 (silica gel, 33% EtOAc/hexanes); $^1$H NMR (600 MHz, CDCl$_3$) δ $^1$H NMR (600 MHz, CDCl$_3$) δ 5.9-5.85 (dd, $^3J$=10.8 Hz, $^2J$=18 Hz, 1H), 5.22 (s, 1H), 5.2-5.19 (d, $^3J$=4.8 Hz, 1H), 3.33 (s, 1H), 3.22-3.19 (m, 2H), 1.69-1.61 (m, 1H), 1.24 (s, 3H), 1.22 (s, 3H), 1.01-0.97 (dd, $^3J$=6.6 Hz, $^2J$=13.2 Hz, 6H), 0.82-0.81 (d, $^3J$=7.2 Hz, 3H); $^{13}$C NMR (100 MHz, CDCl$_3$) δ 219.620, 141.525, 115.660, 76.934, 51.993, 40.812, 30.864, 23.430, 23.278, 19.593, 19.147, 10.842; HRMS calcd for C$_{12}$H$_{22}$O$_2$+Na$^+$ 221.1517; found 221.1517 [M+Na$^+$].

(5R$^+$,6S$^+$)-6-(tert-Butyl-dimethyl-silanyloxy)-3,3,5,7-tetramethyl-1-oct-1-en-4-one [(+/−)20]

In a three-necked round-bottomed flask equipped with a stirrer were placed tert-butyldimethylsilyl chloride (TBSCl) (25.670 g, 0.17 mol, 2 equiv) and imidazole (17.4 g, 0.255 mol, 3 eq) under N$_2$. Anhydrous DMF (50 ml) was added followed by compound (+/−) 19a (16.908 g, 0.0852, 1 equiv). The reaction mixture was stirred at 38° C. under N$_2$ for 72 h. Water (50 ml) was added and the mixture was then extracted with ether (3×80 ml). The organic extract was dried over anhydrous sodium sulfate, filtered, and concentrated in vacuo to give an oily residue that was applied to a silica gel column and eluted with (hexanes:CH$_2$Cl$_2$, 5:1) to obtain (+/−) 20 (22.64 g, 85%) as a colorless oil: TLC R$_f$=0.58 (silica gel, 25% EtOAc/hexanes); $^1$H NMR (600 MHz, CDCl$_3$) $^1$H NMR (600 MHz, CDCl$_3$) δ 5.95-5.90 (dd, $^3$J=10.2 Hz, $^2$J=17.4 Hz, 1H), 5.18-5.13 (dd, $^3$J=10.2 Hz, $^2$J=16.8 Hz, 2H), 3.74-3.71 (dd, $^3$J=1.8 Hz, $^2$J=8.4 Hz, 1H)), 3.1-3.05 (m, 1H), 1.45-1.40 (m, 1H), 1.22 (s, 3H), 1.20 (s, 3H), 1.02-1.0 (d, $^3$J=6.6 Hz, 3H), 0.89 (s, 9H), 0.88-0.86 (d, $^3$J=6.6 Hz, 3H), 0.80-0.78 (d, $^3$J=7.2 Hz, 3H), 0.04 (s, 6H); $^{13}$C NMR (100 MHz, CDCl$_3$) δ 216.604, 142.598, 114.492, 78.0, 51.754, 45.383, 33.04, 26.458, 24.135, 23.921, 21.156, 18.767, 16.948, 16.164, −3.253, −3.488; HRMS calcd for C$_{18}$H$_{36}$O$_2$Si+Na$^+$ 335.2382; found 335.2385 [M+Na$^+$].

(5R*,6S*)-5-(tert-Butyl-dimethyl-silanyloxy)-2,2,4,6-tetramethyl-3-oxo-heptanal (+/−)21

Ozonized oxygen was bubbled through a solution of (+/−) 20 (12 g, 38.462 mmol, 1 equiv) in dry CH$_2$Cl$_2$ (40 ml) at −78° C. The ozone was detected by starch-iodine paper and the reaction was monitored by TLC. The end of ozonolysis was indicated by the blue color appearance in the reaction mixture. The ozone stream was then stopped and the solution was flushed with N$_2$ for 10-15 min to remove excess ozone. Triphenylphosphine (12.1 g, 46.15 mmol, 1.2 equiv) was then added at −78° C. and the reaction mixture was allowed to reach room temperature and stirred for an additional 1 h. The solvent was removed under reduced pressure, and the mixture was purified by flash column chromatography (hexanes:CH$_2$Cl$_2$, 3:1) to give aldehyde (+/−) 21 (10.62 g, 88%) as a colorless oil: TLC R$_f$=0.67 (silica gel, 33% CH$_2$Cl$_2$/hexane); $^1$H NMR (600 MHz, CDCl$_3$) δ 9.61 (s, 1H), 3.77-3.75 (dd, $^3$J=2.4 Hz, $^2$J=7.8 Hz, 1H), 3.02-2.96 (m, 1H), 1.48-1.42 (m, 1H), 1.33 (s, 3H), 1.32 (s, 3H), 1.02-1.01 (d, $^3$J=7.2 Hz, 3H), 0.88 (s, 12H), 0.79-0.78 (d, $^3$J=7.2 Hz, 3H), 0.047 (s, 3H), 0.032 (s, 3H); $^{13}$C NMR (100 MHz, CDCl$_3$) δ 212.627, 200.773, 77.173, 61.367, 46.423, 33.468, 26.400, 26.338, 20.517, 19.956, 19.935, 18.660, 16.535, 15.595, −3.463, −3.636; HRMS calcd for C$_{17}$H$_{34}$O$_3$Si+Na$^+$ 337.2175; found 337.2171 [M+Na$^+$].

(3S*,4R*,7S)-3-(tert-Butyl-dimethyl-silanyloxy)-7-hydroxy-2,4,6,6-tetramethyl-dec-9-en-5-one (22a and 22b)

A solution of (+)-allyldiisopinocampheylborane (5.82 mmol, 1.1 equiv) in pentane (40 ml)$^{73}$ was cannulated dropwise to a solution of aldehyde (+/−) 21 (1.661 g, 5.29 mmol, 1 equiv) in ether (20 ml) at −100° C. (ether/dry ice bath). After the addition was complete, the mixture was stirred at the same temperature for 30 min before methanol (1 ml) was added. The mixture was brought to room temperature and saturated aqueous sodium bicarbonate solution (10 ml) was added, followed by H$_2$O$_2$ (4 ml of 50% solution in water). The reaction mixture was stirred at room temperature for 12 h and then extracted with ethyl acetate (3×15 ml). The combined organic extracts were washed with saturated aqueous ammonium chloride (8 ml), and dried over anhydrous sodium sulfate. The solvents were removed in vacuo and the crude oily product was subjected to flash column chromatography (5% EtOAc/hexanes) to give the inseparable diastereomeric mixture (22a and 22b) (1.205 g, 64%) as a clear oil: TLC R$_f$=0.59 (silica gel, 33% CH$_2$Cl$_2$/hexane); $^1$H NMR (600 MHz, CDCl$_3$) δ 5.9-5.8 (m, 1H), 5.13-5.08 (m, 2H), 3.79-3.72 (m, 2H), 3.12-3.08 (m, 1H), 2.24-2.2 (m, 1H), 2.04-1.99 (m, 1H), 1.52-1.48 (m, 1H), 1.21 (s, 1H), 1.17-1.15 (m, 4H), 1.11 (s, 1H), 1.08-1.05 (m, 3H), 0.9 (s, 12H), 0.85-0.83 (d, $^3$J=7.2 Hz, 3H), 0.1-0.2 (s, 6H); $^{13}$C NMR (100 MHz, CDCl$_3$) δ 220.858, 194.799, 136.265, 136.170, 117.739, 117, 471, 78.127, 78.003, 75.705, 75.503, 52.492, 52.402, 45.681, 45.499, 36.447, 36.410, 33.154, 32.915, 26.475, 22.600, 22.419, 21.416, 21.321, 19.745, 19.654, 18.805, 16.808, 16.519, 16.143, 16.048, −3.211, −3.475; HRMS calcd for C$_{20}$H$_{40}$O$_3$Si+Na$^+$ 379.2644; found 379.2631 [M+Na$^+$].

(3S*,4R*,7S)-3,7-Bis-(tert-butyl-dimethyl-silanyloxy)-2,4,6,6-tetramethyl-dec-9-en-5-one (23a and 23b)

Alcohols 22a and 22b mixture (100 mg, 0.281 mmol) was dissolved in CH$_2$Cl$_2$ (1 ml), the solution was cooled at 0° C., and 2,6-lutidine (82 μL, 0.702 mmol, 2.5 equiv) was added. After being stirred for 5 min at that temperature, tert-butyldimethylsilyltrifluoromethane sulfonate (97 μl, 0.422 mmol, 1.5 equiv) was added dropwise and the reaction mixture was stirred at 0° C. for 10 min, after which time no starting material was detected by TLC. Saturated aqueous ammonium chloride (1 ml) was added. The organic phase was separated, and the aqueous layer was extracted with ether (3×2 ml). The combined organic extracts were dried over anhydrous sodium sulfate, filtered, and the solvents were removed under reduced pressure. Purification by flash column chromatography (silica gel, hexanes/CH$_2$Cl$_2$, 4:1) gave pure 23a and 23b mixture (123 mg, 93%) as a clear oil: TLC R$_f$=0.43 (silica gel, 20% CH$_2$Cl$_2$/hexanes); $^1$H NMR (600 MHz, CDCl$_3$) δ 5.87-5.75 (m, 1H), 5.0-4.95 (m, 2H), 4.07-3.9 (two dd, 1H), 3.76-3.73 (m, 1H), 3.09-3.03 (m, 1H), 2.17-2.03 (m, 2H), 1.50-1.45 (m, 1H), 1.89-1.16 (two s, 3H), 1.05-1.02 (m, 6H), 0.92-0.82 (m, 24H), 0.06-0.007 (m, 12H); $^{13}$C NMR (75 MHz, CDCl$_3$) δ 212.290, 211.717, 137.051, 116.501, 76.806, 76.331, 75.438, 54.285, 45.989, 45.440, 39.810, 39.327, 33.291, 32.980, 26.486, 26.313, 24.946, 21.442, 21.271, 19.532, 18.821, 18.572, 16.316, 16.123, 15.994, 0.205, −3.236, −3.487, −3.758; HRMS calcd for C$_{26}$H$_{54}$O$_3$Si$_2$+Na$^+$ 493.3509; found 493.3546 [M+Na$^+$].

(3S,6R*,7S*)-3,7-Bis-(tert-butyl-dimethyl-silanyloxy)-4,4,6,8-tetramethyl-5-oxo-nonanal (24a and 24b)

Ozonized oxygen was bubbled through a solution of 23a/23b mixture (769 mg, 1.69 mmol) in dry CH$_2$Cl$_2$ (4 ml) previously cooled at −78° C. until the appearance of blue color in the solution. The ozone stream was then stopped and the solution was flushed with N$_2$ gas for 10 min after which time triphenylphosphine (516 mg, 1.2 eq) was added. The cooling bath was removed and the reaction mixture was allowed to reach room temperature and stirred for an additional 1 h. The solvent was removed under reduced pressure, and the mixture was purified by flash column chromatography (silica gel, hexanes/CH$_2$Cl$_2$, 5:1) to give a mixture of the two aldehyde diastereomers 24a and 24b (710 mg, 92%) as a colorless oil: TLC R$_f$=0.76 (33% CH$_2$Cl$_2$/hexanes); $^1$H NMR (600 MHz, CDCl$_3$) δ 9.8-9.74 (two dd, 1H), 4.60-4.47 (two m, 1H), 3.73-3.70 (m, 1H), 3.09-3.03 (m, 1H), 2.52-2.37 (m, 2H), 1.45-1.40 (m, 1H), 1.22-1.19 (two s, 3H), 1.10-1.0 (m, 6H), 0.90-0.84 (m, 24H), 0.08-0.01 (m, 12H); $^{13}$C NMR (100 MHz, CDCl$_3$) δ 218.931, 218.229, 201.623, 201.416, 194.799, 134.061, 128.751, 128.681, 125.525, 77.887, 71.311, 70.502, 53.969, 53.813, 49.798, 49.295, 46.060, 45.595, 33.307, 32.932, 26.470, 26.161, 26.128, 24.131, 22.782, 21.495, 21.325, 19.485, 18.809, 18.359, 18.334, 16.638, 16.086, 15.900, 0.226, −3.446, −3.847, −3.946, −4.177, −4.259; HRMS calcd for C$_{25}$H$_{52}$O$_4$Si$_2$+Na$^+$ 495.3302; found 495.3303 [M+Na$^+$].

(3S,6R,7S*)-3,7-Bis-(tert-butyl-dimethyl-silanyloxy)-4,4,6,8-tetramethyl-5-oxo-nonanoic acid (7a and 7b)

Aldehyde 24a/24b mixture (830 mg, 1.76 mmol), t-butanol (37 ml), and 2-methyl-2-butene (8.9 ml) were mixed together. A solution of sodium chlorite (1.46 g, 9.17 equiv) and sodium dihydrogen phosphate (1.46 g, 6.92 equiv) in water (10 ml) was added to the aldehyde mixture dropwise. The reaction mixture was stirred at room temperature for 30 min after which time it was concentrated under reduced pressure. The residue was subjected to flash column chromatography (silica gel, hexanes/methylene chloride, 3:1) to give the first carboxylic acid diastereomer (310 mg), followed by a mixture of the two acid diastereomers (171 mg), and finally the second acid diastereomer (282 mg) (763 mg, 89% overall yield) as colorless sticky liquids:

data for the first (higher Rf) acid 7a: $[\alpha]^{22}_D$=+6.91 (c=0.6, CHCl$_3$); TLC $R_f$=0.70 (33% EtOAc/hexanes); $^1$H NMR (600 MHz, CDCl$_3$) δ 4.52-4.50 (dd, $^3J$=3 Hz, $^2J$=6.6 Hz, 1H), 3.74-3.72 (dd, $^3J$=1.8 Hz, $^2J$=7.8 Hz, 1H), 3.08-3.03 (m, 1H), 2.47-2.43 (dd, $^3J$=3.6 Hz, $^2J$=16.8 Hz, 1H), 2.34-2.30 (dd, $^3J$=7.2 Hz, $^2J$=16.8 Hz, 1H), 1.45-1.40 (m, 1H), 1.19 (s, 3H), 1.03-1.02 (m, 6H), 0.90-0.88 (m, 12H), 0.84-0.82 (m, 12H), 0.04-0.03 (m, 12H); $^{13}$C NMR (100 MHz, CDCl$_3$) δ 217.821, 178.328, 78.019, 72.367, 54.097, 45.511, 40.007, 33.229, 26.475, 26.223, 22.336, 21.363, 19.300, 18.796, 18.400, 16.511, 16.090, −3.207, −3.479, −4.201, −4.321; HRMS calcd for C$_{25}$H$_{52}$O$_5$Si$_2$+Na$^+$ 511.3251; found 511.3251 [M+Na$^+$].

data for the second (lower Rf) acid 7b: $[\alpha]^{22}_D$=−10.72 (c=0.6, CHCl$_3$); TLC $R_f$=0.68 (33% EtOAc/hexanes); $^1$H NMR (600 MHz, CDCl$_3$) δ 4.4-4.38 (dd, $^3J$=3 Hz, $^2J$=6.6 Hz, 1H), 3.74-3.72 (dd, $^3J$=1.8 Hz, $^2J$=7.8 Hz, 1H), 3.1-3.05 (m, 1H), 2.47-2.44 (dd, $^3J$=3 Hz, $^2J$=16.2 Hz, 1H), 2.31-2.27 (dd, $^3J$=6.6 Hz, $^2J$=16.2 Hz, 1H), 1.46-1.41 (m, 11H), 1.2 (s, 3H), 1.09 (s, 3H), 10.4-1.02 (m, 3H), 0.92-0.83 (m, 24H), 0.04-0.03 (m, 12H); $^{13}$C NMR (100 MHz, CDCl$_3$) δ 218.642, 178.113, 77.896, 73.431, 53.854, 46.089, 40.379, 32.960, 26.483, 26.223, 23.764, 21.523, 19.023, 18.809, 18.417, 16.193, 15.904, −3.149, −3.455, −4.053, −4.416; HRMS calcd for C$_{25}$H$_{52}$O$_5$Si$_2$+Na$^+$ 511.3251; found 511.3247 [M+Na$^+$].

(3S,6R,7S)-3,7-Dihydroxy-4,4,6,8-tetramethyl-5-oxo-nonanoic Acid (1S,2E)-2-methyl-3-pyridin-2-yl-cyclopent-2-enyl ester (5) [Higher $R_f$ isomer]

To a solution of (higher $R_f$) carboxylic acid 7a (7.5 mg, 15.4 μmol) in methylene chloride (0.5 ml), cooled to 0° C., was added trifluoroacetic acid (75 μl) and the mixture was stirred at 4° C. for 12 h. The mixture was cooled back to 0° C. and pyridine (80 μl) was added dropwise. The solvents were removed in vacuo and the oily residue was passed through a plug of silica gel using (ethyl acetate/hexanes, 1:1) to give the fully deprotected acid 8 that was used directly in the next step. To a solution of acid 8 (ca 15.4 μmol) in methylene chloride (0.4 ml) was added a solution of alcohol 9 (3.5 mg, 20 15.4 μmol mol, 1.3 equiv) in methylene chloride (0.5 ml) and DMAP (0.5 mg, 4 15.4 μmol, 0.26 equiv). The reaction mixture was cooled to 0° C. and DCC (20 μl of 1.0 M solution in methylene chloride, 20 μmol, 1.3 equiv) was added. The mixture was stirred at 0° C. for 20 min and at room temperature overnight. The white precipitate formed was removed by filtration and the filtrate was evaporated to dryness. The residue was then passed over flash column chromatography (20% EtOAc/hexanes) to give the target ester 5a (4 mg, 64% yield over two steps): $[\alpha]^{22}_D$=−25.2 (c=0.25, CHCl$_3$); TLC $R_f$=0.25 (silica gel, 50% EtOAc/hexanes); $^1$H NMR (600 MHz, CDCl$_3$) δ 8.63-8.61 (d, $^3J$=4.2 Hz, 1H), 7.68-7.65 (m, 1H), 7.31-7.29 (d, $^3J$=7.8 Hz, 1H), 7.16-7.14 (dd, $^3J$=4.8 Hz, $^2J$=7.8 Hz, 1H), 5.83 (m, 1H), 4.27-4.24 (m, 1H), 3.36-3.32 (m, 2H), 3.27-3.23 (m, 2H), 2.96-2.91 (m, 1H), 2.80-2.75 (m, 1H), 2.52-2.38 (m, 3H), 2.0 (s, 3H), 1.87-1.82 (m, 1H), 1.71-1.65 (m, 1H), 1.17 (s, 6H), 1.06-1.04 (d, $^3J$=6.6 Hz, 3H), 1.01-1.0 (d, $^3J$=6.6 Hz, 3H), 0.87-0.85 (d, $^3J$=6.6 Hz, 3H); $^{13}$C NMR (100 MHz, CDCl$_3$) δ 222.360, 173.228, 156.073, 149.517, 140.568, 136.372, 136.223, 122.983, 122.067, 85.434, 76.645, 72.792, 52.389, 41.097, 37.123, 33.563, 30.778, 29.482, 21.660, 19.683, 19.316, 19.213, 13.519, 10.623; HRMS calcd for C$_{24}$H$_{35}$NO$_5$+Na$^+$ 440.2413; found 440.2396 [M+Na$^+$].

(3S,6S,7R)-3,7-Dihydroxy-4,4,6,8-tetramethyl-5-oxo-nonanoic Acid (1S,2E)-2-methyl-3-pyridin-2-yl-cyclopent-2-enyl ester (5) [Lower $R_f$ Isomer]

To a solution of (lower $R_f$) carboxylic acid 7b (10 mg, 20.5 μmol) in methylene chloride (0.5 ml), cooled to 0° C., was added trifluoroacetic acid (75 μl) and the mixture was stirred at 4° C. for 12 h. The mixture was cooled back to 0° C. and pyridine (80 μl) was added dropwise. The solvents were removed in vacuo and the oily residue was passed through a plug of silica gel using (ethyl acetate/hexanes, 1:1) to give the fully deprotected acid 8 that was used directly in the next step. To a solution of acid 8 (ca 20.5 μmol) in methylene chloride (0.5 ml) was added a solution of alcohol 9 (4.7 mg, 26.6 μl, 1.3 equiv) in methylene chloride (0.5 ml) and DMAP (1 mg, 8 μmol, 0.4 equiv). The reaction mixture was cooled to 0° C. and DCC (27 μl of 1.0 M solution in methylene chloride, 27 μmol, 1.3 equiv) was added. The mixture was stirred at 0° C. for 20 min and at room temperature overnight. The white precipitate formed was removed by filtration and the filtrate was evaporated to dryness. The residue was then passed over flash column chromatography (20% EtOAc/hexanes) to give the target ester 5b (5.7 mg, 68% yield over two steps: $[\alpha]^{22}_D$=−51.9 (c=0.52, CHCl$_3$); TLC $R_f$=0.25 (silica gel, 50% EtOAc/hexanes); $^1$H NMR (600 MHz, CDCl$_3$) δ 8.63-8.61 (dd, $^3J$=0.6 Hz, $^2J$=4.2 Hz, 1H), 7.68-7.65 (m, 1H), 7.31-7.29 (d, $^3J$=7.8 Hz, 1H), 7.16-7.14 (dd, $^3J$=4.8 Hz, $^2J$=7.8 Hz, 1H), 5.82 (m, 1H), 4.30-4.25 (m, 1H), 3.32 (m, 1H), 3.30-3.24 (m, 3H), 2.96-2.91 (m, 1H), 2.80-2.75 (m, 1H), 2.51-2.48 (dd, $^3J$=2.4 Hz, $^2J$=16.2 Hz, 1H), 2.47-2.42 (m, 1H), 2.42-2.38 (dd, $^3J$=10.8 Hz, $^2J$=16.2 Hz, 1H), 2.0 (s, 3H), 1.87-1.82 (m, 1H), 1.71-1.65 (m, 1H), 1.19 (s, 3H), 1.14 (s, 3H), 1.06-1.05 (d, $^3J$=6.6 Hz, 3H), 1.00-0.998 (d, $^3J$=6.6 Hz, 3H), 0.86-0.85 (d, $^3J$ 6.6 Hz, 3H); $^{13}$C NMR (100 MHz, CDCl$_3$) δ 222.331, 173.270, 156.056, 149.521, 140.584, 136.355, 136.219, 122.983, 122.067, 85.462, 76.621, 72.685, 52.257, 41.286, 36.942, 33.563, 30.815, 29.486, 21.495, 19.737, 19.205, 19.163, 13.544, 10.421; HRMS calcd for C$_{24}$H$_{35}$NO$_5$+H$^+$ 418.2593; found 418.2615 [M+H$^+$].

5-Benzyloxy-pentanoic Acid (29)

Jones reagent was added dropwise to an ice cooled solution of 5-benzyloxy-pentan-1-ol 28 (5 g, 25.74 mmol) in acetone (170 ml). Addition of the Jones reagent was stopped when the acetone solution acquired a persistent yellow color with the concurrent formation of green chlomium salts. The mixture was filtered and concentrated in vacuo to give an oily crude product that was purified by a flash chromatography (EtOAc/hexanes, 1:3) to give compound 29 (4.98 g, 93%) as a colorless oil: TLC $R_f$=0.68 (silica gel, 50% EtOAc/hexanes); $^1$H NMR (400 MHz, CDCl$_3$) δ 7.35-7.31 (m, 5H), 4.502 (s, 2H), 3.51-3.47 (t, $^3$J=6 Hz, 2H), 2.41-2.36 (t, $^3$J=6.8 Hz, 2H), 1.79-1.64 (m, 4H); $^{13}$C NMR (75 MHz, CDCl$_3$) δ 179.713, 138.651, 128.609, 127.870, 127.795, 73.158, 69.968, 33.915, 29.243, 21.749; HRMS calcd for C$_{12}$H$_{16}$O$_3$+Na$^+$ 231.0997; found 231.0992 [M+Na$^+$].

5-Benzyloxy-pentanoyl Chloride (30)

To a solution of the acid 29 (4.98 g, 24 mmol) in dry benzene (40 ml), was added oxalyl chloride (2.5 ml, 28.8 mmol, 1.2 equiv) dropwise. A drying tube was placed on the flask and the reaction was stirred for 90 min at room temperature. The reaction was concentrated in vacuo and used directly in the next step: $^1$H NMR (400 MHz, CDCl$_3$) δ 7.38-7.27 (m, 5H), 4.50 (s, 2H), 3.51-3.40 (t, $^3$J=6.4 Hz, 2H), 2.95-2.90 (t, $^3$J=7.2 Hz, 3H), 1.87-1.78 (m, 2H), 1.71-1.63 (m, 2H); $^{13}$C NMR (75 MHz, CDCl$_3$) δ 173.958, 138.519, 128.949, 128.787, 128.630, 127.862, 73.197, 69.551, 47.032, 28.618, 22.329.

3-(5-Benzyloxy-pentanoyl)-4S-isopropyl-oxazolidin-2-one (31)

To a solution of(S)-4-isopropyl-2-oxazolidonone (1.0 g, 7.74 mmol, 1 equiv) in THF (25 ml) at −78° C. was added n-butyllithium (3.1 ml of a 2.5 M solution in hexanes, 7.74 mmol, 1 equiv). After 15 min 5-(benzyloxy)-pentanoyl chloride 30 (1.924 g, 8.514 mmol, 1.1 equiv) was added and the mixture was stirred for 30 min at −78° C. and for 15 min at 0° C. Saturated aqueous ammonium chloride (7 ml) was added and the resulting slurry was concentrated under reduced pressure. The residue was diluted with ether and washed successively with saturated aqueous sodium bicarbonate and brine. The organic layer was dried over anhydrous sodium sulfate, filtered, and concentrated in vacuo. Purification by flash chromatography (10% EtOAc/hexanes) gave imide 31 (2.35 g, 95%) as a yellow oil: [α]$^{22}$$_D$=+57.6 (c=0.50, CHCl$_3$); TLC R$_f$=0.22 (silica gel, 20% EtOAc/hexanes); $^1$H NMR (400 MHz, CDCl$_3$) δ 7.35-7.30 (m, 5H), 4.50 (s, 2H), 4.45-4.39 (m, 1H), 4.26-4.17 (m, 2H), 3.53-3.48 (t, $^3$J=6.4 Hz, 2H), 3.05-2.86 (m, 2H), 2.42-2.32 (m, 1H), 1.81-1.65 (m, 4H), 0.92-0.89 (d, $^3$J=6.8 Hz, 3H), 0.88-0.85 (d, $^3$J=6.8 Hz, 3H); $^{13}$C NMR (75 MHz, CDCl$_3$) δ 173.294, 154.281, 138.798, 128.559, 127.816, 127.692, 73.086, 70.153, 63.535, 58.600, 35.436, 29.300, 28.591, 21.399, 18.173, 14.869; HRMS calcd for C$_{18}$H$_{25}$NO$_4$+Na$^+$ 342.1681; found 342.1669 [M+Na$^+$].

3-(5-Benzyloxy-2-methyl-pentanoyl)-4S-isopropyl-oxazolidin-2-one (32)

Sodium hexamethyldisilazane (6.9 ml of 1.0 M in THF, 6.9 mmol, 1.1 equiv) was added dropwise to a solution of imide 31 (2.0 g, 6.27 mmol, 1 equiv) in THF (12 ml) at −78° C. The reaction mixture was stirred for 30 min before a solution of iodomethane (1.950 ml, 31.35 mmol, 5 equiv) in THF (2 ml) was added dropwise. After stirring for 7 h at −78° C., the reaction was quenched with saturated aqueous ammonium chloride (10 ml), and extracted with ether (4×50 ml). The combined organic extracts were dried over anhydrous sodium sulfate, filtered, and concentrated in vacuo to give crude 32 (12:1 ratio of diastereomers by $^1$H NMR). Purification by flash column chromatography (10% EtOAc/hexanes) afforded pure compound 32 (1.850 g, 89%) as a colorless oil: [α]$^{22}$$_D$=+86.8 (c=1.60, CHCl$_3$); TLC R$_f$=0.34 (silica gel, 20% EtOAc/hexanes); $^1$H NMR (400 MHz, CDCl$_3$) δ 7.34-7.30 (m, 5H), 4.48 (s, 2H), 4.43-4.38 (m, 1H), 4.175-4.15 (d, $^3$J=6 Hz, 2H), 3.81-3.72 (m, 2H), 3.49-3.42 (m, 2H), 2.38-2.30 (m, 1H), 1.86-1.76 (m, 1H), 1.69-1.58 (m, 2H), 1.54-1.44 (m, 1H), 1.23-1.20 (d, $^3$J=6.8 Hz, 3H), 0.91-0.88 (d, $^3$J=6.8 Hz, 3H), 0.87-0.84 (d, $^3$J=7.2 Hz, 3H); $^{13}$C NMR (75 MHz, CDCl$_3$) δ 177.209, 154.281, 138.798, 128.561, 127.794, 127.691, 73.043, 70.478, 63.378, 58.629, 37.729, 29.961, 28.635, 27.641, 18.214, 18.146, 14.901; HRMS calcd for C$_{19}$H$_{27}$NO$_4$+Na$^+$ 356.1838; found 356.1844 [M+Na$^+$].

(2S)-5-Benzyloxy-2-methyl-pentan-1-ol (34)

A solution of aqueous 30% H$_2$O$_2$ (2.88 ml, 26.2 mmol) and lithium hydroxide (0.3 g, 12.45 mmol, in distilled water (4 ml) was added to a solution of imide 32 (2.1 g, 6.3 mmol) in dry THF-distilled water (3:1, 40 ml) at ° C. After 1 h, excess peroxide was quenched by the addition of 1.5 M sodium sulfite solution (19 ml, 28.2 mmol) and the mixture was concentrated in vacuo. The resulting residue (pH~9-10) was washed with methylene chloride (3×40 ml) to recover the chiral ligand. The aqueous phase was acidified to pH~1-2 with 1M HCl and extracted with ether (3×40 ml). The combined ethereal extracts were dried over anhydrous sodium sulfate and concentrated to give crude acid 33. A solution of LiAlH$_4$ (7.56 ml 1.0M solution in THF, 1.2 equiv) was added dropwise to a solution of crude acid 33 (ca. 6.3 mmol, 1 eqiv) in ether at −78° C. The reaction was stirred at −78° C. for 20 min, warmed to 0° C. and stirred for additional 1.5 h. Excess hydride was quenched by dropwise addition of water (0.29 ml), 15% aqueous NaOH (0.29 ml), and water (0.86 ml). Anhydrous sodium sulfate was added, and the resulting suspension was stirred at room temperature for 4 h. The white precipitate formed was filtered through a plug of celite and washed with Et$_2$O. The filtrate and washings were concentrated under reduced pressure to give a crude oil that was purified by flash column chromatography (15% EtOAc/hexanes) to give alcohol 34 (1.2 g, 92% over two steps) as a colorless oil: [α]$^{22}$$_D$=−7.5 (c=0.6, CHCl$_3$); TLC R$_f$=0.52 (silica gel, 50% EtOAc/hexanes); $^1$H NMR (400 MHz, CDCl$_3$) δ 7.35-7.28 (m, 5H), 4.50 (s, 2H), 3.54-3.40 (m, 4H), 1.76-1.45 (m, 4H), 1.40-1.36 (t, $^3$J=5.6 Hz, 1H), 1.25-1.15 (m, 1H), 0.94-0.91 (d, $^3$J=6.8 Hz, 3H); $^{13}$C NMR (75 MHz, CDCl$_3$) δ 138.798, 128.600, 127.885, 127.765, 73.184, 70.890, 68.406, 35.841, 29.830, 27.365, 16.120; HRMS calcd for C$_{13}$H$_{20}$O$_2$+Na$^+$ 231.1361; found 231.1338 [M+Na$^+$].

(2S)-5-Benzyloxy-2-methyl-pentanal (25)

Dess-Martin periodinane (5.19 g, 12.23 mmol, 1.2 equiv) was added to a solution of 34 (2.1 g) in methylene chloride (20 ml) at 0° C. The mixture was stirred at room temperature for 10 min, filtered through a plug of celite and concentrated. Flash column chromatography (10% EtOAc/hexanes) gave aldehyde 25 (1.7 g, 82%) as a colorless oil: [α]$^{22}$$_D$=+15.5 (c=0.5, CHCl$_3$); TLC R$_f$=0.87 (silica gel, 50% EtOAc/hexanes); $^1$H NMR (400 MHz, CDCl$_3$) δ 9.6 (s, 1H), 7.37-7.26 (m, 5H), 4.5 (s, 2H), 3.51-3.46 (t, $^3$J=6 Hz, 2H), 2.41-2.32 (m, 1H), 1.87-1.78 (m, 1H), 1.74-1.60 (m, 2H), 1.52-1.42 (m, 1H), 1.115-1.097 (d, $^3$J=7.2 Hz, 3H); $^{13}$C NMR (75 MHz, CDCl$_3$) δ 205.23, 136.678, 128.62, 127.863, 73.187, 70.171, 46.298, 27.397, 13.529; HRMS calcd for $C_{13}H_{18}O_2$+Na$^+$ 229.1204; found 229.1221 [M+Na$^+$].

2,2-dimethyl-3-oxopentanal (38)

As reported earlier.[86] Colorless liquid: $^1$H NMR (400 MHz, CDCl$_3$) δ 9.61 (s, 1H), 2.52-2.46 (q, $^3$J=7.2 Hz, 2H), 1.33 (s, 6H), 1.06-1.02 (t, $^3$J=7.2 Hz, 3H); $^{13}$C NMR (75 MHz, CDCl$_3$) δ 210.085, 201.417, 60.437, 32.549, 19.545, 7.791; HRMS calcd for $C_7H_{12}O_2$+Na$^+$ 151.0735; found 151.0723 [M+Na$^+$].

(5S)-5-hydroxy-4,4-dimethyloct-7en-3-one (39)

As reported earlier.[87] Colorless oil: $^1$H NMR (400 MHz, CDCl$_3$) δ 5.91-5.80 (m, 1H), 5.15-5.10 (m, 2H), 3.78-3.74 (m, 1H), 2.62-2.45 (m, 2H), 2.40-2.38 (d, $^3$J=4.8 Hz, 1H), 2.29-2.22 (m, 1H), 2.07-1.98 (m, 1H), 1.17 (s, 3H), 1.14 (s, 3H), 1.05-1.0 (t, $^3$J=7.2 Hz, 3H); $^{13}$NMR (75 MHz, CDCl$_3$) δ 213.271, 135.917, 117.967, 75.683, 51.462, 36.706, 31.549, 22.089, 19.734, 8.076; HRMS calcd for $C_{10}H_{18}O_2$+Na$^+$ 193.1204; found 193.1191 [M+Na$^+$].

(5S)-5-(tert-butyl-dimethyl-silanyloxy)-4,4-dimethyloct-7en-3-one (26)

As reported earlier.[87] Colorless oil: $^1$H NMR (400 MHz, CDCl$_3$) δ 5.80-5.70 (m, 1H), 5.03-4.96 (m, 2H), 4.0-3.97 (dd, $^3$J=5.2 Hz, $^2$J=6.4 Hz, 1H), 2.60-2.39 (m, 2H), 2.23-2.08 (m, 2H), 1.1 (s, 3H), 1.08 (s, 3H), 1.0-0.97 ($^3$J=7.2 Hz, 3H), 0.87 (s, 9H), 0.06 (s, 3H), 0.02 (s, 3H); $^{13}$C NMR (75 MHz, CDCl$_3$) δ 214.608, 136.416, 116.770, 76.805, 53.127, 39.219, 32.167, 26.208, 22.668, 20.366, 7.923, −3.359, −4.167; HRMS calcd for $C_{16}H_{32}O_2Si$+Na$^+$ 307.2069; found 307.2051 [M+Na$^+$].

(4S,7R,8S,9S)-12-Benzyloxy-4-(tert-butyl-dimethyl-silanyloxy)-8-hydroxy-5,5,7,9-tetramethyl-dodec-1-en-6-one (40a)

A solution of (5S)-5-(tert-butyl-dimethyl-silanyloxy)-4,4-dimethyl-oct-7-en-3-one 26 (1.268 g, 4.465 mmol, 2.3 equiv) in THF (6 ml) was added dropwise to a solution of freshly prepared LDA in THF [prepared by adding n-butyllithium (2.85 ml of 1.6 M solution in hexanes, 4.56 mmol) to diisopropylamine (0.64 ml, 4.56 mmol) in THF (5 ml) at −78° C., then warming the solution to 0° C. for 20 min, and finally cooling back to −78° C.]. The reaction mixture was stirred at −78° C. for 1 h, at −40° C. for 30 min and then cooled back to −78° C. To this mixture was added, via cannula, a pre-cooled solution of aldehyde 25 (0.4 g, 1.94 mmol, 1 equiv) in THF (10 ml) over 1 min. The reaction mixture was stirred at −78° C. for 10 min and quenched rapidly by injection of a solution of acetic acid (0.53 ml) in THF (1.5 ml). The mixture was stirred at −78° C. for 5 min and then brought to room temperature. Saturated aqueous ammonium chloride (20 ml) and ether (25 ml) were added and the layers were separated. The aqueous layer was extracted with ether (3×25 ml) and the organic extracts were combined, dried over anhydrous sodium sulfate, and concentrated. Flash column chromatography (4-20% ether/hexanes) gave recovered ketone 26 (0.5 g) followed by the diastereomerically pure aldol 40a (0.78 g, 82%) along with other aldol diastereomer 40b (66 mg, 7%) as colorless oils:

Data for 40a: [α]$^{22}_D$=−26.1 (c=1.0, CHCl$_3$); TLC R$_f$=0.36 (silica gel, 25% ether/hexanes); $^1$H NMR (400 MHz, CDCl$_3$) δ 7.35-7.28 (m, 5H), 5.85-5.7 (m, 1H), 5.05-4.98 (m, 2H), 4.502 (s, 2H), 3.95-3.913 (dd, $^3$J=4.4 Hz, $^2$J=6.4 Hz, 1H), 3.52-3.44 (m, 3H), 3.35-3.32 (d, $^3$J=8.8 Hz, 1H), 3.29-3.22 (q, $^3$J=6.4 Hz, 1H), 2.25-2.06 (m, 2H), 1.84-1.50 (m, 5H), 1.181 (s, 3H), 1.125 (s, 3H), 1.05-1.03 (d, $^3$J=6.8 Hz, 3H), 0.90 (s, 9H), 0.854-0.837 (d, $^3$J=6.8 Hz, 3H), 0.078 (s, 3H), 0.064 (s, 3H); $^{13}$C NMR (75 MHz, CDCl$_3$) δ 208.042, 138.909, 136.502, 128.542, 127.853, 127.661, 116.955, 76.716, 75.097, 73.112, 71.168, 54.577, 41.382, 39.789, 35.568, 29.453, 27.123, 26.279, 23.644, 19.567, 18.457, 15.620, 10.020, −3.242, −3.804; HRMS calcd for $C_{29}H_{50}O_4Si$+Na$^+$ 513.3376; found 513.3383 [M+Na$^+$].

3-Oxo-2-(2-oxo-2-phenyl-ethyl)-pentanoic Acid Ethyl Ester (47a)

Ethyl propionylacetate (45) (10 g, 69.4 mmol) was added slowly to a stirred suspension of sodium hydride (60% dispersion in mineral oil, 3.33 g, 83.3 mmol, 1.2 equiv) in THF (100 ml) at 0° C. and the mixture was stirred for 30 min. 2-Bromoacetophenone 46a (15.2 g, 76.34 mmol, 1.1 equiv) in THF (10 ml) was added dropwise and the reaction mixture was stirred at room temperature for 16 h. Saturated aqueous ammonium chloride (60 ml) was added and the mixture was subsequently extracted with diethyl ether (3×70 ml). The combined organic layers were washed with brine and dried over anhydrous sodium sulfate. The solvent was removed in vacuo to give a dark yellow oil that was purified by flash column chromatography (EtOAc-hexane, 1:10) to give the diketoester 47a (14.8 g, 81%) as a yellow oil: TLC R$_f$=0.50 (silica gel, 25% EtOAc/hexanes); $^1$H NMR (400 MHz, CDCl$_3$) δ 7.98 (d, $^3$J=8.4 Hz, 2H), 7.58 (m, 1H), 7.46 (m, 2H), 4.18-4.25 (q, $^3$J=7.2 Hz, 3H), 3.70-3.3.79 (dd, $^3$J=8.4 Hz, $^2$J=18.4 Hz, 1H), 3.49-3.57 (dd, $^3$J=5.2 Hz, $^2$J=18.4 Hz, 1H), 2.70-2.91 (m, 2H), 1.26-1.31 (t, $^3$J=7.2 Hz, 3H), 1.10-1.15 (t, $^3$J=7.2 Hz, 3H); $^{13}$C NMR (75 MHz, CDCl$_3$) δ 205.42, 197.43, 169.26, 136.29, 133.63, 128.81, 128.31, 61.864, 53.20, 37.68, 36.55, 14.22, 7.84; HRMS calcd for $C_{15}H_{18}O_4$+Na$^+$ 285.1103; found 285.1093 [M+Na$^+$].

3-Methyl-2-oxo-4-phenyl-cyclopent-3-enecarboxylic Acid Ethyl Ester (+/−48a)

A solution of the diketoester 47a (12 g, 45.8 mmol) in dry ethanol (150 ml) was added dropwise to a solution of sodium hydroxide (1.83 g, 45.8 mmol) in dry ethanol (75 ml) with vigorous stirring. The solution was heated to 50° C. and stirred overnight at that temperature. Ether (1.5 L) was and the organic phase was washed with 2.0 M hydrochloric acid (3×300 ml) and dried over anhydrous sodium sulfate.

The solvent was removed in vacuo to give an oil that was purified by flash column chromatography (EtOAc-hexane, 1:15) to give the cyclic β-ketoester (+/−) 48a (8.7 g, 78%) as a yellow oil: TLC R$_f$=0.40 (silica gel, 25% EtOAc/hexane); $^1$H NMR (400 MHz, CDCl$_3$) δ 7.56-7.52 (m, 2H), 7.50-7.42 (m, 3H), 4.29-4.22 (q, $^3$J=7.2 Hz, 2H), 3.59-3.56 (dd, $^3$J=3.2 Hz, $^2$J=7.6 Hz, 1H), 3.38-3.31 (m, 1H), 3.15-3.07 (m, 1H), 1.99 (s, 3H), 1.35-1.30 (t, $^3$J=7.2 Hz, 3H); $^{13}$C NMR (75 MHz, CDCl$_3$) δ 202.593, 169.605, 166.477, 135.828, 134.955, 130.179, 128.936, 127.954, 61.900, 51.297, 33.671, 14.461, 10.486; HRMS calcd for $C_{15}H_{16}O_3$+Na$^+$ 267.0997; found 267.0974 [M+Na$^+$].

1-(5-methylpyridin-2-yl)-ethanone (51)

To a solution of 2-bromo-5-methylpyridine 49 (1.73 g, 10 mmol) in dry ether (20 ml), cooled to −78° C., was added n-butyllithium (6.25 ml of 1.6M solution in hexanes, 10 mmol, 1 equiv) dropwise. The reaction mixture was allowed to warm to −40° C. for 15 min, then cooled back to −78° C. again. N,N-dimethylacetamide (1.023 ml, 11 mmol, 1.1 equiv) was added dropwise and the mixture was stirred at −78° C. for 2 h. Saturated aqueous ammonium chloride (10 ml) was added and the organic layer was separated. The aqueous layer was extracted with ether (3×10 ml) and the combined organic layers were dried over anhydrous sodium sulfate, filtered, and concentrated in vacuo to give an oily residue that was subjected to flash column chromatography using (5% methanol in methylene chloride) to give compound 51 (0.977 g, 72%) as a yellow oil: TLC $R_f$=0.48 (silica gel, 25% EtOAc/hexanes); $^1$H NMR (400 MHz, CDCl$_3$) δ 8.5-8.48 (m, 1H), 7.96-7.93 (d, $^3$J=8 Hz, 1H), 7.63-7.60 (m, 1H), 2.70 (s, 3H), 2.414 (s, 3H); $^{13}$C NMR (75 MHz, CDCl$_3$) δ 200.239, 151.741, 149.704, 137.786, 137.442, 121.663, 26.017, 18.969; HRMS calcd for C$_8$H$_9$NO+Na$^+$ 158.0582; found 158.0580 [M+Na$^+$].

2-bromo-1-(5-methylpyridin-2-yl)ethanone (46b)

To a solution of compound 51 (0.9 g, 6.67 mmol) in THF (25 ml) was added Amberlyst A26-Br$_3^-$ (Aldrich, 1.26 mmol Br$_3$/g) (4.76 g, 6 mmol, 0.9 equiv) in one portion. The mixture was stirred at 50° C. for 10 h and the decolored resin was filtered off and washed with ethyl acetate. The organic solution was washed with water, dried over anhydrous sodium sulfate, and concentrated in vacuo to give an oily residue that was chromatographed on silica gel with (10-30% methylene chloride in hexanes) to give compound 46b (1.29 g, 91%) as an yellow oil: TLC $R_f$=0.62 (silica gel, 20% EtOAc/hexane); $^1$H NMR (400 MHz, CDCl$_3$) δ 8.50 (broad s, 1H), 8.02-7.99 (d, $^3$J=8 Hz, 1H), 7.67-7.64 (dd, $^3$J=1.6 Hz, $^2$J=8 Hz, 1H), 4.84 (s, 2H), 2.44 (s, 3H); $^{13}$C NMR (75 MHz, CDCl$_3$) δ 192.476, 149.775, 149.317, 138.653, 137.601, 122.594, 32.492, 18.955; HRMS calcd for C$_8$H$_8$BrNO+Na$^+$ 235.9687; found 235.9676 [M+Na$^+$].

3-Oxo-2-(2-oxo-2-pyridin-2-yl-ethyl)-pentanoic Acid Ethyl Ester (47b)

Ethyl propionylacetate (45) (5 g, 34.7 mmol) was added slowly to a stirred suspension of sodium hydride (60% dispersion in mineral oil, 1.665 g, 41.65 mmol, 1.2 equiv) in THF (50 ml) at 0° C. and the mixture was stirred for 30 min. Compound 46b (8.092 g, 38.17 mmol, 1.1 equiv) in THF (5 ml) was added dropwise and the reaction mixture was stirred at room temperature for 16 h. Saturated aqueous ammonium chloride (30 ml) was added and the mixture was subsequently extracted with diethyl ether (3×30 ml). The combined organic layers were washed with brine and dried over anhydrous sodium sulfate. The solvent was removed in vacuo to give a dark yellow oil that was purified by flash column chromatography (EtOAc/hexanes, 1:10) to give the diketoester 47b (7.3 g, 76%) as a yellow oil: TLC $R_f$=0.33 (silica gel, 20% EtOAc/hexane); $^1$H NMR (400 MHz, CDCl$_3$) δ 8.5 (broad s, 1H), 7.9-7.87 (d, $^3$J=8 Hz, 1H), 7.67-7.64 (dd, $^3$J=1.6 Hz, $^2$J=8 Hz, 1H), 4.23-4.17 (q, $^3$J=7.2 Hz, 2H), 4.17-4.13 (dd, $^3$J=6 Hz, $^2$J=8 Hz, 1H), 3.96-3.89 (dd, $^3$J=8.4 Hz, $^2$J=18.8 Hz, 1H), 3.78-3.71 (dd, $^3$J=6 Hz, $^2$J=18.8 Hz, 1H), 2.85-2.66 (m, 2H), 2.412 (s, 3H), 1.29-1.25 (t, $^3$J=7.2 Hz, 3H), 1.27-1.09 ($^3$J=7.2 Hz, 3H); $^{13}$C NMR (75 MHz, CDCl$_3$) δ 205.463, 198.902, 169.557, 150.697, 149.748, 138.125, 137.344, 121.709, 61.745, 53.460, 37.110, 36.191, 18.944, 14.249, 7.875; HRMS calcd for C$_{15}$H$_{19}$NO$_4$+Na$^+$ 300.1212; found 300.1200 [M+Na$^+$].

3-Methyl-2-oxo-4-pyridin-2-yl-cyclopent-3-enecarboxylic Acid Ethyl Ester (+/−48b)

A solution of the diketoester 47b (3.1 g, 11.19 mmol) in dry ethanol (35 ml) was added dropwise to a solution of sodium hydroxide (0.447 g, 11.19 mmol) in dry ethanol (15 ml) with vigorous stirring. The solution was stirred at room temperature overnight. Ether (200 ml) was and the organic phase was washed with 2.0 M hydrochloric acid (3×100 ml). The aqueous layer was cooled to 0° C. and made slightly basic by addition of sodium bicarbonate. The aqueous layer was then extracted with ethyl acetate (3×300 ml) and the organic phase was dried over anhydrous sodium sulfate. The solvent was removed in vacuo to give an oil that was purified by flash column chromatography (EtOAc/hexanes, 1:10) to give the cyclic β-ketoester (+/−) 48b (2.115 g, 73%) as a yellow oil: TLC $R_f$=0.35 (silica gel, 33% EtOAc/hexanes); $^1$H NMR (400 MHz, CDCl$_3$) δ 8.59 (s, 1H), 7.62-7.60 (m, 1H), 7.54-7.52 (m, 1H), 4.27-4.21 (q, $^3$J=7.2 Hz, 2H), 3.58-3.55 (dd, $^3$J=2.8 Hz, $^2$J=7.2 Hz, 1H), 3.42-3.25 (m, 2H), 2.41 (s, 3H), 2.12 (s, 3H), 1.33-1.29 (t, $^3$J=7.2 Hz, 3H); $^{13}$C NMR (75 MHz, CDCl$_3$) δ 203.180, 169.521, 164.379, 151.379, 150.614, 136.787, 136.482, 134.188, 123.331, 61.688, 51.063, 32.495, 18.617, 14.322, 10.597; HRMS calcd for C$_{15}$H$_{17}$NO$_3$+Na$^+$ 282.1106; found 282.1109 [M+Na$^+$].

(1R*,2S*,3E)-2-Hydroxy-3-methyl-4-phenyl-cyclopent-3-enecarboxylic Acid Ethyl Ester (+/−52a)

A solution of zinc borohydride (150 ml of 0.3M solution in ether, 45 mmol, 4 equiv) was added dropwise at 0° C. to a stirred solution of β-ketoester (+/−) 48a (2.75 g, 11.25 mmol) in THF (5 ml). The mixture was stirred overnight at 4° C., quenched by slow addition of water and stirred for about 1 hour. Anhydrous sodium sulfate was added and the resulting suspension was filtered and the filtrate was concentrated. The residue was dissolved in methylene chloride and filtered again and dried. Purification by flash column chromatography (EtOAc/hexanes, 1:12) gave recovered starting material (0.27 g, 10%) and racemic β-hydroxyester (+/−) 52a (2.1 g, 75%) as a yellow oil: TLC $R_f$=0.17 (silica gel, 25% EtOAc/hexanes); $^1$H NMR (400 MHz, CDCl$_3$) δ 7.37-7.24 (m, 5H), 4.98 (s, 1H), 4.25-4.20 (q, 3J=7.2 Hz, 2H), 3.03-2.94 (m, 3H), 2.33-2.31 (d, $^3$J=5.6 Hz, 1H), 1.90-1.89 (d, $^3$J=1.2 Hz, 3H), 1.33-1.29 (t, $^3$J=7.2 Hz, 3H); $^{13}$C NMR (100 MHz, CDCl$_3$) δ 174.878, 137.229, 135.744, 135.076, 128.425, 127.934, 127.336, 83.964, 61.102, 51.799, 37.077, 14.525, 12.825; HRMS calcd for C$_{15}$H$_{18}$O$_3$+Na$^+$ 269.1154; found 269.1143 [M+Na$^+$].

(1R,2S,3E)-2-Acetoxy-3-methyl-4-phenyl-cyclopent-3-enecarboxylic Acid Ethyl Ester (−) 84 and (1R,2R,3E)-2-Hydroxy-3-methyl-4-phenyl-cyclopent-3-enecarboxylic Acid Ethyl Ester (−) 52a Vinyl acetate (7.5 ml, 81.4 mmol) was added to a solution of (+/−) 52a (2 g, 8.13 mmol) in anhydrous pentane (30 ml). Amano PS-D lipase (2.0 g) and 4 Å MS (2.0 g) were added and the suspension was stirred at room temperature. The reaction was monitored by TLC and $^1$H NMR and after 4 days 48-50% conversion of (+/−) 52a to the acetate (−) 54 was achieved. The sieves and lipase were filtered and washed with Et$_2$O. The solvent was removed and crude product was purified by flash column chromatography (ether/hexanes, 1:4) to give (−) 54 (1.15 g, 49%) as a slightly yellow oil along with (−) 52a (0.96 g, 48%. 98% ee).

Data for (−) 54: $[\alpha]^{22}_D$=−50.5 (c=0.6, CHCl$_3$); TLC $R_f$=0.38 (silica gel, 25% EtOAc/hexanes); $^1$H NMR (600

MHz, CDCl$_3$) δ 7.40-7.25 (m, 5H), 6.06 (s, 1H), 4.22-4.18 (q, $^3$J=7.2 Hz, 2H), 3.08-2.95 (m, 3H), 2.11 (s, 3H), 1.797 (s, 3H), 1.29-1.26 (t, $^3$J=7.2 Hz, 3H); $^{13}$C NMR (100 MHz, CDCl$_3$) δ 174.227, 170.951, 138.398, 136.673, 131.751, 128.491, 128.004, 127.683, 85.90, 61.186, 48.68, 38.625, 21.301, 14.402, 12.867; HRMS calcd for C$_{17}$H$_{20}$O$_4$+Na$^+$ 311.1259; found 311.1240 [M+Na$^+$].

Data for (−) 52a; [α]$^{22}_D$=−15.2 (c=0.6, CHCl$_3$); TLC R$_f$=0.17 (silica gel, 25% EtOAc/hexane); $^1$H NMR (400 MHz, CDCl$_3$) δ 7.36-7.22 (m, 5H), 5.0 (d, $^3$J=5.2 Hz, 1H), 4.22-4.17 (q, $^3$J=7.2 Hz, 2H), 3.06-2.93 (m, 3H), 2.34-2.32 (d, $^3$J=5.6 Hz, 1H), 1.90 (s, 3H), 1.30-1.27 (t, $^3$J=7.2 Hz, 3H); $^{13}$C NMR (100 MHz, CDCl$_3$) δ 174.887, 137.238, 135.753, 135.085, 128.714, 127.943, 127.365, 83.973, 61.111, 51.808, 37.086, 14.534, 12.834.

(1R,2S,3E)-2-Hydroxy-3-methyl-4-phenyl-cyclopent-3-enecarboxylic Acid Ethyl Ester (+) 52a Anhydrous potassium carbonate (240 mg, 1.74 mmol) was added at 0° C. to a solution of (−) 84 (500 mg, 1.74 mmol) in dry ethanol (15 ml) and the solution was stirred at room temperature for 12 hr. Ethanol was removed under reduced pressure and the residue was dissolved in methylene chloride and washed with saturated aqueous solution of ammonium chloride. The organic phase was dried over anhydrous sodium sulfate and the solvent was removed in vacuo. The residue was purified by flash column chromatography (EtOAc-hexane, 1:3) to give compound (+) 52a (393 mg, 92%, 99% ee) as a slightly yellow oil: [α]$^{22}_D$ =+14.8 (c=0.8, CHCl$_3$); TLC R$_f$=0.17 (silica gel, 25% EtOAc/hexane); $^1$H NMR (400 MHz, CDCl$_3$) δ 7.37-7.25 (m, 5H), 4.99 (s, 1H), 4.26-4.20 (q, $^3$J=7.2 Hz, 2H), 3.05-2.94 (m, 3H), 2.34-2.32 (d, $^3$J=5.6 Hz, 1H), 1.91-1.89 (d, $^3$J=1.2 Hz, 3H), 1.34-1.29 (t, $^3$J=7.2 Hz, 3H); $^{13}$C NMR (100 MHz, CDCl$_3$) δ 175.184, 137.308, 135.435, 135.419, 128.438, 127.955, 127.328, 83.862, 61.103, 51.680, 37.288, 14.522, 12.896; HRMS calcd for C$_{15}$H$_{18}$O$_3$+Na$^+$ 269.1154; found 269.1148 [M+Na$^+$].

(1R,2S,3E)-3-Methyl-4-phenyl-2-triethylsilanyloxy-cyclopent-3-enecarboxylic Acid Ethyl Ester (−) 55

Triethylsilyl chloride (876 μL, 5.22 mmol, 1.5 equiv) was added dropwise to a solution of alcohol (+) 52a (856 mg, 3.48 mmol) and imidazole (711 mg, 10.44 mmol, 3 equiv) in methylene chloride (25 ml) at 0° C. After stirring at 0° C. for 2 hr, the reaction was quenched with water (15 ml), and extracted with ethyl acetate (3×30 ml). The organic extracts were washed with brine (20 ml), and dried over anhydrous sodium sulfate. Filtration and evaporation of the solvents in vacuo furnished an oily crude product which was purified by flash column chromatography (2% EtOAc/hexanes) to give TES ether (−) 55 (1.16 g, 93%) as a yellow oil:: [α]$^{22}_D$=−34.2 (c=0.6, CHCl$_3$); TLC R$_f$=0.53 (silica gel, 10% EtOAc/hexanes); $^1$H NMR (400 MHz, CDCl$_3$) δ 7.36-7.22 (m, 5H), 5.11 (s, 1H), 4.24-4.18 (q, $^3$J=7.2 Hz, 2H), 3.08-2.82 (m, 3H), 1.83 (s, 3H), 1.34-1.29 (t, $^3$J=7.2 Hz, 3H), 1.02-0.97 (t, $^3$J=8 Hz, 9H), 0.71-0.64 (q, $^3$J=8 Hz, 6H); $^{13}$C NMR (75 MHz, CDCl$_3$) δ 175.525, 137.491, 135.728, 134.988, 128.334, 128.028, 127.172, 84.518, 60.922, 51.813, 38.603, 14.482, 12.965, 7.065, 5.131, 0.179; HRMS calcd for C$_{21}$H$_{32}$O$_3$Si+Na$^+$ 383.2018; found 383.2019 [M+Na$^+$].

(1R,2S,3E)-3-Methyl-4-phenyl-2-triethylsilanyloxy-cyclopent-3-enecarbaldehyde (56)

A solution of DIBAL-H (2.2 ml, 1.0M in hexane, 2.2 mmol, 1.1 equiv) was added dropwise to a solution of silyl ether 55 (720 mg, 2 mmol) in toluene (10 ml) at −78° C. The reaction was stirred at that temperature for 1 h and quenched by dropwise addition of saturated NH$_4$Cl (1.0 ml). The reaction was allowed to reach room temperature and a saturated solution of Rochelle salt (3.0 ml) and brine (2.0 ml) were added. The mixture was extracted with ethyl acetate (3×7 ml) and the combined organic extracts were dried over anhydrous sodium sulfate, filtered, and evaporated in vacuo to give crude aldehyde 56 as a colorless liquid which was used in the next step without further purification; $^1$H NMR (400 MHz, CDCl$_3$) δ 9.86-9.85 (d, $^3$J=2 Hz, 1H), 7.38-7.25 (m, 5H), 5.08 (s, 1H), 3.12-2.98 (m, 2H), 2.90-2.84 (m, 1H), 1.84 (s, 3H), 1.02-0.98 (t, $^3$J=8 Hz, 9H), 0.72-0.65 (q, $^3$J=8 Hz, 6H); $^{13}$C NMR (75 MHz, CDCl$_3$) δ 200.239, 135.465, 133.901, 133.698, 126.638, 126.267, 125.606, 79.549, 57.417, 33.140, 11.303, 5.298, 3.378.

(1S,2E)-Triethyl-[5S-(2Z-iodo-propenyl)-2-methyl-3-phenyl-cyclopent-2-enyloxy]-silane (58)

To a suspension of ethyl triphenylphosphonium iodide (1.746 g, 4.177 mmol, 3 equiv) in THF (10 ml) at 0° C. was added n-butyllithium (1.640 ml of 2.5 M solution in hexanes, 4.1 mmol, 2.95 equiv). The resulting red ylide solution was stirred at room temperature for 30 min before it was added dropwise to a vigorously stirred solution of iodine (1.028 g, 4.05 mmol, 2.90 eq) in THF (30 ml) in the presence of 4 Å MS (590 mg) at −78° C. [The iodine mixture was stirred at room temperature for 30 min before cooling to −78° C.]. The resulting yellow suspension was stirred vigorously for 10 min at −78° C. and for 30 min at −20° C. in an ethylene glycol and dry-ice cooling bath. A solution of sodium hexamethyldisilazane (3.91 ml of 1.0 M in THF, 3.91 mmol, 2.8 equiv) was added dropwise and the mixture was stirred at −20° C. for 15 min. A solution of aldehyde 56 (440 mg, 1.392 mmol, 1 equiv) in THF (2 ml) was added dropwise. After stirring for 45 min at −20° C. the reaction was quenched with saturated aqueous ammonium chloride (0.5 ml). A mixture of hexanes/ethylacetate (4:1, 20 ml) was added and the mixture was filtered through a small plug of silica and the filtrate was concentrated in vacuo. Purification by flash chromatography (2% EtOAc/hexanes) gave vinyl iodide 58 (380 mg, 60%) as a pale yellow oil: TLC R$_f$=(silica gel, % EtOAc/hexanes); $^1$H NMR (400 MHz, CDCl$_3$) δ 7.33-7.25 (m, 5H), 5.56 (d, $^3$J=8 Hz, 1H), 4.63 (s, 1H), 3.02-2.93 (m, 2H), 2.54 (s, 3H), 2.41-2.30 (m, 1H), 1.84 (s, 3H), 1.02-0.98 (t, $^3$J=8 Hz, 9H), 0.69-0.63 (q, $^3$J=8 Hz, 6H); $^{13}$C NMR (75 MHz, CDCl$_3$) 6; 138.447, 137.931, 136.611, 135.538, 128.310, 127.938, 126.994, 101.780, 86.548, 54.807, 39.558, 33.893, 13.152, 7.252, 5.399; HRMS calcd for C$_{21}$H$_{32}$O$_3$Si+Na$^+$; found [M+Na$^+$].

6-Methyl-hept-6-enoic Acid (71)

n-Butyllithium (10.8 ml of 2.5 M in hexanes, 27 mmol, 1.3 equiv) was added to a solution of methyltriphenylphosphonium bromide (9.7 g, 27 mmol, 1.3 equiv) in dimethyl sulfoxide (50 ml) at 0° C., and the mixture was stirred at room temperature for 1 h. It was added to a solution of 6-oxo-heptanoic acid 70 (3 g, 20.82 mmol, 1 equiv) and n-butyllithium (8.33 ml of 2.5 M in hexanes, 20.82 mmol, 1 equiv) in THF (30 ml). The mixture was stirred at room temperature for 48 hr. Water was added and the mixture was acidified with 2 N HCl and extracted with methylene chloride (3×50 ml). The organic layer was washed with 10% sodium hydroxide solution. The aqueous layer was acidified with 2.0 N HCl and extracted with ethyl acetate (3×60 ml). The organic extracts were dried over anhydrous sodium sulfate and concentrated in vacuo. Purification by flash column chromatography (10% EtOAc/hexanes) gave pure acid 123 (2.32 g, 78%) as a colorless oil: TLC $R_f$=0.47 (silica gel, 25% EtOAc/hexanes); $^1$H NMR (600 MHz, CDCl$_3$) δ 4.688 (s, 1H), 4.653 (s, 1H), 2.36-2.33 (t, $^3J$=7.8 Hz, 2H), 2.03-1.99 (t, $^3J$=7.8 Hz, 2H), 1.687 (s, 3H), 1.64-1.58 (m, 2H), 1.50-1.44 (m, 2H); $^{13}$C NMR (100 MHz, CDCl$_3$) δ 180.696, 145.56, 110.362, 37.54, 34.182, 27.098, 24.436, 22.477; HRMS calcd for C$_{42}$H$_{70}$O$_5$Si$_2$+Na$^+$; found [M+Na$^+$].

6-Methyl-hept-6-enoyl Chloride (72)

To a solution of the carboxylic acid 71 (2.2 g, 15.5 mmol) in benzene (30 ml), was added oxalyl chloride (3 ml, 34.4 mmol, 2.22 equiv). A drying tube was placed on the flask and the reaction mixture was stirred for 90 min at room temperature before it was concentrated in vacuo. The crude acid chloride was used in the next step without further purification: TLC $R_f$=0.37 (silica gel, 25% EtOAc/hexanes); $^1$H NMR (600 MHz, CDCl$_3$) δ 4.69 (s, 1H), 4.67 (s, 1H), 2.90-2.87 (t, $^3J$=7.8 Hz, 2H), 2.03-2.00 (t, $^3J$=7.8 Hz, 2H), 1.74-1.66 (m, 2H), 1.69 (s, 3H), 1.58-1.46 (m, 2H); $^{13}$C NMR (100 MHz, CDCl$_3$) δ 173.979, 145.086, 110.717, 46.663, 37.334, 26.421, 24.799, 22.431.

(4S)-4-Isopropyl-3-(6-methyl-hept-6-enoyl)-oxazolidin-2-one (73)

To a solution of (S)-4-isopropyl-2-oxazolidonone (1.56 g, 12.1 mmol, 1 equiv) in THF (40 ml) at −78° C. was added n-butyllithium (4.84 ml of a 2.5 M solution in hexanes, 12.1 mmol, 1 equiv). After 15 min acid chloride (2.14 g, 13.3 mmol, 1.1 equiv) was added and the mixture was stirred for 30 min at −78° C. and for 15 min at 0° C. Saturated aqueous ammonium chloride (10 ml) was added and the resulting slurry was concentrated in vacuo. The residue was diluted with ether and washed successively with saturated aqueous sodium bicarbonate and brine. The organic layer was dried over anhydrous sodium sulfate, filtered, and concentrated in vacuo. Purification by flash chromatography (10% EtOAc/hexanes) gave imide 73 (2.94 g, 96%) as a colorless oil: [α]$^{22}_D$=+66.7 (c=0.6, CHCl$_3$); TLC $R_f$=0.40 (silica gel, 25% EtOAc/hexanes); $^1$H NMR (600 MHz, CDCl$_3$) δ 4.682 (s, 1H), 4.656 (s, 1H), 4.428-4.40 (m, 1H), 4.263-4.230 (t, $^2J$=9 Hz, 1H), 4.198-4.178 (dd, $^2J$=9 Hz, $^3J$=3 Hz, 1H), 3.01-2.83 (m, 2H), 2.381-2.32 (m, 1H), 2.04-2.01 (t, $^3J$=7.8 Hz, 2H), 1.691 (s, 3H), 1.67-1.61 (m, 2H), 1.51-1.46 (m, 2H), 0.904-0.891 (d, $^3J$=7.2 Hz, 3H), 0.86-0.848 (d, $^3J$=7.2 Hz, 3H); $^{13}$C NMR (100 MHz, CDCl$_3$) δ 173.488, 154.311, 145.775, 110.238, 63.546, 58.615, 37.697, 35.609, 28.603, 27.217, 24.275, 22.563, 18.206, 14.877; HRMS calcd for C$_{14}$H$_{23}$NO$_3$+Na$^+$ 276.1576; found 276.1567 [M+Na$^+$].

(4S)-3-[(2S)-2,6-Dimethyl-hept-6-enoyl)-4-isopropyl-oxazolidin-2-one (74)

As reported by Schinzer et al.[104] Sodium hexamethyldisilazane (13 ml of 1.0 M in THF, 13 mmol, 1.1 equiv) was added dropwise to a solution of imide 73 (3.0 g, 11.9 mmol, 1 equiv) in THF (15 ml) at −78° C. The reaction mixture was stirred for 30 min and a solution of iodomethane (3.74 ml, 60 mmol, 5 equiv) in THF (2 ml) was added dropwise. After stirring for 10 h at −78° C., the reaction was quenched with saturated aqueous ammonium chloride (10 ml), and extracted with ether (4×50 ml). The combined organic extracts were dried over anhydrous sodium sulfate, filtered, and concentrated in vacuo to give crude product 74 (12:1 ratio of diastereomers by $^1$H NMR). Purification by flash column chromatography (10% EtOAc/hexanes) afforded compound 74 (2.69 g, 85%) as a colorless oil: [α]$^{22}_D$=+87.2 (c=0.5, CHCl$_3$); TLC $R_f$=0.47 (silica gel, 25% EtOAc/hexanes); $^1$H NMR (600 MHz, CDCl3) δ 4.674 (s, 1H), 4.642 (s, 1H), 4.45-4.42 (m, 1H), 4.265-4.23 (t, $^2J$=9 Hz, 1H), 4.2-4.17 (dd, $^2J$=9.6 Hz, $^3J$=3 Hz, 1H), 3.75-3.69 (m, 1H), 2.36-2.29 (m, 1H), 2.01-1.97 (t, $^2J$=7.2 Hz, 2H), 1.68 (s, 3H), 1.57-1.30 (m, 4H), 1.195-1.183 (d, $^3J$=7.2 Hz, 3H), 0.9-0.888 (d, $^3J$=7.2 Hz, 3H), 0.861-0.85 (d, $^3J$=6.6 Hz, 3H); $^{13}$C NMR (100 MHz, CDCl$_3$) δ 177.338, 153.886, 145.779, 110.214, 63.414, 58.628, 37.903, 37.866, 32.833, 28.632, 25.381, 22.538, 18.165, 18.132, 14.901.

(2S)-2,6-Dimethyl-hept-6-en-1-ol (75)

As reported by Schinzer et al.[104], a solution of lithium aluminum hydride (8.4 ml of 1.0M solution in THF, 8.4 mmol, 1.5 equiv) was added dropwise to a solution of compound 74 (1.5 g, 5.62 mmol, 1 equiv) in ether (40 ml) at 0° C. The reaction mixture was stirred at 0° C. for 30 min before it was warmed to room temperature and stirred for an additional 10 h. The reaction mixture was cooled again to 0° C. and excess hydride was quenched by dropwise addition of water (0.32 ml), 15% aqueous sodium hydroxide (0.32 ml), and water (1 ml). Anhydrous sodium sulfate was added, and the resulting suspension was stirred at room temperature for 4 h. The white precipitate formed was filtered through a plug of celite and washed with ether. The filtrate and washings were concentrated in vacuo to give a crude oil that was purified by flash column chromatography (15% EtOAc/hexanes) to give alcohol 75 (0.772 g, 97%) as a colorless oil. The column was eluted with ethyl acetate to recover the chiral auxiliary: [α]$^{22}_D$=−10.3 (c=0.8, CHCl$_3$); TLC $R_f$=0.39 (silica gel, 25% EtOAc/hexanes); $^1$H NMR (600 MHz, CDCl$_3$) δ 4.670 (s, 1H), 4.64 (s, 1H), 3.50-3.46 (m, 1H), 3.41-3.37 (m, 1H), 2.02-1.92 (ni, 2H), 1.685 (s, 3H), 1.65-1.34 (m, 4H), 1.12-1.04 (m, 1H), 0.909-0.89 (d, $^3J$=6.6 Hz, 3H); $^{13}$C NMR (100 MHz, CDCl$_3$) δ 146.224, 110.011, 68.538, 38.237, 35.898, 32.948, 25.146, 22.576, 16.787.

(2S)-2,6-Dimethyl-hept-6-enal (67)

As reported by Schinzer et al.[104] Dess-Martin periodinane (3.23 g, 7.61 mmol, 1.2 equiv) was added to a solution of alcohol 75 (0.9 g, 6.34 mmol) in methylene chloride (12 ml). The mixture was stirred at room temperature for 15 min before it was subjected to flash column chromatography (10% EtOAc/hexanes) to furnish aldehyde 67 (0.745 g, 84%) as highly volatile colorless liquid: [α]$^{22}_D$=+11.8 (c=0.5, CHCl$_3$); TLC $R_f$=0.64 (silica gel, 25% EtOAc/hexanes); $^1$H NMR (600 MHz, CDCl$_3$) δ 9.57-9.56 (d, $^3J$=1.8 Hz, 1H), 4.661 (s, 1H), 4.62 (s, 1H), 2.34-2.28 (m, 1H), 2.01-1.95 (t, $^3J$=7.8 Hz, 2H), 1.69-1.62 (m, 4H), 1.48-1.27 (m, 3H), 1.06-1.04 (d, $^3J$=6.6 Hz, 3H); $^{13}$C NMR (100 MHz, CDCl$_3$) δ 205.282, 145.420, 110.441, 46.390, 37.845, 30.20, 24.969, 22.444, 13.523.

(3S)-3-(tert-Butyl-dimethyl-silanyloxy)-4,4-dimethyl-5-oxo-heptanal (76)

Ozonolysis of olefin 26 was performed by adapting an analogues procedure to Nicolaou's et al. procedure.[87] $^1$H NMR (600 MHz, CDCl$_3$) δ 9.77-9.76 (dd, $^3J$=1.8 Hz, $^2J$=2.4 Hz, 1H), 4.55-4.53 (dd, $^3J$=4.8 Hz, $^2J$=6 Hz, 1H), 2.55-2.43 (m, 4H), 1.12 (s, 3H), 1.08 (s, 3H), 1.0-0.97 (t, $^3J$=7.2 Hz, 3H), 0.84 (s, 9H), 0.05 (s, 3H), 0.02 (s, 3H).

(5S)-5,7-Bis-(tert-butyl-dimethyl-silanyloxy)-4,4-dimethyl-heptan-3-one (68)

Sodium borohydride (570 mg, 15.4 mmol, 2 equiv) was dissolved in methylene chloride (175 ml) and dry ethanol (75 ml). The mixture was cooled to −78° C. for 15 min after which a solution of aldehyde 76 (2.2 g, 7.7 mmol, 1 equiv) in methylene chloride (5 ml) was added. After stirring for 1 h water (6 ml) was added and the reaction mixture was allowed to warm to room temperature. Methylene chloride (400 ml) was added and the mixture was washed with saturated aqueous sodium bicarbonate before it was dried over anhydrous sodium sulfate and concentrated in vacuo to give crude alcohol mixture 77 and 78. The crude alcohol mixture was dissolved in methylene chloride (40 ml) and cooled to 0° C. Imidazole (3.14 g, 46.15 mmol, 6 equiv) and tert-butyldimethylsilyl chloride (3.47 g, 23.1 mmol, 3 equiv) were added and the reaction mixture was stirred at room temperature for 16 hr. Saturated aqueous ammonium chloride (30 ml) was added and the layers were separated. The aqueous layer was further extracted with ethyl acetate (3×30) and combined organic extracts were dried over anhydrous sodium sulfate and concentrated in vacuo. Purification by flash chromatography (1%-5% EtOAc/Hexanes) gave the bis(silylether) 68 (2.5 g, 81% over two steps) as a colorless oil: $[\alpha]^{22}_D$=−7.4 (c=1.8, CHCl$_3$); TLC R$_f$=0.70 (silica gel, 20% EtOAc/hexanes); $^1$H NMR (600 MHz, CDCl$_3$) δ 4.058-4.022 (dd, 1H), 3.62-3.54 (m, 2H), 2.57-2.50 (dq, 1H), 2.48-2.40 (dq, 1H), 1.53-1.41 (m, 2H), 1.085 (s, 3H), 1.022 (s, 3H), 0.985-0.96 (t, 3H), 0.86-0.85 (d, 18H), 0.067 (s, 3H), 0.018 (s, 3H), 0.013 (s, 3H), 0.002 (s, 3H); $^{13}$C NMR (100 MHz, CDCl$_3$) δ 215.783, 73.613, 60.286, 53.247, 37.458, 31.76, 26.276, 26.116, 22.386, 20.199, 18.533, 18.441, 7.941, −3.805, −3.834, −5.105; HRMS calcd for C$_{21}$H$_{46}$O$_3$Si$_2$+Na$^+$ 425.2883; found 425.2885 [M+Na$^+$].

(3S,6R,7S,8S)-1,3-Bis-(tert-butyl-dimethyl-silanyloxy)-7-hydroxy-4,4,6,8,12-pentamethyl-tridec-12-en-5-one (79)

A solution of ketone 68 (1.8 g, 4.48 mmol, 2.3 equiv) in THF (5 ml) was added dropwise to a solution of freshly prepared LDA in THF [prepared by adding n-butyllithium (2.92 ml of 1.6 M solution in hexanes, 4.67 mmol) to diisopropylamine (4.67 mmol, 0.655 ml) in THF (5 ml) at −78° C., then warming the solution to 0° C. for 20 min, and finally cooling back to −78° C.]. The reaction mixture was stirred at −78° C. for 1 h and at −40° C. for 30 min and was cooled back to −78° C. A pre-cooled (−78° C.) solution of aldehyde 67 (0.272 g, 1.95 mmol, 1 equiv) in THF (10 ml) was then added via cannula to the mixture over 2 min. The reaction mixture was stirred at −78° C. for 15 min before it was quenched rapidly by injection of a solution of acetic acid (0.55 ml) in THF (1.64 ml). The mixture was stirred at −78° C. for 5 min and brought to room temperature. Saturated aqueous ammonium chloride (20 ml) and ether (25 ml) were added and the layers were separated. The aqueous layer was extracted with ether (3×25 ml) and the organic extracts were combined, dried over anhydrous sodium sulfate, and concentrated in vacuo. Flash column chromatography (4-20% ether/hexanes) gave recovered ketone 68 (0.78 g) followed by syn aldol 79 (0.87 g, 83%) as the pure diastereomer along with other syn aldol diastereomer (74 mg, 7%) as colorless oils: $[\alpha]^{22}_D$=−39.6 (c=0.7, CHCl$_3$); TLC R$_f$=0.57 (silica gel, 20% ether/hexanes); $^1$H NMR (600 MHz, CDCl$_3$) δ 4.665 (s, 1H), 6.646 (s, 1H), 3.89-3.87 (dd, $^3$J=2.4 Hz, $^2$J=7.8 Hz, 1H), 3.67-3.63 (m, 1H), 3.60-3.55 (m, 1H), 3.30-3.267 (m, 2H), 2.05-1.95 (m, 2H), 1.69 (s, 3H), 1.76-1.26 (m, 7H), 1.187 (s, 3H), 1.074 (s, 3H), 1.02-1.00 (d, $^3$J=6.6 Hz, 3H), 0.881 (s, 9H), 0.866 (s, 9H), 0.826-0.814 (d, $^3$J=7.2 Hz, 3H), 0.087 (s, 3H), 0.062 (s, 3H), 0.017 (s, 6H); $^{13}$C NMR (100 MHz, CDCl$_3$) δ 222.265, 146.460, 109.855, 75.094, 74.327, 60.707, 54.246, 41.468, 38.440, 35.692, 32.820, 26.388, 26.322, 26.169, 25.030, 23.108, 22.646, 20.702, 18.569, 18.512, 15.590, 9.843, −3.500, −3.847, −5.043; HRMS calcd for C$_{30}$H$_{62}$O$_4$Si$_2$+Na$^+$ 565.4084; found 565.4067 [M+Na$^+$].

(3S,6R,7S,8S)-Carbonic acid-1-[4,6-bis-(tert-butyl-dimethyl-silanyloxy)-1,3,3-trimethyl-2-oxo-hexyl]-2,6-dimethyl-1-hept-6-enyl ester 2,2,2-trichloro-ethyl Ester (80)

To a solution of aldol 79 (0.80 g, 1.48 mmol) in methylene chloride (30 ml) at 0° C. was added pyridine (0.96 ml, 11.84 mmol, 8 equiv) followed by 2,2,2-trichloroethyl chloroformate (0.8 ml, 5.92 mmol, 4 equiv), and the reaction mixture was stirred at 0° C. for 1 h. Saturated aqueous sodium bicarbonate (50 ml) was added and the organic layer was separated. The aqueous layer was extracted with methylene chloride (3×50 ml), and the combined organic layers were dried over anhydrous sodium sulfate and concentrated in vacuo. Purification by flash column chromatography (2% EtOAc/hexanes) afforded protected aldol 80 (0.98 g, 93%) as a colorless oil: $[\alpha]^{22}_D$=−51.5 (c=1.6, CHCl$_3$); TLC R$_f$=0.72 (silica gel, 17% EtOAc/hexanes); $^1$H NMR (600 MHz, CDCl$_3$) δ 4.85 (d, $^2$J=12 Hz, 1H), 4.80-4.77 (dd, $^3$J=4.2 Hz, $^2$J=7.8 Hz, 1H), 4.66 (d, $^2$J=12 Hz, 1H), 4.66 (s, 1H), 4.62 (s, 1H), 3.73-3.71 (dd, $^3$J=2.4 Hz, $^2$J=7.8 Hz, 1H), 3.63-3.59 (m, 1H), 3.58-3.53 (m, 1H), 3.50-3.45 (m, 1H), 1.98-1.91 (m, 2H), 1.72-1.61 (m, 2H), 1.67 (s, 3H), 1.51-1.42 (m, 2H), 1.31-1.24 (m, 3H), 1.34 (s, 3H), 1.044-1.033 (d, $^3$J=6.6 Hz, 3H), 0.99 (s, 3H), 0.947-0.936 (d, $^3$J=6.6 Hz, 3H), 0.88 (s, 9H), 0.85 (s, 9H), 0.082 (s, 6H), 0.001 (s, 6H); $^{13}$C NMR (100 MHz, CDCl$_3$) δ 215.766, 154.468, 145.791, 110.288, 95.014, 83.144, 76.852, 75.824, 60.513, 53.846, 42.693, 38.225, 34.978, 31.541, 26.351, 26.140, 24.911, 23.718, 22.559, 21.231, 18.578, 16.341, 11.320, −3.281, −4.123, −5.047, −5.080; HRMS calcd for C$_{33}$H$_{63}$Cl$_3$O$_6$Si$_2$+Na$^+$ 739.3126; found 739.3163 [M+Na$^+$].

(3S,6R,7S,8S)-Carbonic acid-1-[4-(tert-butyl-dimethyl-silanyloxy)-6-hydroxy-1,3,3-trimethyl-2-oxo-hexyl]-2,6-dimethyl-1-hept-6-enyl ester 2,2,2-trichloro-ethyl Ester (81)

A solution of bis-silyl compound 80 (0.8 g, 1.11 mmol, 1 equiv) in methylene chloride (30 ml) and methanol (20 ml) was cooled to 0° C. To this solution was added a solution of (1S)-(+)-10-camphorsulfonic acid (77 mg, 0.33 mmol, 0.3 equiv) in methanol (10 ml). The reaction mixture was stirred at 0° C. for 7 h before it was quenched with saturated aqueous sodium bicarbonate (10 ml). The solid precipitate was filtered and the filtrate was concentrated in vacuo. The residue was diluted with ether (100 ml) and washed with brine. The organic layer was separated and the aqueous layer was extracted with ether (3×20 ml). The combined organic phases were dried over anhydrous sodium sulfate and concentrated in vacuo. Purification by flash column chromatography (10% EtOAc/hexanes) afforded the unstable alcohol 81 (0.583 g, 87%). It was used directly in the next step; TLC R$_f$=0.57 (silica gel, 33% EtOAc/hexanes); $^1$H NMR (600 MHz, CDCl$_3$) δ 4.87-4.80 (m, 2H), 4.69-4.61 (m, 3H), 3.93-3.90 (dd, $^3$J=3.0 Hz, $^2$J=7.8 Hz, 1H), 3.67-3.59 (m, 2H), 3.45-3.40 (m, 1H), 1.98-1.90 (m, 2H), 1.66 (s, 3H), 1.1.70-1.42 (m, 8H), 1.256 (s, 3H), 1.07-1.06 (m, 6H), 0.957-0.946 (d, $^3J$=6.6 Hz, 3H), 0.886 (s, 9H), 0.101 (s, 3H), 0.084 (s, 3H).

(3S,6R,7S,8S)-3-(tert-butyl-dimethyl-silanyloxy)-4,4,6,8,12-pentamethyl-5-oxo-7-(2,2,2-trichloro-ethoxycarbonyloxy)-tridec-12-enoic Acid (83)

Dess-Martin periodinane (0.545 g, 1.28 mmol, 1.4 equiv) was added to a solution of alcohol 81 (0.550 g, 0.914 mmol) in methylene chloride (4 ml). The mixture was stirred at room temperature for 15 min. Additional amount of Dess-Martin reagent (0.23 g, 0.6 equiv) was added and the reaction mixture was stirred for 15 min and then was subjected to flash column chromatography (10% EtOAc/hexanes) to furnish crude aldehyde 82 that was used directly in the next step. A solution of sodium dihydrogenphosphate (270 mg, 2.25 mmol, 2.46 equiv) and sodium chlorite (270 mg, 3 mmol, 3.27 equiv) in distilled water (5 ml) was added to the crude aldehyde 82 (ca 0.914 mmol) in t-butanol (25 ml) and 2-methyl-2butene (6 ml). The mixture was stirred at room temperature for 1 h and quenched by addition of saturated aqueous ammonium chloride (50 ml) and water (50 ml). The mixture was extracted with ethyl acetate (3×60 ml), and the combined organic extracts were dried over anhydrous sodium sulfate and concentrated in vacuo. Purification by flash column chromatography (10% EtOAc/hexanes) afforded the pure carboxylic acid 83 (0.505 g, 90% over two steps) as a colorless oil; $[\alpha]^{22}_D$=−53.7 (c=0.8, CHCl$_3$); TLC R$_f$=0.58 (silica gel, 40% EtOAc/hexanes); $^1$H NMR (600 MHz, CDCl$_3$) 4.858-4.838 (d, $^2J$=12 Hz, 1H), 4.78-4.75 (dd, $^3J$=4.2 Hz, $^2J$=7.2 Hz, 1H), 4.66 (d, $^2J$=12 Hz, 1H), 4.66 (s, 1H), 4.617 (s, 1H), 4.227-4.210 (dd, $^3J$=3.6 Hz, $^2J$=6.6 Hz, 1H), 3.47-3.41 (m, 1H), 2.62-2.57 (dd, $^3J$=3.6 Hz, $^2J$=17.4 Hz, 1H), 2.226-2.187 (dd, $^3J$=6.6 Hz, $^2J$=16.8 Hz, 1H), 1.96-1.913 (m, 2H), 1.74-1.68 (m, 1H), 1.66 (s, 3H), 1.52-1.42 (m, 2H), (s, 3H), 1.289-1.261 (d, $^3J$=16.8 Hz, 3H), 1.055 (s, 6H), 0.949-0.937 (d, $^3J$=7.2 Hz, 3H), 0.859 (s, 9H), 0.099 (s, 3H), 0.029 (s, 3H); $^{13}$C NMR (100 MHz, CDCl$_3$) δ 215.511, 177.734, 154.746, 145.771, 124.163, 110.296, 94.968, 82.665, 76.876, 75.045, 53.784, 42.446, 39.962, 38.204, 34.949, 31.537, 26.289, 26.173, 24.841, 23.029, 22.559, 20.306, 18.367, 16.275, 11.481, −4.300, −4.325; HRMS calcd for C$_{27}$H$_{47}$Cl$_3$O$_7$Si+Na$^+$ 639.2054; found 639.2079 [M+Na$^+$].

(1S,2E,5S)-Triethyl-(2-methyl-3-phenyl-5-vinyl-cyclopent-2-enyloxy)-silane (84)

To a pre-cooled (0° C.) solution of methyltriphenylphosphonium bromide (455 mg, 1.27 mmol, 2 equiv) in THF (5 ml) was added n-butyllithium (0.775 ml of 1.6 M solution in hexanes, 1.24 mmol, 1.95 equiv) dropwise. The reaction mixture was stirred at 0° C. for 30 min. A solution of aldehyde 56 (0.2 g, 0.633 mmol) in THF (2 ml) was added and the mixture was stirred at 0° C. for 30 min and quenched with a saturated aqueous ammonium chloride (5 ml). The solvent was removed under reduced pressure, and the aqueous residue was extracted with ethyl acetate (3×5 ml). The combined organic extract was dried over anhydrous sodium sulfate and concentrated in vacuo. Purification by flash column chromatography (5% ether/hexanes) afforded pure olefin 84 (0.14 g, 71%) as a colorless oil: $[\alpha]^{22}_D$=−14.3 (c=0.4, CHCl$_3$); TLC R$_f$=0.73 (silica gel, 10% ether/hexanes); $^1$H NMR (600 MHz, CDCl$_3$) 7.34-7.21 (m, 5H), 5.94-5.88 (m, 1H), 5.14-5.10 (d, $^2J$=16.8 Hz, 1H), 5.05-5.03 (dd, $^3J$=1.8 Hz, $^2J$=10.2 Hz, 1H), 4.53-4.52 (d, $^2J$=4.8 Hz, 1H), 2.88-2.82 (m, 1H), 2.74-2.68 (m, 1H), 2.52-2.47 (m, 1H), 1.82 (s, 3H), 0.99-0.96 (t, $^2J$=7.8 Hz, 9H), 0.68-0.63 (q, $^2J$=7.8 Hz, 6H); 13c NMR (100 MHz, CDCl$_3$) δ 141.063, 138.117, 136.318, 135.736, 128.561, 128.277, 127.959, 127.584, 126.915, 115.198, 87.030, 52.072, 40.420, 13.11 7.190, 5.482; HRMS calcd for C$_{20}$H$_{30}$OSi+Na$^+$ 337.1964 found 337.1970 [M+Na$^+$].

(1S,2E,5S)-2-Methyl-3-phenyl-5-vinyl-cyclopent-2-enol (69)

To a solution of compound 84 (0.48 g, 1.53 mmol) in THF (7 ml) at 0° C. was added tetrabutylammonium fluoride (1.53 ml of 1 M solution in THF, 1.53 mmol) dropwise. The reaction mixture was stirred at 0° C. for 30 min and then water (6 ml) and ethyl acetate (10 ml) were added. The layers were separated and the aqueous layer was extracted with ethyl acetate (2×10 m). The combined organic layers were dried over anhydrous sodium sulfate and concentrated in vacuo. Purification by flash column chromatography (10% EtOAc/hexanes) afforded pure alcohol 69 (0.245 g, 80%) as a white solid: $[\alpha]^{22}_D$=−14.17 (c=1.2, CHCl$_3$); TLC R$_f$=0.45 (silica gel, 33% EtOAc/hexanes); $^1$H NMR (600 MHz, CDCl$_3$) 7.36-7.23 (m, 5H), 6.00-5.94 (p, 1H), 5.21-5.16 (dd, $^3J$=1.2 Hz, $^2J$=16.8 Hz, 1H), 5.10-5.07 (dd, $^3J$=0.6 Hz, $^2J$=10.2 Hz, 1H), 4.48-4.47 (d, $^3J$=6.6 Hz, 1H), 2.85-2.81 (m, 1H), 2.71-2.65 (m, 1H), 2.59-2.54 (m, 1H), 1.89 (s, 3H); $^{13}$C NMR (100 MHz, CDCl$_3$) δ 140.407, 137.762, 136.322, 135.893, 128.388, 127.864, 127.146, 115.408, 86.349, 52.369, 39.756, 12.958; HRMS calcd for C$_{14}$H$_{16}$O+Na$^+$ 223.1099; found 223.1100 [M+Na$^+$].

(3S,6R,7S,8S)-3-(tert-Butyl-dimethyl-silanyloxy)-4,4,6,8,12-pentamethyl-5-oxo-7-(2,2,2-trichloro-ethoxycarbonyloxy)-tridec-12-enoic acid-(1S,2E,5S)-2-methyl-3-phenyl-5-vinyl-cyclopent-2-enyl Ester (85)

To a solution of acid 83 (13 mg, 0.021 mmol), alcohol 69 (4.6 mg, 0.023 mmol, 1.1 equiv), and DMAP (1 mg, 0.008 mmol, 0.4 equiv) in methylene chloride (0.5 ml) at 0° C. was added DCC (0.027 ml of 1 M solution in CH$_2$Cl$_2$, 0.027 mmol, 1.3 equiv) dropwise. The reaction mixture was stirred for 15 min at 0° C. and for 16 h at room temperature. The solid precipitate was filtered off and the filtrate was concentrated in vacuo. Purification by flash column chromatography (5% ether/hexanes) afforded ester 85 (11 mg, 64%) as a colorless oil: $[\alpha]^{22}_D$=−53.2 (c=0.85, CHCl$_3$); TLC R$_f$=0.67 (silica gel, 25% EtOAc/hexanes); $^1$H NMR (600 MHz, CDCl$_3$) 7.36-7.25 (m, 5H), 5.98-5.91 (m, 1H), 5.71-5.69 (d, $^3J$=4.2 Hz, 1H), 5.12-5.09 (d, $^3J$=17.4 Hz, 1H), 5.04-5.02 (d, $^3J$=10.2 Hz, 1H), 4.88-4.85 (m, 1H), 4.72-4.69 (dd, $^3J$=3 Hz, $^2J$=8.4 Hz, 1H), 4.66-4.60 (m, 3H), 4.30-4.28 (t, $^3J$=4.2 Hz, 1H), 3.50-3.46 (m, 1H), 2.96-2.92 (m, 1H), 2.86-2.81 (m, 1H), 2.70-2.66 (dd, $^3J$=3.6 Hz, $^2J$=17.4 Hz, 1H), 2.59-2.55 (m, 1H), 2.25-2.21 (dd, $^3J$=5.4 Hz, $^2J$=17.4 Hz, 1H), 1.95-1.87 (m, 2H), 1.75 (s, 3H), 1.66 (s, 3H), 1.54-1.53 (m, 6H), 1.33-1.27 (m, 6H), 1.06-1.04 (m, 3H), 0.966-0.955 (d, $^3J$=6.6 Hz, 3H), 0.87 (s, 9H), 0.129 (s, 3H), 0.054 (s, 3H); $^{13}$C NMR (100 MHz, CDCl$_3$) δ 172.341, 154.439, 145.783, 139.611, 139.334, 137.267, 132.349, 128.417, 127.959, 127.435, 115.284, 110.284, 95.010, 88.252, 82.347, 76.860, 75.020, 55.987, 54.007, 47.570, 42.223, 40. 465, 40.267, 38.217, 35.151, 34.883, 31.826, 31.170, 26.219, 25.678, 24.927, 24.795, 22.666, 22.547, 20.653, 18.363, 16.069, 13.103, 11.081, −4.069, −4.532; HRMS calcd for C$_{41}$H$_{61}$Cl$_3$O$_7$Si+Na$^+$ 821.3150; found 821.3178 [M+Na$^+$].

(3S,6R,7S,8S)-3,7-Dihydroxy-4,4,6,8,12-pentamethyl-5-oxo-tridec-12-enoic acid-(1S,2E,5S)-2-methyl-3-phenyl-5-vinyl-cyclopent-2-enyl Ester (66)

To a solution of ester 85 (12 mg, 0.015 mmol) in dry ethanol (1.5 ml) was added anhydrous ammonium chloride (75 mg) followed by zinc dust (75 mg). The reaction mixture was stirred at room temperature for 45 min before it was diluted with ethyl acetate (5 ml) and filtered though a plug of celite. The solution was concentrated and passed though a small plug of silica gel to give compound 86 that was used in the next step without further purification. To the crude solution of compound 86 was added a solution of tris(dimethylamino)sulfur (trimethylsilyl)difluoride (TAS-F) (5 mg, 0.187 mmol, 1 equiv) in 0.2 ml N,N-dimethylforamide. After 24 h, another 5 mg of TAS-F was added and the mixture was diluted with ethyl acetate (5 ml) and washed with pH 7 buffer (5 ml). The aqueous layer was extracted with ethyl acetate (3×5 ml) and the combined organic layers were dried over anhydrous sodium sulfate, filtered, and concentrated in vacuo. The crude oil was purified by silica gel chromatography (10% EtOAc/hexanes) to give pure compound 66 (4.7 mg, 62% over two steps) as a colorless material: $[\alpha]^{22}{}_D = -77.5$ (c=0.2, CHCl$_3$); TLC R$_f$=0.74 (silica gel, 50% EtOAc/hexanes); $^1$H NMR (600 MHz, CDCl$_3$) 7.37-7.25 (m, 5H), 6.0-5.92 (m, 1H), 5.76-5.75 (d, $^3$J=3.6 Hz, 1H), 5.15-5.11 (d, $^3$J=16.8 Hz, 1H), 5.07-5.04 (d, $^3$J=10.2 Hz, 1H), 4.67-4.64 (d, $^3$J=10.2 Hz, 1H), 4.29-4.26 (m, 1H), 3.39-3.35 (m, 2H), 3.27-3.23 (m, 2H), 2.99-2.93 (m, 1H), 2.88-2.83 (m, 1H), 2.61-2.57 (m, 1H), 2.54-2.50 (dd, $^3$J=1.8 Hz, $^2$J=16.2 Hz, 1H), 2.46-2.41 (dd, $^3$J=10.2 Hz, $^2$J=16.2 Hz, 1H), 2.04-1.96 (m, 2H), 1.79 (s, 3H), 1.72-1.75 (m, 1H), 1.69 (s, 3H), 1.54-1.52 (m, 1H), 1.36-1.30 (m, 1H), 1.20-1.18 (s overlapping with m, 4H), 1.15 (s, 3H), 1.07-1.05 (d, $^3$J=7.2 Hz, 3H), 0.85-0.83 (d, $^3$J=7.2 Hz, 3H); $^{13}$C NMR (100 MHz, CDCl$_3$) δ 222.479, 173.245, 146.443, 139.776, 139.392, 137.114, 131.784, 128.467, 127.922, 127.559, 115.487, 109.888, 88.553, 75.049, 72.680, 52.278, 47.843, 41.105, 40.391, 38.431, 36.913, 35.688, 32.713, 25.047, 22.642, 21.478, 19.172, 15.722, 13.094, 10.210; HRMS calcd for C$_{32}$H$_{46}$O$_5$+Na$^+$ 533.3243; found 533.3213 [M+Na$^+$].

2E,4S,7S,10R,11S,12S,16Z,18S)-7,11-Dihydroxy-3,8,8,10,12,16-hexamethyl-2-phenyl-3a,7,8,10,11,12,13,14,15,17a-decahydro-1H,6H-4-oxa-cyclopentacyclohexadecene-5,9-dione (6b)

A solution of the second generation Grubb's catalyst (2 mg, 0.0024 mmol) (weighed under argon) in methylene chloride (1.5 ml) was added to a solution of compound 66 in methylene chloride (0.5 ml). The reaction mixture was heated at 50° C. for 16 h and applied directly to a preparative TLC (3:1 hexanes/EtOAc) to give slightly impure E and Z 6b separately (~55% overall yield). The Z isomer was purified by a second preparative TLC using (3% methanol in methylene chloride) to remove the last traces of the catalyst and to furnish the desired target molecule Z 6b (0.5 mg). $^1$H NMR (600 MHz, CDCl$_3$) 7.36-7.33 (m, 2H), 7.27-7.24 (m, 3H), 5.83-5.81 (d, $^3$J=7.2 Hz, 1H), 5.26-5.23 (d, $^3$J=10.2 Hz, 1H), 4.2-4.17 (m, 1H), 3.69-3.66 (m, 1H), 3.22-3.15 (m, 2H), 2.83-2.79 (dd, $^3$J=8.4 Hz, $^2$J=15.6 Hz, 1H), 2.67-2.66 (d, $^3$J=4.2 Hz, 1H), 2.6-2.55 (dd, $^3$J=10.8 Hz, $^2$J=16.8 Hz, 2H), 2.52-2.47 (m, 1H), 2.39-2.31 (m, 2H), 1.80-1.75 (s overlapping with m, 4H), 1.68 (s, 3H), 1.66-1.62 (m, 3H), 1.36 (s, 3H), 1.18-1.17 (d, $^3$J=6.6 Hz, 3H), 1.07 (s, 3H), 0.99-0.98 (d, $^3$J=7.2 Hz, 3H); HRMS calcd for C$_{30}$H$_{42}$O$_5$+Na$^+$ 505.2930 found 505.2893 [M+Na$^+$].

Ethyl-2-hydroxy-3-methyl-4-(5-methylpyridin-2-yl)-cyclopent-3-enecarboxylate (88, 89)

Trifluoroacetic acid (0.297 ml, 3.86 mmol) was added to a stirred solution of compound 87 (0.5 g, 1.93 mmol) in methylene chloride (6 ml). The solvent was removed on the rotavapor. The resulting residue was dissolved in methanol (7 ml) and cooled to 0° C. To this solution at 0° C. was added sodium borohydride (0.73 g, 19.3 mmol) rapidly at once. After stirring at 0° C. for 45 min, chloroform was added and the mixture was washed with saturated sodium bicarbonate solution and brine. The organic layer was dried over anhydrous Na$_2$SO$_4$, concentrated to get a cis/trans mixture of 88-91 (0.459 g, 91%, cis/trans-1:2) which were separated by silica gel chromatography (16-25% EtOAc/hexanes).

Cis Mixture (90, 91)

TLC R$_f$=0.29 (silica gel, 25% EtOAc/hexane); $^1$H NMR (C$_6$D$_6$, 600 MHz): δ 8.38 (s, 1H), 6.88-6.87 (m, 2H), 4.61 (s, 1H), 3.99-3.89 (m, 2H), 3.54-3.49 (m, 1H), 3.05-3.01 (m, 1H), 2.88-2.84 (m, 1H), 2.34-2.32 (d, 1H, $^3$J=7.8 Hz), 2.13 (s, 3H), 1.77 (s, 3H), 0.92-0.89 (q, 3H, $^3$J=14.4); $^{13}$C NMR (C$_6$D$_6$, 100 MHz): δ 172.878, 153.487, 149.938, 138.605, 136.162, 135.910, 130.716, 121.957, 81.993, 60.365, 46.457, 36.159, 17.766, 14.131, 13.801. HRMS calcd for C$_{15}$H$_{19}$NO$_3$+Na$^+$ 284.1263; found 284.1248 (M+Na$^+$).

(1R,2S)-Ethyl-2-acetoxy-3-methyl-4-(5-methylpyridin-2-yl)cyclopent-3-enecarboxylate (92)

Vinyl acetate (0.95 ml, 10.3 mmol) was added to a solution of (+/−) 88/89 (0.27 g, 1.03 mmol) in anhydrous pentane (3 ml). Amano PS-D lipase (0.27 g) and 4 Å MS (0.27 g) were added and the suspension was stirred at room temperature. The reaction was monitored by TLC and $^1$H NMR and after 3 days 49-50% conversion of (+/−) 88/89 to acetate 92 was achieved. The sieves and lipase were filtered and washed with ether. The solvent was removed and crude product was purified by column chromatography on silica (16% EtOAc/hexane) to give 93 (0.154 g, 49%) as a pale yellow oil. $[\alpha]^{20}{}_D = -40.6$ (c=1.0, CHCl$_3$); TLC R$_f$=0.26 (silica gel, 75% EtOAc/hexanes); $^1$H NMR (CDCl$_3$, 600 MHz) δ 8.44 (s, 1H), 7.48-7.46 (d, 1H, $^3$J=7.8 Hz), 7.20-7.19 (d, 1H, $^3$J=7.8 Hz), 6.07 (s, 1H), 4.20-4.18 (q, 2H, $^3$J=14.4 Hz), 3.22-3.16 (m, 1H), 3.05-3.01 (m, 2H), 2.32 (s, 3H), 2.09 (s, 3H), 1.28-1.25 (q, 3H, $^3$J=7.2 Hz). $^{13}$C NMR (CDCl$_3$, 100 MHz) δ 174.107, 170.926, 152.537, 150.004, 137.238, 136.727, 135.023, 137.767, 122.476, 85.867, 61.144, 48.470, 37.478, 21.268, 18.516, 14.398, 13.197. HRMS calcd for C$_{17}$H$_{21}$NO$_4$+Na$^+$ 326.1368; found 326.1354 (M+Na$^+$).

(1R,2S)-Ethyl-2-hydroxy-3-methyl-4-(5-methylpyridin-2-yl)cyclopent-3-enecarboxylate (88)

Anhydrous potassium carbonate (45.6 mg, 0.33 mmol) was added to a solution of 92 (100 mg, 0.33 mmol) in dry ethanol (2.8 ml) at 0° C. and the solution was stirred at room temperature for 12 hr. Ethanol was removed under reduced pressure and the residue was dissolved in methylene chloride and washed with saturated aqueous solution of ammonium chloride. The organic phase was dried over anhydrous sodium sulfate and the solvent was removed in vacuo. The residue was purified by flash column chromatography on silica (25% EtOAc/hexane) to give compound 88 (81 mg, 94%, 99% ee) as a pale yellow oil: $[\alpha]^{20}{}_D = -8.1$ (c=0.26, CHCl$_3$); TLC R$_f$=0.27 (silica gel, 75% EtOAc/hexanes); $^1$H NMR (C$_6$D$_6$, 600 MHz) δ 8.69 (s, 1H), 6.89-6.83 (m, 2H), 4.57 (s, 1H), 3.38-3.34 (m, 2H), 2.40-2.38 (m, 2H), 2.16-2.11 (m, 1H); $^{13}$C NMR (CDCl$_3$, 100 MHz) δ 174.602, 153.069, 149.938, 138.385, 136.681, 134.969, 131.441, 122.385, 84.064, 61.037, 51.692, 35.927, 18.483, 14.518, 13.070. HRMS calcd for C$_{15}$H$_{19}$NO$_3$+Na$^+$ 284.1263; found 284.1279 (M+Na$^+$).

(1R,2S)-3-Methyl-4-(5-methyl-pyridin-2-yl)-2-triethylsilanyloxy-cyclopent-3-enecarboxylic Acid Ethyl Ester (93)

Triethylsilyl chloride (145 μL, 0.863 mmol, 1.5 equiv) was added dropwise to a solution of alcohol 88 (150 mg, 0.575 mmol) and imidazole (17 mg, 1.72 mmol, 3 equiv) in methylene chloride (4 ml) at 0° C. After stirring at 0° C. for 2 hr, the reaction was quenched with water (2.5 ml), and extracted with ethyl acetate (3×5 ml). The organic extracts were washed with brine (3.5 ml), and dried over anhydrous sodium sulfate. Filtration and evaporation of the solvents in vacuo furnished an oily crude product which was purified by flash column chromatography on silica (2-7% EtOAc/hexanes-) to give 93 (198 mg, 92%) as a yellow oil: [α]$^{22}_D$=−51.04 (c=0.7, CHCl$_3$); TLC R$_f$=0.29 (silica gel, 25% EtOAc/hexanes); $^1$H NMR (600 MHz, CDCl$_3$) δ 8.41 (s, 1H), 7.45-7.42 (dd, 1H, $^3$J=1.8 Hz, $^2$J=8.4 Hz), 7.2-7.18 (d, 1H, $^3$J=7.8 Hz), 5.12 (d, 1H, $^3$J=4.8 Hz), 4.2-4.16 (dd, 2H, $^3$J=7.2 Hz, $^2$J=14.4 Hz), 3.17-3.12 (m, 1H), 3.0-2.89 (m, 2H), 2.3 (s, 3H), 1.97 (s, 3H), 1.29-1.26 (t, 3H, $^3$J=14.4 Hz), 0.98-0.95 (t, 9H, $^3$J=7.8 Hz), 0.67-0.63 (q, 6H, $^3$J=7.8 Hz); $^{13}$C NMR (100 MHz, CDCl$_3$) δ 175.31, 153.31, 149.87, 139.09, 136.51, 134.07, 131.15, 122.39, 84.53, 60.83, 51.58, 37.40, 18.42, 14.46, 13.31, 7.03, 5.15; HRMS calcd for C$_{21}$H$_{33}$NO$_3$Si+H$^+$376.2308; found 376.2302 [M+H$^+$].

(1R,2S)-3-Methyl-4-pyridin-2-yl-2-triethylsilanyloxy-cyclopent-3-enecarbaldehyde (94)

A solution of DIBAL-H (0.44 ml, 1.0 M in hexane, 0.44 mmol, 1.1 equiv) was added dropwise to a solution of silyl ether 93 (150 mg, 0.4 mmol) in toluene (2 ml) at −78° C. The reaction mixture was stirred at that temperature for 1 hr and quenched by dropwise addition of saturated NH$_4$Cl solution (0.2 ml). The reaction mixture was allowed to reach room temperature and a saturated solution of Rochelle salt (1 ml) and brine (0.4 ml) were added. The mixture was extracted with ethyl acetate (3×2 ml) and the combined organic extracts were dried over anhydrous sodium sulfate, filtered, and evaporated in vacuo to give crude aldehyde 94 as a yellow liquid which was used in the next step without further purification.

(3S,4S)-5-Methyl-2-(2-methyl-3-triethylsilanyloxy-4-vinyl-cyclopent-1-enyl)-pyridine (95)

To a pre-cooled (0° C.) solution of methyltriphenylphosphonium bromide (286 mg, 0.8 mmol, 2 equiv) in THF (3 ml) was added n-butyllithium (0.49 ml of 1.6 M solution in hexanes, 0.78 mmol, 1.95 equiv) dropwise. The reaction mixture was stirred at 0° C. for 30 min. A solution of crude aldehyde 94 (ca 0.4 mmol) in THF (1.5 ml) was added and the mixture was stirred at 0° C. for 30 min and quenched with a saturated aqueous ammonium chloride solution (3 ml). The solvent was removed under reduced pressure, and the aqueous residue was extracted with ethyl acetate (3×3 ml). The combined organic extracts were dried over anhydrous sodium sulfate and concentrated in vacuo. Purification by flash column chromatography on silica (7% EtOAc/hexanes) afforded pure olefin 95 (96 mg, 73%) as a yellowish oil: [α]$^{22}_D$=−21.29 (c=0.7, CHCl$_3$); TLC R$_f$=0.66 (silica gel, 33% EtOAc/hexanes); $^1$H NMR (600 MHz, CDCl$_3$) δ 8.42 (s, 1H), 7.45-7.42 (dd, 1H, $^3$J=1.8 Hz, $^2$J=7.8 Hz), 7.19-7.17 (d, 1H, $^3$J=7.8 Hz), 5.95-5.88 (m, 1H), 5.14-5.11 (d, 1H, $^3$J=16.8 Hz), 5.05-5.02 (d, 1H, $^3$J=10.8 Hz), 4.54 (d, 1H, $^3$J=5.4 Hz), 2.97-2.93 (m, 1H), 2.74-2.68 (m, 1H), 2.6-2.56 (m, 1H), 2.3 (s, 3H), 1.96 (s, 3H), 0.99-0.96 (t, 9H, $^3$J=7.8 Hz), 0.67-0.62 (q, 6H, $^3$J=7.8 Hz); $^{13}$C NMR (100 MHz, CDCl$_3$) δ 153.95, 149.82, 140.95, 139.83, 136.52, 134.99, 130.91, 122.40, 115.19, 87.15, 51.85, 39.15, 18.45, 13.44, 7.16, 5.49; HRMS calcd for C$_{20}$H$_{31}$NOSi+11+330.2253 found 330.2258 [M+H$^+$].

(1S,5S)-2-Methyl-3-(5-methylpyridin-2-yl)-5-vinyl-cyclopent-2-enol (96)

To a solution of compound 95 (50 mg, 0.152 mmol) in THF (1 ml) at 0° C. was added tetrabutylammonium fluoride (0.152 ml of 1 M solution in THF, 0.152 mmol) dropwise. The reaction mixture was stirred at 0° C. for 30 min and water (1 ml) and ethyl acetate (2 ml) were added. The layers were separated and the aqueous layer was extracted with ethyl acetate (2×2 ml). The combined organic layers were dried over anhydrous sodium sulfate and concentrated in vacuo. Purification by flash column chromatography on silica (16-50% EtOAc/hexanes) afforded pure alcohol 96 (28 mg, 83%) as a white solid: [α]$^{22}_D$=−26.0 (c 0.3, CHCl$_3$); TLC R$_f$=0.25 (silica gel, 50% EtOAc/hexanes); $^1$H NMR (600 MHz, CDCl$_3$) δ 8.43 (s, 1H), 7.47-7.44 (dd, 1H, $^3$J=1.8 Hz, $^2$J=7.8 Hz), 7.19-7.17 (d, 1H, $^3$J=7.8 Hz), 6.0-5.95 (m, 1H), 5.12-5.17 (d, 1H, $^3$J=16.8 Hz), 5.09-5.06 (d, 1H, $^3$J=10.2 Hz), 4.48 (s, 1H), 2.96-2.91 (m, 1H), 2.69-2.60 (m, 2H), 2.32 (s, 3H), 2.03 (s, 3H); $^{13}$C NMR (100 MHz, CDCl$_3$) δ 153.62, 149.90, 140.25, 139.41, 136.65, 135.55, 131.19, 122.32, 115.43, 86.42, 52.26, 38.52, 18.49, 13.17; HRMS calcd for C$_{14}$H$_{17}$NO+Na$^+$ 238.1208; found 238.1191 [M+Na$^+$].

(3S,6R,7S,8S,1'S,5'S)-3-(tert-Butyl-dimethyl-silanyloxy)-4,4,6,8,12-pentamethyl-5-oxo-7-(2,2,2-trichloro-ethoxycarbonyloxy)-tridec-12-enoic Acid 2-methyl-3-(5-methyl-pyridin-2-yl)-5-vinyl-cyclopent-2-enyl Ester (97)

To a solution of acid 83 (8.0 mg, 0.013 mmol), alcohol 96 (3.0 mg, 0.014 mmol, 1.1 equiv), and DMAP (1 mg, 0.008 mmol, 0.6 equiv) in methylene chloride (0.5 ml) at 0° C. was added DCC (0.017 ml of 1 M solution in CH$_2$Cl$_2$, 0.017 mmol, 1.3 equiv) dropwise. The reaction mixture was stirred for 15 min at 0° C. and for 16 h at room temperature. The solid precipitate was filtered off and the filtrate was concentrated in vacuo. Purification by flash column chromatography on silica (5% EtOAc/hexanes) afforded ester 97 (10 mg, 95%) as a colorless oil: [α]$^{22}_D$=−29.8 (c=1, CHCl$_3$); TLC R$_f$=0.48 (silica gel, 25% EtOAc/hexanes); $^1$H NMR (600 MHz, CDCl$_3$) δ 8.43 (s, 1H), 7.47-7.45 (dd, 1H, $^3$J=1.8 Hz, $^2$J=7.8 Hz), 7.19-7.17 (d, 1H$^{13}$J=7.8 Hz), 5.98-5.91 (m, 1H), 5.74-5.72 (d, 1H, $^3$J=4.8 Hz), 5.13-5.09 (d, 1H, $^3$J=16.8 Hz), 5.03-5.01 (d, 1H$^3$J=10.2 Hz), 4.88-4.85 (d, 1H, $^3$J=12 Hz), 4.73-4.70 (m, 1H), 4.67-4.61 (m, 3H), 4.3-4.28 (m, 1H), 3.5-3.45 (m, 1H), 3.06-3.02 (m, 1H), 2.88-2.83 (m, 1H), 2.7-2.65 (m, 1H), 2.89 (s, 3H), 2.25-2.21 (dd, 1H, $^3$J=5.4 Hz, $^2$J=17.4 Hz), 1.98-1.91 (m, 2H), 1.9 (s, 1H), 1.76-1.74 (m, 1H), 1.66 (s, 3H), 1.5-1.22 (m, 5H), 1.1-1.04 (m. 6H), 0.97-0.95 (d, 3H, $^3$J=7.2 Hz), 0.87 (m, 12H), 0.127 (s, 3H), 0.05 (s, 3H); $^{13}$C NMR (100 MHz, CDCl$_3$) δ 215.42, 194.80, 172.30, 154.43, 153.12, 149.97, 145.78, 139.48, 138.30, 136.66, 135.68, 131.50, 125.53, 122.48, 115.36, 110.28, 95.01, 88.24, 82.37, 75.05, 53.98.

47.48, 42.24, 40.25, 39.19, 38.21, 34.89, 31.82, 29.93, 26.28, 24.79, 22.65, 22.54, 20.69, 18.49, 18.35, 16.08, 13.37, 11.08, −4.07, −4.54; HRMS calcd for $C_{41}H_{62}Cl_3NO_7Si+H^+$ 814.3434; found 814.3481 [M+H$^+$].

(3S,6R,7S,8S,1'S,5'S)-3,7-Dihydroxy-4,4,6,8,12-pentamethyl-5-oxo-tridec-12-enoic acid 2-methyl-3-(5-methyl-pyridin-2-yl)-5-vinyl-cyclopent-2-enyl ester (99)

To a solution of ester 97 (5 mg, 0.006 mmol) in DMF (0.2 ml) was added a solution of tris(dimethylamino)sulfur (trimethylsilyl)difluoride (TAS-F) (1.7 mg, 0.008 mmol, 1 equiv) in 0.2 ml N,N-dimethylforamide. After 24 h, another 1.7 mg of TAS-F was added and the mixture was diluted with ethyl acetate (3 ml) and washed with pH 7 buffer (5 ml). The aqueous layer was extracted with ethyl acetate (3×5 ml) and the combined organic layers were dried over anhydrous sodium sulfate, filtered, and concentrated in vacuo. The crude oil was purified by silica gel chromatography (10% EtOAc/hexanes) to give compound 98 which was dissolved in dry ethanol (1.2 ml) and treated with anhydrous ammonium chloride (62 mg) followed by zinc dust (62 mg). The reaction mixture was stirred at room temperature for 45 min before it was diluted with ethyl acetate (3 ml) and filtered though a plug of celite. The solution was concentrated and purified by silica gel chromatography (20% EtOAc/hexanes) to give pure compound 99 (2 mg, 62% over two steps) as a colorless material: $^1$H NMR (500 MHz, CDCl$_3$) 8.48 (s, 1H), 7.50 (m, 1H), 7.22-7.20 (d, $^3J$=8.5 Hz, 1H), 5.98 (m, 1H), 5.81 (m, 1H), 5.18-5.14 (d, $^3J$=17.5 Hz, 1H), 5.08-5.06 (d, $^3J$=10.5 Hz, 1H), 4.69-4.67 (d, $^3J$=9 Hz, 2H), 4.31-4.28 (d, $^3J$=10.5 Hz, 1H), 3.40 (m, 2H), 3.27 (dd, $^3J$=7 Hz, $^2J$=14.5 Hz, 2H), 3.07 (m, 1H), 2.91 (m, 1H), 2.70 (m, 1H), 2.54 (dd, $^3J$=2.5 Hz, $^2J$=16.5 Hz, 1H), 2.46 (dd, $^3J$=10.5 Hz, $^2J$=16.5 Hz, 1H), 2.36 (s, 3H), 1.98 (s, 3H), 1.72 (s, 3H), 1.26 (s, 3H), 1.22 (s, 3H), 1.17 (s, 3H), 1.08 (d, $^3J$=6.5 Hz, 3H), 0.87 (d, $^3J$=7 Hz, 3H); $^{13}$C NMR (100 MHz, CDCl$_3$) δ 222.14, 172.91, 152.80, 149.79, 146.19, 139.09, 139.13, 136.47, 135.04, 131.39, 122.29, 109.66, 88.31, 74.86, 72.54, 52.08, 47.50, 40.99, 38.96, 38.24, 36.79, 35.52, 32.53, 29.71, 24.88, 22.40, 21.29, 19.01, 18.28, 15.55, 13.16, 10.01; HRMS calcd for $C_{32}H_{47}NO_5+Na^+$ 548.3352 found 548.3331 [M+Na$^+$].

(3S,6R,7S,8S,1'S,5'S)-7,11-Dihydroxy-3,8,8,10,12,16-hexamethyl-2-(5-methyl-pyridin-2-yl)-3a,7,8,10,11,12,13,14,15,17a-decahydro-1H,6H-4-oxa-cyclopentacyclohexadecene-5,9-dione (100)

A solution of the second generation Grubb's catalyst (2 mg, 0.0024 mmol) (weighed under argon) in methylene chloride (1.5 ml) was added to a solution of compound 99 (2 mg, 0.0042 mmol) in methylene chloride (0.5 ml). The reaction mixture was heated at 50° C. for 16 h and applied directly to a preparative TLC (3:1 hexanes/EtOAc) to give the target Z 100 (0.5 mg) and a long with phenyl analogue 101 and the dimer 102 (~0.5 mg each). Data for compound 100; $^1$H NMR (500 MHz, CDCl$_3$) 8.60 (s, 1H), 8.17 (d, $^3J$=8 Hz, 1H), 7.54 (d, $^3J$=8 Hz, 1H), 5.84 (d, $^3J$=7 Hz, 1H), 5.25 (d, $^3J$=10 Hz, 1H), 4.43 (d, $^3J$=10 Hz, 1H), 3.63 (m, 1H), 3.43 (m, 1H), 3.23 (m, 2H), 2.81 (dd, $^3J$=2.5 Hz, $^2J$=16.5 Hz, 1H), 2.65 (dd, $^3J$=10.5 Hz, $^2J$=16.5 Hz, 1H), 2.59 (s, 3H), 2.0 (s, 3H), 1.72 (s, 3H), 1.42 (s, 3H) 1.16 (d, $^3J$=6.5 Hz, 3H), 1.06 (s, 3H), 1.02 (d, $^3J$=7 Hz, 3H); HRMS calcd for $C_{30}H_{43}NO_5+H^+$ 498.3219 found 498.3232 [M+H$^+$].

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

REFERENCES

1. Jordan, A.; Hadfield, John A.; Lawrence, N.J. and McGowan, A. Tubulin as a target for anticancer drugs: agents which interact with the mitotic spindle. Med. Res. Rev. 1998, 18, 259-296.
2. Wani, M. C.; Taylor, H. L.; Wall, M. E.; Coggon, P.; and McPhail, A. Plant antitumor agents. VI. The isolation and structure of taxol, a novel antileukemic and antitumor agent from Taxus brevifolia. J. Am. Chem. Soc. 1971, 93, 2325-2327.
3. Rowinsky, E. K. and Donehower, R. C. Taxol: twenty years later, the story unfolds. J. Natl. Cancer I. 1991, 83, 1778-1781.
4. Schiff, P. B.; Fant, J., and Horwitz, S. B. Promotion of microtubule assembly in vitro by taxol. Nature 1979, 277, 665-667.
5. Jordan, M. A.; Toso, R. J.; Thrower, D. and Wilson, L. Mechanism of mitotic block and inhibition of cell proliferation by taxol at low concentrations. Proc. Natl. Acad. Sci. U.S.A. 1993, 90, 9552-9556.
6. Chau, M.; Jennewein, S.; Walker, K. and Croteau, R. Taxol biosynthesis molecular cloning and characterization of a cytochrome P450 taxoid 7-beta-hydroxylase. Chem. Biol. 2004, 11, 663-672.
7. Denis, J. N.; Greene, A. E.; Guenard, D.; Gueritte-Voegelein, F.; Mangatal, L. and Potier, P. Highly efficient, practical approach to natural taxol. J. Am. Chem. Soc. 1988, 110, 5917-5919.
8. Baloglu, E. and Kingston, D. I. A new semisynthesis of paclitaxel from baccatin III. J Nat. Prod. 1999, 62, 1068-1071.
9. Haar, E; Kowalski R.; Hamel, E.; Lin, C.; Longley, R.; Gunaselcera, S.; Rosenluanz, H. and Day B. Discodermolide, A cytotoxic marine agent that stabilizes microtubules more potently than taxol. Biochemistry. 1996, 35, 243-250.
10. Longley, E.; Caddigan, D.; Harmody, D.; Gunasekera, M. and Gunasekera, S. Discodermolide—a new, marine-derived immunosuppressive compound. I. In vitro studies. Transplantation 1991, 52, 650-656.
11. D'Ambrosio, M.; Guerriero, A. and Pietra, F. Sarcodictyin A and sarcodictyin B, novel diterpenoidic alcohols esterified by (E)-N(1)-methylurocanic acid. Isolation from the Mediterranean stolonifer Sarcodictyon roseum. Helv. Chim. Acta 1987, 70, 2019-2027.
12. Lindel, T.; Jensen, P.; Fenical, W.; Long, B.; Casazza, A.; Carboni, J. and Fairchild, C. Eleutherobin, a new cytotoxin that mimics paclitaxel (taxol) by stabilizing microtubules. J. Am. Chem. Soc. 1997, 119, 8744-8745.
13. Corley, D.; Herb, R.; Moore, R.; Scheuer, P. and Paul, V. Laulimalides. New potent cytotoxic macrolides from a marine sponge and a nudibranch predator. J. Org. Chem. 1988, 53, 3644-3646.
14. Hofle, G.; Bedrof, N.; Gerth, K. and Reichenbach, H. (GBF). Epothilone derivatives. DE-B 4138042, 1993 (Chem. Abstr. 1993, 120, 52841).

15. Gerth K.; Bedorf N.; Hofle G.; Irschik H. and Reichenbach H Epothilones A and B: antifungal and cytotoxic compounds from *Sorangium cellulosum* (*Myxobacteria*). Production, physico-chemical and biological properties. *J. Antibiot.* 1996, 49, 560-563.
16. Bollag, D.; McQueney, P.; Zhu, J.; Hensens, O.; Koupal, L.; Liesch, J.; Goetz, M.; Lazarides, E.; and Woods, C. Epothilones, a new class of microtubule-stabilizing agents with a taxol-like mechanism of action. *Cancer Res.* 1995, 55, 2325-2333.
17. Chou, T.; Zhang, X.; Balog, A.; Su, D.; Meng, D.; Savin, K.; Bertino, J. and Danishefsky, S. Desoxyepothilone B: An efficacious microtubule-targeted antitumor agent with a promising in vivo profile relative to epothilone B. *Proc. Natl. Acad. Sci. U.S.A.* 1998, 95, 9642-9647.
18. Hardt, I.; Steinmetz, H.; Gerth, K.; Sasse, F.; Reichenbach, H. and Höfle, G. New natural epothilones from *Sorangium cellulosum*, strains So ce90/B2 and So ce90/D13. isolation, structure elucidation, and SAR studies. *J. Nat. Prod.* 2001, 64, 847-856.
19. Hofle, G.; Bedorf, N.; Steinmetz, H.; Schomburg, D.; Gerth, K. and Reichenbach, H. Epothilone A and B-Novel 16-membered macrolides with cytotoxic activity: Isolation, crystal structure, and conformation in solution. *Angew. Chem. Int. Ed. Engl.* 1996, 35, 1567-1569.
20. Kowalski R.; Giannakakou P. and Hamel E. Activities of the microtubule-stabilizing agents epothilones A and B with purified tubulin and in cells resistant to paclitaxel. *J. Biol. Chem.* 1997, 272, 2534-2541.
21. Rao, S.; Horwitz, S, and Ringel, I. Direct photoaffinity labeling of tubulin with taxol. *J. Natl. Cancer I.* 1992, 84, 785-788.
22. Rao, S.; He, L.; Chakravarty, S.; Ojima, I.; Orr, G. and Horwitz, S. Characterization of the taxol binding site on the microtubule: Identification of Arg282 in β-tubulin as the site of photoincorporation of a 7-benzophenone analogue of taxol. *J. Biol. Chem.* 1999, 274, 37990-37994.
23. a. Nogales, E.; Wolf, S. and Downing, K. Structure of the α,β-tubulin dimer by electron crystallography. *Nature* 1998, 391, 199-203.
    b. Nogales, E.; Whittaker, M.; Milligan, R. and Downing, K. High-resolution model of the microtubule. *Cell* 1999, 96, 79-88.
24. Giannakakou, P.; Gussio, R.; Nogales, E.; Downing, K.; Zaharevitz, D.; Bollbuck, B.; Poy, G.; Sackett, D.; Nicolaou, K. and Fojo, T. A common pharmacophore for epothilone and taxanes: Molecular basis for drug resistance conferred by tubulin mutations in human cancer cells. *Proc. Natl. Acad. Sci. U.S.A.* 2000, 97, 2904-2909.
25. Carlomagno, T.; Blommers, M.; Meiler, J.; Jahnke, W.; Schupp, T.; Petersen, F.; Schinzer, D.; Altmann, K. and Griesinger, C. The high-resolution solution structure of epothilone a bound to tubulin: An understanding of the structure-activity relationships for a powerful class of antitumor agents. *Angew. Chem. Int. Ed. Engl.* 2003, 42, 2511-2515.
26. Nicolaou, K.; Scarpelli, R.; Bollbuck, B.; Werschkun, B.; Pereira, M., Wartmann; M., Altmann; K., Zaharevitz, D.; Gussio, R. and Giannakakou, P. Chemical synthesis and biological properties of pyridine epothilones. *Chem. Biol.* 2000, 7, 593-599.
27. Balog, A.; Meng, D.; Kamenecka, T.; Bertinato, P., Su, D.; Sorensen. E. and Danishefsky, S. Total synthesis of (−)-epothilone A. *Angew. Chem. Int. Ed. Engl.* 1996, 35, 2801-2803.
28. Nicolaou, K.; He, Y.; Vouloumis, D.; Vallberg, H. and Yang, Z. An approach to epothilones based on olefin metathesis. *Angew. Chem. Int. Ed.* 1996, 35, 2399-2401.
29. Schinzer, D.; Limberg, A.; Bauer, A.; Bohm, O. and Cordes, M. Total synthesis of (−)-epothilone A. *Angew. Chem. Int. Ed. Engl.* 1997, 36, 523-524.
30. Schinzer, D.; Bauer, A.; Bohm, O.; Limberg, A. and Cordes, M. Total synthesis of (−)-epothilone A. *Chem. Eur. J.* 1999, 5, 2483-2491.
31. Taylor, R.; Galvin, G.; Hilfiker, K. and Chen, Y. A formal total synthesis of epothilone A: Enantioselective preparation of the $C_1$-$C_6$ and $C_7$-$C_{12}$ fragments. *J. Org. Chem.* 1998, 63, 9580-9583.
32. Nicolaou, K.; King, N.; Finlay, M.; He, Y.; Roschangar, F.; Vourloumis, D.; Vallberg, H.; Sarabia, F.; Ninkovic, S, and Hepworth, D. Total synthesis of epothilone E and related side-chain modified analogues via a Stille coupling based strategy. *Bioorg Med. Chem.*, 1999, 7, 665-697.
33. Sawada, D. and Shibasaki, M. Enantioselective total synthesis of epothilone A using multifunctional asymmetric catalyses. *Angew. Chem. Int. Ed.* 2000, 39, 209-213.
34. Martin, H.; Drescher, M. and Mulzer, J. How stable are epoxides? A novel synthesis of epothilone B. *Angew. Chem. Int. Ed.* 2000, 39, 581-583.
35. Mulzer, J.; Mantoulidis, A. and Ohler, E. Total syntheses of epothilones B and D. *J. Org. Chem.* 2000, 65, 7456-7467.
36. Sawada, D.; Kanai, M. and Shibasaki, M. Enantioselective total synthesis of epothilones A and B using multifunctional asymmetric catalysis. *J. Am. Chem. Soc.* 2000, 122, 10521-10532.
37. Bode, J. and Carreira, E. Stereoselective syntheses of epothilones A and B via directed nitrile oxide cycloaddition. *J. Am. Chem. Soc.* 2001, 123, 3611-3612.
38. Mulzer, J.; Karig, G. and Pojarliev, P. A novel highly stereoselective total synthesis of epothilone B and of its (12R,13R) acetonide. *Tetrahedron Lett.* 2000, 41, 7635-7638.
39. Zhu, B. and Panek, J. Methodology based on chiral silanes in the synthesis of polypropionate-derived natural product-Total synthesis of epothilone A. *Eur. J. Org. Chem.* 2001, 9, 1701-1714.
40. Chappell, M.; Stachel, S.; Lee, C. and Danishefsky, S. En route to a plant scale synthesis of the promising antitumor agent 12,13-desoxyepothilene B. *Org. Lett.* 2000, 2, 1633-1636.
41. Zhu, B. and Panek, J. Total synthesis of epothilone A. *Org. Lett.* 2000 2, 2575-2578.
42. Altmann, K.; Wartmann, M. and Reilly, T. Epothilones and related structures—a new class of microtubule inhibitors with potent in vivo antitumor activity. *Biochim. Biophys. Acta* 2000, 1470, M79-M91.
43. Altmann, K.; Bold, G.; Caravatti, G.; End, N.; Florsheimer, A.; Guagnano, V.; O'Reilly, T. and Wartmann, M. Epothilones and their analogs—Potential new weapons in the fight against cancer *Chimia*, 2000, 54, 612-621.
44. Julien, B.; Shah, S.; Ziennann, R.; Goldman, R.; Katz, L.; Khosla, C. Isolation and characterization of the epothilone biosynthetic gene cluster from *Sorangium cellulosum*. *Gene* 2000, 249, 153-160.
45. Su, D.; Balog, A.; Meng, D.; Bertinato, P.; Danishefsky, S.; Zheng, Y.; Chou, T.; He, L. and Horwitz, S. Structure-activity relationships of the epothilones and the first in vivo comparison with paclitaxel. *Angew. Chem. Int. Ed. Engl.* 1997, 36, 2093-2096.
46. Nicolaou, K.; Vourloumis, D.; Li, T.; Pastor, J.; Winssinger, N.; He, Y.; Ninkovic, S.; Sarabia, F.; Vallberg, H.;

46. Roschangar, F.; King, N.; Ray, M.; Finlay, V.; Giannakakou, P.; Verdier-Pinard, P. and Hamel, E. Designed epothilones: combinatorial synthesis, tubulin assembly properties, and cytotoxic action against taxol-resistant tumor cells. *Angew. Chem. Int. Ed. Engl.* 1997, 36, 2097-2103.
47. Nicolaou, K.; Sarabia, F.; Ninkovic, S.; Finlay, M. and Boddy, C. Probing the ring size of epothilones: Total synthesis of [14]-, [15]-, [17]-, and [18]epothilones A. *Angew. Chem. Int. Ed. Engl.* 1998, 37, 81-84.
48. Nicolaou, K.; He, Y., Roschangar, F.; King, N.; Vourloumis, D. and Li, T. Total synthesis of epothilone E and analogues with modified side chains through the Stille Coupling reaction. *Angew. Chem. Int. Ed. Engl.* 1998, 37, 84-87.
49. Nicolaou, K.; Winssinger, N.; Pastor, J.; Ninkovic, S.; Sarabia, F.; He, Y.; Vourloumis, D.; Yang, Z.; Li, T.; Giannakakou, P. and Hamel, E. Synthesis of epothilones A and B in solid and solution phase. *Nature* 1997, 387, 268-272.
50. Su D.; Meng, D.; Bertinato, P.; Balog, A.; Sorensen, E.; Danishefsky, S.; Zheng, Y.; Chou, T.; He, L. and Horwitz, S. Total synthesis of (−) epothilone B: An extension of the Suzuli coupling method and insights into structure-activity relationships of the epothilones. *Angew. Chem. Int. Ed. Engl.* 1997, 36, 757-759.
51. Harris C. and Danishefsky S. Complex target-oriented synthesis in the drug discovery process: A case history in the dEpoB series. *J. Org. Chem.* 1999, 64, 8434-8456.
52. Hofle G.; Glaser N.; Leibold T. and Sefkow M. Epothilone A-D and their thiazole-modified analogs as novel anticancer agents. *Pure Appl. Chem.* 1999, 71, 2019-2024.
53. Winkler J.; Holland J.; Kasparec J. and Axelsen P. Design and synthesis of constrained epothilone analogs: The efficient synthesis of eleven-membered rings by olefin metathesis. *Tetrahedron* 1999, 55, 8199-8214.
54. Hofle G.; Glaser N.; Kiffe M.; Hecht H.; Sasse F. and Reichenbach H. N-oxidation of epothilone A-C and O-acyl rearrangement to C-19- and C-21-substituted epothilones. *Angew. Chem. Int. Ed.* 1999, 38, 1971-1974.
55. Johnson J.; Kim S.; Bifano M.; DiMarco J.; Fairchild C.; Gougoutas J.; Lee F.; Long B.; Tokarski J. and Vite G. Synthesis, structure proof, and biological activity of epothilone cyclopropanes. *Org. Lett.* 2000, 2, 1537-1540.
56. Schnizer D.; Altmann K.; Stuhlmann F.; Bauer A. and Wartmann M. Synthesis and biological evaluation of azaepothilones. *ChemBioChem* 2000, 1, 67-70.
57. Nicolaou, K.; Sarabia, F.; Finlay, M.; Ninkovic, S.; King, N.; Vourloumis, D. and He, Y. Total synthesis of oxazole- and cyclopropane-containing epothilone B analogs by the macrolactonization approach *Chem. Eur. J.* 1997, 3, 1971-1986.
58. Martin H.; Pojarliev P.; Kahlig H. and Mulzer J. The 12,13-diol cyclization approach for a truly stereo controlled total synthesis of epothilone B and the synthesis of a conformationally restrained analogue. *Chem. Eur. J.* 2001, 7, 2261-2271.
59. Taylor R. and Zajicek J. Conformational properties of epothilone. *J. Org. Chem.* 1999, 64, 7224-7228.
60. Nicolaou, K.; Ninkovic, S.; Finlay, M.; Sarabia, F. and Li, T. Total synthesis of 26-hydroxyepothilone B and related analogs. *Chem. Commun.*, 1997, 24, 2343-2344.
61. Nicolaou, K.; Namoto, K.; Ritzen, A.; Ulven, T.; Shoji, M.; Li, J.; D'Amico, G.; Liotta, D.; French, C.; Wartmann, M.; Altmann, K. and Giannakakou, P. Chemical synthesis and biological evaluation of cis- and trans-12,13-cyclopropyl and 12,13-cyclobutyl epothilones and related pyridine side chain analogues. *J. Am. Chem. Soc.* 2001, 123, 9313-9323.
62. Chou, T.; Dong, H.; Rivkin, A.; Yoshimura, F.; Gabarda, A.; Cho, Y.; Tong, William P. and Danishefslcy, S. Design and total synthesis of a superior family of epothilone analogues, which eliminate xenograft tumors to a nonrelapsable state. *Angew. Chem. Int. Ed. Engl.* 2003, 42, 4762-4767.
63. Borzilleri, R.; Zheng, X.; Schmidt, R.; Johnson, J.; Kim, S.; DiMarco, J.; Fairchild, C.; Gougoutas, J.; Lee, F.; Long, B. and Vite, G. A novel application of a Pd(0)-catalyzed nucleophilic substitution reaction to the regio- and stereoselective synthesis of lactam analogues of the epothilone natural products. *J. Am. Chem. Soc.* 2000, 122, 8890-8897.
64. Stachel, S.; Lee, C.; Danishefsky, S. and Guan, Y. On the interactivity of complex synthesis and tumor pharmacology in the drug discovery process: Total synthesis and comparative in vivo evaluation of 15-Aza Epothilones. *J. Org. Chem.* 2001, 66, 4369-4378.
65. Altmann, K.; Bold, G.; Caravatti, G.; Florsheimer, A.; Guagnano, V. and Wartmann, M. Synthesis and biological evaluation of highly potent analogues of epothilones B and D. *Bioorg. Med. Chem. Lett.* 2000, 10, 2765-2768.
66. Nicolaou, K.; Namoto, K.; Li, J. and Ward, D. Synthesis and biological evaluation of 12,13-cyclopropyl and 12,13-cyclobutyl epothilones. *ChemBioChem* 2001, 2, 69-75.
67. Skehan, P.; Storeng, R.; Scudiero, D.; Monks, A.; McMahon, J.; Vistica, D.; Warren, J. T.; Bokesch, H.; Kenney, S, and Boyd, M. New colorimetric assay for anticancer-drug screening. *J. Natl. Canc. Inst.* 1990, 82, 1107-1112.
68. Rubenstein, L.; Shoemaker, R.; Paull, K.; Simon, R.; Tosini, S.; Skehan, P.; Scudiero, D.; Monks, A. and Boyd, M. Comparison of in vitro anticancer-drug screening data generated with a tetrazolium assay versus a protein assay against a diverse panel of human tumor cell lines. *J. Natl. Canc. Inst.* 1990, 82, 1113-1118.
69. Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich, M.; Campbell, H. and Mayo, J. Feasibility of a high-flux anticancer drug screen using a diverse panel of cultured human tumor cell lines. *J. Natl. Canc. Inst.* 1991, 83, 757-766.
70. Moasser, M.; Sepp-Lorenzino, L.; Kohl, N.; Oliff, A.; Balog, A.; Su, D.; Danishefsky, S. and Rosen, N. Farnesyl transferase inhibitors cause enhanced mitotic sensitivity to taxol and epothilones. *Proc. Natl. Acad. Sci. U.S.A.* 1998, 95, 1369-1374.
71. Dustin, P. *Microtubules* Ed. 2, 1984, Berlin: Springer-Verlag, 182-183.
72. TerHaar, E.; Kowalski, R.; Hamel, E.; Lin, C.; Longley, R.; Gunasekera, S.; Rosenkranz, H. and Day, B. Discodermolide, a cytotoxic marine agent that stabilizes microtubules more potently than taxol. *Biochem.* 1996, 35, 243-250.
73. Jadhav, P.; Bhat, K.; Perumal, P. and Brown, H. Chiral synthesis via organoboranes. 6. Asymmetric allylboration via chiral allyldiallkylboranes. Synthesis of homoallylic alcohols with exceptionally high enantiomeric excess. *J. Org. Chem.* 1986, 51, 432-439.
74. Corey, E. and Helal, C. Reduction of carbonyl compounds with chiral oxazaborolidine catalysts: A new paradigm for enantioselective catalysis and a powerful new synthetic method. *Angew. Chem. Int. Ed.* 1998, 37, 1986-2012.
75. Mori, I.; Ishihara, K. and Heathcock, C. Acyclic stereoselection. 50. New stereoselective propanal/propanoic acid synthons for aldol reactions. *J. Org. Chem.* 1990, 55, 1114-17.
76. Stetter, H. and Krasselt, J. Addition of aldehydes to activated double bonds. XV. Synthesis of γ-diketones with heterocyclic substituents and their conversion to N-methylpyrrole and quinolizidine as exemplified by the indolizidine systems. *J. Heterocyclic Chem.* 1977, 14, 573-581.
77. Dale, J. and Mosher, H. Nuclear magnetic resonance enantiomer regents. Configurational correlations via nuclear magnetic resonance chemical shifts of diastereomeric mandelate, O-methylmandelate, and α-methoxy-α-trifluoromethylphenylacetate (MTPA) esters. *J. Am. Chem. Soc.* 1973, 95, 512-519.

78. Ohtani, I.; Kusumi, T.; Kashman, Yoel and Kakisawa, H. High-field FT NMR application of Mosher's method. The absolute configurations of marine terpenoids. *J. Am. Chem. Soc.* 1991, 113, 4092-4096.

79. Mayr, H.; Klein, H. and Sippel, E. Synthesis of 1,2,3,3,6,6-hexamethyl-1-cyclohexene—a cascade of C12H23+ carbenium ion rearrangements. *Chem. Ber.* 1983, 116, 3624-3630.

80. Heathcock, C.; Buse, C.; Kleschick, W.; Pirrung, M.; Sohn, J. and Lampe, J. Acyclic stereoselection. 7. Stereoselective synthesis of 2-alkyl-3-hydroxy carbonyl compounds by aldol condensation. *J. Org. Chem.* 1980, 45, 1066-1081.

81. Bal, B.; Childers, Wayne E. and Pinnick, H. Oxidation of α,β-unsaturated aldehydes. *Tetrahedron* 1981, 37, 2091-2096.

82. Sloan-Kettering Institute fir Cancer Research, USA, International patent Application WO 9901124, 1999.

83. Nicolaou, K., Hwang, C., Marron, B., DeFrees, S., Couladouros, E., Abe, Y., Carroll, P., and Snyder, J. Bridging of macrodithionolactones to bicyclic systems. Synthesis and Modeling of oxapolycyclic frameworks. *J. Am. Chem. Soc.* 1990, 112, 3040-3054.

84. Evans, D., Dow, R., Shih, T., Talcacs, J. and Zahler, R. Total synthesis of the polyether antibiotic Ionomycin. *J. Am. Chem. Soc.* 1990, 112, 5290-5313.

85. Evans, D.; Britton, T. and Ellman, J. Contrasteric carboximide hydrolysis with lithium hydroperoxide. *Tetrahedron Lett,* 1987, 28, 6141-6144.

86. Altmann, K.; Bold, G.; Caravatti, G.; Denni, D.; Florsheimer, A.; Schmidt, A.; Rihs, G. and Wartmann, M. The total synthesis and biological assessment of trans-epothilone A. *Helv. Chim. Acta* 2002, 85, 4086-4110.

87. Nicolaou, K.; Ninkovic, S.; Sarabia, F.; Vourloumis, D.; He, Y.; Vallberg, H.; Finlay, M. and Yang, Z. Total syntheses of epothilones A and B via a macrolactonization-based strategy. *J. Am. Chem. Soc.* 1997, 119, 7974-7991.

88. Inukai, T. and Yoshizawa, R. Preparation of 6-Ketoaldehydes by Acylation of Aldehyde Enamines. *J. Org. Chem.* 1967, 32, 404-407.

89. C. H. Heathcock in *Comprehensive Organic Synthesis, Vol.* 2, (EDs.: B. M. Trost, I. Fleming), Pergamon, Oxford, 1991, pp. 181-238.

90. Nicolaou, K.; Hepworth, D.; King, N.; Finlay, M.; Raymond V.; Scarpelli, R.; Pereira, M.; Manuela A.; Bollbuck, B.; Bigot, A.; Werschkun, B. and Winssinger, N. Total synthesis of 16-desmethylepothilone B, epothilone B10, epothilone F, and related side chain modified epothilone B analogues. *Chem. Eur. J.* 2000, 6, 2783-2800.

91. Grieco, P.; Gilman, S, and Nishizawa, M. Organoselenium chemistry. A facile one-step synthesis of alkyl aryl selenides from alcohols. *J. Org. Chem.* 1976, 41, 1485-1486.

92. 92a. Parks, J.; Wagner, B. and Holm, R. Syntheses employing pyridyllithium reagents. New routes to 2,6-disubstituted pyridines and 6,6'disubstituted 2,2'-bipyridyls. *J. Organomet. Chem.* 1973, 56, 53-66.

92b. Cacchi, S.; Caglioti, L. and Cemia, E. Polymer supported bromine; a new reagent for the α-bromination of ketones. *Synthesis* 1979, 1, 64-6.

93. Taber, D. and Silverberg, L. Enantioselective reduction of α-keto esters. *Tetrahedron Lett.* 1991, 32, 4227-30.

94. Luche, J. and Gemal, A. Lanthanoids in organic synthesis. 5. Selective reductions of ketones in the presence of aldehydes. *J. Am. Chem. Soc.* 1979, 101, 5848-5849.

95. Gemal, A. and Luche, J. Lanthanoids in organic synthesis. 6. Reduction of α-enones by sodium borohydride in the presence of lanthanoid chlorides: synthetic and mechanistic aspects. *J. Am. Chem. Soc.* 1981, 103, 5454-5459.

96. Gensler, W.; Johnson, F. and Sloan, A. Compounds related to podophyllotoxin. XII. Podophyllotoxone, picropodophyllotoxone, and dehydropodophyllotoxin. *J. Am. Chem. Soc.* 1960, 82, 6074-6081.

97. Patel, D.; VanMiddlesworth, F.; Donaubauer, J.; Gannett, P. and Sih, C. Synthesis of the proposed penultimate biosynthetic triene intermediate of monensin A. *J. Am. Chem. Soc.* 1986, 108, 4603-4614.

98. Chen, J.; Wang, T. and Zhao, K. Preparation and use of 1-iodoalkyl ylides. *Tetrahedron Lett.* 1994, 35, 2827-2828.

99. Miyaura, N.; Ishiyama, T.; Sasaki, H.; Ishikawa, M.; Sato, M. and Suzuki, A. Palladium-catalyzed inter- and intramolecular cross-coupling reactions of B-alkyl-9-borabicyclo[3.3.1]nonane derivatives with 1-halo-1-alkenes or haloarenes. Syntheses of functionalized alkenes, arenes, and cycloalkenes via a hydroboration-coupling sequence. *J. Am. Chem. Soc.* 1989, 111, 314-321.

100. Miyaura, N. and Suzuki, A. Palladium-Catalyzed Cross-Coupling Reactions of Organoboron Compounds. *Chem. Rev.* 1995, 95, 2457-2483.

101. Inanaga, J.; Hirata, K.; Saeke, H.; Katsuki, T. and Yamaguchi, M. A rapid esterification by means of mixed anhydride and its application to large-ring lactonization. *B. Chem. Soc. Jpn.* 1979, 52, 1989-1993.

102. Laganis, E. and Chenard, B. Metal silanolates: organic soluble equivalents for atomic oxygen ion (O-2). *Tetrahedron Lett.* 1984, 25, 5831-5834.

103. Scheidt, K.; Chen, H.; Follows, B.; Chemler, S.; Coffey, S, and Roush, W. Tris(dimethylamino)sulfonium difluorotrimethylsilicate, a mild reagent for the removal of silicon protecting groups. *J. Org. Chem.* 1998, 63, 6436-6437.

104. Schinzer, D.; Bauer, A. and Schieber, J. Syntheses of (–)-epothilone B. *Chem. Eur. J.* 1999, 5, 2492-2500.

What is claimed is:

1. A compound, comprising:

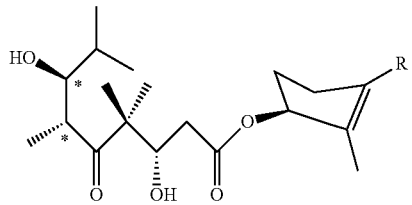

wherein R comprises phenyl, 2-pyridyl or other heteroaromatic.

2. A pharmaceutical composition comprising a therapeutically effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,893,268 B2 | Page 1 of 1 |
| APPLICATION NO. | : 11/989414 | |
| DATED | : February 22, 2011 | |
| INVENTOR(S) | : Viranga Tillekeratne, Richard D. Hudson and Mamoun Alhamadsheh | |

It is certified that error appears in the above-identified patent and that said Letters Patent is hereby corrected as shown below:

Title Page;
[54] The title of the invention should be -- Epothilone Analogues --.

Signed and Sealed this
Nineteenth Day of April, 2011

David J. Kappos
*Director of the United States Patent and Trademark Office*

UNITED STATES PATENT AND TRADEMARK OFFICE
CERTIFICATE OF CORRECTION

PATENT NO. : 7,893,268 B2  
APPLICATION NO. : 11/989414  
DATED : February 22, 2011  
INVENTOR(S) : Viranga Tillekeratne, Richard D. Hudson and Mamoun Alhamadsheh Page 1 of 1

It is certified that error appears in the above-identified patent and that said Letters Patent is hereby corrected as shown below:

Title Page, Item (54) and at Column 1, line 1,
    The title of the invention should be -- Epothilone Analogues --.

This certificate supersedes the Certificate of Correction issued April 19, 2011.

Signed and Sealed this  
Seventeenth Day of May, 2011

David J. Kappos  
*Director of the United States Patent and Trademark Office*